(12) United States Patent
Bassler et al.

(10) Patent No.: US 9,415,040 B2
(45) Date of Patent: *Aug. 16, 2016

(54) INHIBITION OF QUORUM SENSING-MEDIATED PROCESSES IN BACTERIA

(71) Applicant: The Trustees of Princeton University, Princeton, NJ (US)

(72) Inventors: Bonnie Bassler, Princeton, NJ (US); Lee Swem, San Carlos, CA (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,525

(22) Filed: May 8, 2015

(65) Prior Publication Data
US 2015/0238475 A1  Aug. 27, 2015

Related U.S. Application Data

(63) Continuation of application No. 14/028,999, filed on Sep. 17, 2013, now Pat. No. 9,045,476, which is a continuation of application No. 12/995,476, filed as application No. PCT/US2009/003348 on Jun. 2, 2009, now Pat. No. 8,568,756.

(60) Provisional application No. 61/188,310, filed on Aug. 7, 2008, provisional application No. 61/130,685, filed on Jun. 2, 2008.

(51) Int. Cl.
| | | |
|---|---|---|
| A01N 41/10 | (2006.01) |
| A01N 43/28 | (2006.01) |
| A01N 43/52 | (2006.01) |
| A01N 43/653 | (2006.01) |
| A01N 43/78 | (2006.01) |
| A01N 43/82 | (2006.01) |
| A01N 43/90 | (2006.01) |
| C07D 471/04 | (2006.01) |
| A61K 31/40 | (2006.01) |
| C07C 317/24 | (2006.01) |
| C07D 235/28 | (2006.01) |
| C07D 249/12 | (2006.01) |
| C07D 277/42 | (2006.01) |
| C07D 285/14 | (2006.01) |
| C07D 327/04 | (2006.01) |
| A61K 31/454 | (2006.01) |
| A61K 31/122 | (2006.01) |
| A61K 31/165 | (2006.01) |
| A61K 31/381 | (2006.01) |
| A61K 31/404 | (2006.01) |
| A61K 31/4184 | (2006.01) |
| A61K 31/4196 | (2006.01) |
| A61K 31/426 | (2006.01) |
| A61K 31/428 | (2006.01) |
| A61K 31/433 | (2006.01) |
| A61K 31/437 | (2006.01) |

(52) U.S. Cl.
CPC .............. *A61K 31/454* (2013.01); *A01N 41/10* (2013.01); *A01N 43/28* (2013.01); *A01N 43/52* (2013.01); *A01N 43/653* (2013.01); *A01N 43/78* (2013.01); *A01N 43/82* (2013.01); *A01N 43/90* (2013.01); *A61K 31/122* (2013.01); *A61K 31/165* (2013.01); *A61K 31/381* (2013.01); *A61K 31/40* (2013.01); *A61K 31/404* (2013.01); *A61K 31/4184* (2013.01); *A61K 31/4196* (2013.01); *A61K 31/426* (2013.01); *A61K 31/428* (2013.01); *A61K 31/433* (2013.01); *A61K 31/437* (2013.01); *C07C 317/24* (2013.01); *C07D 235/28* (2013.01); *C07D 249/12* (2013.01); *C07D 277/42* (2013.01); *C07D 285/14* (2013.01); *C07D 327/04* (2013.01); *C07D 471/04* (2013.01)

(58) Field of Classification Search
CPC ....... A01N 41/10; A01N 43/28; A01N 43/52; A01N 43/653; A01N 43/78; A01N 43/82; A01N 43/90
See application file for complete search history.

(56) References Cited

U.S. PATENT DOCUMENTS

| 8,247,443 B2 * | 8/2012 | Bassler et al. | 514/445 |
| 8,568,756 B2 * | 10/2013 | Bassler et al. | 424/405 |
| 9,045,476 B2 * | 6/2015 | Bassler et al. | C07D 471/04 |
| 2004/0180829 A1 | 9/2004 | Bassler | |
| 2005/0256181 A1 * | 11/2005 | Distefano et al. | 514/411 |
| 2007/0208012 A1 | 9/2007 | Ammendola | |
| 2011/0123586 A1 | 5/2011 | Bassler | |

OTHER PUBLICATIONS

Berge et al. "Pharmaceutical Salts" Journal of Pharmaceutical Sciences, 1977, vol. 66, pp. 1-18.*

(Continued)

*Primary Examiner* — Joseph Kosack
(74) *Attorney, Agent, or Firm* — Meagher Emanuel Laks Goldberg & Liao, LLP

(57) ABSTRACT

Methods are provided for identifying molecules that can be used to positively and negatively manipulate quorum-sensing-mediated communication to control bacterial behavior. Small-molecule antagonists that disrupt quorum-sensing-mediated activities are identified. Methods are provided for disrupting detection of acyl-homoserine lactone autoinducer in Gram-negative bacteria by contacting the bacteria with the antagonists. Methods of inhibiting quorum sensing-mediated activity in Gram-negative bacteria are provided wherein the activity is pathogenicity, bioluminescence, siderophore production, type III secretion, or metalloprotease production.

12 Claims, 33 Drawing Sheets

(56) References Cited

OTHER PUBLICATIONS

Timmon, et al., "Al-I Influences the Kinase Activity but not the Phosphatase Activity of LuxN of Vibrio harveyi" Journal of Biological Chemistry, vol. 281, pp. 24398-24404, (2006).
Tu, et al., "Multiple Small RNAs Act Additively to Integrate Sensory Information and Control Quorum Sensing in Vibrio harveyi" Genes & Development, vol. 21, pp. 221-233, (2007).
Waters, et al., "Quorum Sensing: Cell-to-Cell Communication in Bacteria" Annual Review of Cell Development Biology, vol. 21, pp. 319-346, (2005).
Zhu, et al., "Autoinducer Binding by the Quorum-Sensing Regulator TraR Increases Affinity for Target Promoters in Vitro and Decreases TraR Turnover Rates in Whole Cells" Proceedings of the National Academy of Science, vol. 96, pp. 4832-4837, (1999).
Zhu, et al. "The Quorum-Sensing Transcriptional Regulator TraR Requires its Cognate Signaling Ligand for Protein Folding, Protease Resistance, and Dimerization" Proceedings of the National Academy of Science, vol. 98, pp. 1507-1512, (2001).
International Search Report and Written Opinion for International Application PCT/US09/03348; Dated Sep. 18, 2009.
Avdeenko, et al., "Thiocyanation of N-Arylsulfonyl-, N-Aroyl-, and N-[(N-Arylsulfonyl)benzimidoyl]-1,-4-benzoquinone Imines," Russian Journal of Organic Chemistry, vol. 45, No. 3, pp. 408-416 (2009).
Federle, et al., "Interspecies Communication in Bacteria" J Clinical Investigation vol. 112, No. 9, pp. 1291-1299, (2003).
Kuehne, et al., "Studies in Biomimetic Alkaloid Syntheses. 3. Syntheses of Ervinceine arid Vincadifformine Analogues from Tetrahydro-y-carbolines through Secodine Intermediates," Journal of Organic Chemistry, vol. D44, No. 7, pp. 1063-1068, (2007).
Ames, et al., "Collaborative Signaling by Mixed Chemoreceptor Teams in *Escherichia coli*." Proceedings of the National Academy of Sciences, vol. 99, pp. 7060-7065, (2002).
Bassler, et al., "Cross-Species Induction of Luminescence in the Quorum-Sensing Bacterium Vibrio Harveyi." Journal of Bacteriology, vol. 179, pp. 4043-4045, (1997).
Bassler, et al., "Intercellular Signalling in Vibrio Harveyi: Sequence and Function of Genes Regulating Expression of Luminescence" Molecular Microbiology, vol. 9, pp. 773-786, (1993).
Bassler, et al., "Sequence and Function of LuxO, a Negative Regulator of Luminescence in Vibrio harveyi" Molecular Microbiology, vol. 12, pp. 403-412, (1994).
Beringer, et al.,"Transfer of the Drug Resistance Transposon Tn5 to Rhizobium" Nature, vol. 276, pp. 633-634, (1978).
Bray, et al., "Receptor Clustering as a Cellular Mechanism to Control Sensitivity" Nature, vol. 393, pp. 85-88, (1998).
Cao, et al., "Purification and Structural Identification of an Autoinducer for the Luminescence System of Vibrio harveyi" The Journal of Biological Chemistry, vol. 264, No. 35, pp. 21670-21676, (1989).
Chen, et al. "Structural Identification of a Bacterial Quorum-Sensing Signal Containing Boron" Nature, vol. 415, pp. 545-549, (2002).
Datsenko, et al. "One-step Inactivation of Chromosomal Genes in *Escherichia coli* K-12 using PCR products" Proceedings of the National Academy of Sciences, vol. 97, No. 6640-6645, (2000).
Ditta, et al., "Broad Host Range DNA Cloning System for Gram-Negative Bacteria: Construction of a Gene Bank of Rhizobium meliloti." Proceedings of the National Academy of Sciences, vol. 77, pp. 7347-7351, (1980).
Endres, et al. "Chemotaxis Receptor Complexes: from Signaling to Assembly" PLoS Computational Biology, vol. 3, Iss. 7, (2007).
Engebrecht, et al. "Identification of Genes and Gene Products Necessary for Bacterial Bioluminescence" Proceeding of the Nationall Academy of Sciences, vol. 81, pp. 4154-4158, (1984).
Engebrecht et al., "Nucleotide Sequence of the Regulatory Locus Controlling Expression of Bacterial Genes for Bioluminescence" Nucleic Acids Research, vol. 15, pp. 10455-10467, (1987).

Freeman, et al. "A Genetic Analysis of the Function of LuxO, a Two-Component Response Regulator Involved in Quorum Sensing in Vibrio harveyi" Molecular Microbiology, vol. 31, pp. 665-677, (1999).
Freeman, et al., "Sequence and Function of LuxU: a Two Component Phosphorelay Protein that Regulates Quorum Sensing in Vibrio harveyi" Molecular Microbiology, vol. 31, pp. 665-677, (2000).
Freeman et al., "A Genetic Analysis of the Functions of LuxN: a Two-Component Hybrid Sensor Kinase that Regulates Quorum Sensing in Vibrio harveyi" Molecular Microbiology, vol. 35, pp. 139-149, (2000).
Fuqua, et al., "Regulation of Gene Expression by Cell-to-Cell Communication: Acyl-Homoserine Lactone Quorum Sensing" Annual Review Genetics,vol. 35, pp. 439-468, (2001).
Fuqua, et al., "Census and Consensus in Bacterial Ecosystems: the LuxR-LuxI Family of Quorum-Sensing Transcriptional Regulators" Annual Review of Microbiology, vol. 50, pp. 727-751, (1996).
Fuqua, et al. "Quorum Sensing in Bacteria: the LuxR-LuxI Family of Cell Density-Responsive Transcriptional Regulators" Journal of Bacteriology, vol. 176, pp. 269-275, (1194).
Goy, et al., "Sensory Transduction in *Escherichia coli*: Role of a Protein Methylation Reaction in Sensory Adaptation", Proceedings of National Academy of Sciences vol. 74, pp. 4964-4968, (1977).
Hammer, et al., "Quorum Sensing Controls Biofilm Formation in Vibrio Cholerae", Molecular Microbiology, vol. 150, pp. 101-104, (2003).
Henke, et al., "Quorum Sensing Regulates Type III Secretion in Vibrio harveyi and Vibrio Parahaernolyticus" Journal of Bacteriology, vol. 1186, pp. 3794-3805, (2004). (a).
Henke, et al., "Three Parallel Quorum-Sensing Systems Regulate Gene Expression in Vibrio harveyi" Journal of Bacteriology, vol. 86, pp. 6902-6914, (2004). (b).
Higgins, et al., "The Major Vibrio Cholerae Autoinducer and its Role in Virulence Factor Production", Nature, vol. 450, pp. 883-886, (2007).
Jung, et al., "The Quorum-Sensing Hybrid Histidine Kinase LuxN of Vibrio harveyi Contains a Periplasmically Located N Terminus" Journal of Bacteriology, vol. 189, pp. 2945-2948, (2007).
Kerry, et al., "Adaptation in Bacterial Chemotaxis: CheBdependent Modification Permits Additional Methylations of Sensory Transducer Proteins" Cell, vol. 29, pp. 761-772, (1982).
Kerry, et al., "The Methyl-Accepting Chemotaxis Proteins of *Escherichia coli*. Identification of the Multiple Methylation Sites on Methylaccepting Chemotaxis Protein" Journal of Biological Chemistry, vol. 257, pp. 10378-10386, (1982). (b).
Keymer, et al., "Chemosensing in *Escherichia coli*: Two Regimes of Two-State Receptors" Proceedings of the National Academy of Science, vol. 103, pp. 1786-1791, (2006).
Kim, et al. "Four-Helical-Bundle Structure of the Cytoplasmic Domain of a Serine Chemotaxis Receptor", Nature, vol. 400, pp. 787-792, (1999).
Lenz, et al. "The Small RNA Chaperone Hfq and Multiple Small RNAs Control Quorum Sensing in Vibrio harveyi and Vibrio Cholerae" Cell, vol. 118, pp. 69-82, (2004).
Maddock, et al., "Polar Location of the Chemoreceptor Complex in the *Escherichia coli* Cell." Science, vol. 259, pp. 1717-1723, (1993).
Martin, et al. "Identification of a Locus Controlling Expression of Luminescence Genes in Vibrio harveyi" Journal of Bacteriology, vol. 71, pp. 2406-2414, (1989).
McFall-Ngai, et al., "Developmental Biology in Marine Invertebrate Symbioses." Current Opinions in Microbiology, vol. 3, pp. 603-607, (2000).
Miller, et al., "Quorum Sensing in Bacteria" Annual Review in Microbiology, vol. 55, pp. 165-199, (2001).
Neiditch, et al., "Regulation of LuxPQ Receptor Activity by the Quorum-Sensing Signal Autoinducer-2" Molecular Cell, vol. 18, pp. 507-518, (2005).
Neiditch, et al., "Ligand-Induced Asymmetry in Histidine Sensor Kinase Complex Regulates Quorum Sensing" Cell, vol. 126, pp. 1095-1108, (2006).

(56) References Cited

OTHER PUBLICATIONS

Park et al., "Two-Domain Reconstitution of a Functional Protein Histidine Kinase" Proceedings of the National Academy of Science, vol. 95, pp. 6728-6732, (1998).

Sambrook et al., "Molecular Cloning: A Laboratory Manual" Cold Spring Harbor, NY, Cold Spring Harbor Laboratory Press, (1989).

Showalter, et al., "Cloning and Nucleotide Sequence of luxR, a Regulatory Gene Controlling Bioluminescence in Vibrio harveyi" Journal of Bacteriology, vol. 172, pp. 2946-2954, (1990).

Sourjik, V. "Receptor Clustering and Signal Processing in *E. coli* Chemotaxis" Trends in Microbiology, vol. 12, pp. 569-576, (2004).

Sourjik, et al. "Receptor Sensitivity in Bacterial Chemotaxis" Proceedings of the National Academy of Sciences, vol. 99, pp. 123-127, (2002).

Sourjik et al., "Functional Interactions Between Receptors in Bacterial Chemotaxis" Nature, vol. 428, pp. 437-441, (2004).

Springer, et al. Identification of a Protein Methyltransferase as the cheR Gene Product in the Bacterial Sensing System. Proceedings of the National Academy of Science, vol. 74, pp. 533-537, (1977).

Stock et al., "A Protein Methyl Esterase Involved in Bacterial Sensing" Proceedings of the National Academy of Science, vol. 75, pp. 3659-3663, (1978).

Surette, et al., "Quorum Sensing in *Escherichia coli, Salmonella Typhimurium*, and Vibrio harveyi: A New Family of Genes Responsible for Autoinducer Production" Proceedings of the National Academy of Science, vol. 96, pp. 1639-1644, (1999).

Svenningsen, et al., "A Negative Feedback Loop Involving Small RNAs Accelerates Vibrio Cholerae's Transition out of Quorum-sensing Mode", Genes & Development, vol. 22, pp. 226-238, (2008).

Terwilliger et al., "Sites of Methyl Esterification and Deamination on the Aspartate Receptor Involved in Chemotaxis" Journal of Biological Chemistry, vol. 259, pp. 7719-7725, (1984).

\* cited by examiner

```
                                        Section 19
                              (775) 775        780        790        800        817
     LuxN Vibrio harveyi (719)    ----------------------------------------
LuxN Vibrio parahaemolyticus (719) ----------------------------------------
    LuxN Vibrio splendidus (737) ----------------------------------------
   LuxN Vibrio alginolyticus (720) ----------------------------------------
 LuxN Listonella anguillarum (721) ----------------------------------------
      LuxN Vibrio sp Venter (738) KQTER-----------------------------------
 LuxN Photobacterium profundum (771) SIKMLRAGTHGHQAQTTPMFLYGYTENSEHLNSIELSPFFQGQ
LuxN Photobacterium phosphoreum (771) ALKKIRSGDFGANAQKIPLIALS---NENTRSTRFDTNVFQGE
        LuxN Vibrio fischeri (704) ----------------------------------------
       LuxN Vibrio angustum (769) QISMLREGKYGYLAQITPIFIFNSTSINLNNDRINVPKYTQGY
            LuxN Vibrionales (661) ----------------------------------------

Section 20
                              (818) 818        830        840        850        860
     LuxN Vibrio harveyi (719)    ----------------------------------QSPT-L-TIVDDKEVQ
LuxN Vibrio parahaemolyticus (719) ----------------------------------APT-A-TIVDDKFVQ
    LuxN Vibrio splendidus (737) ----------------------------------NHLAF-D-TIVDDKEVQ
   LuxN Vibrio alginolyticus (720) ----------------------------------APT-A-TIVDDKEVQ
 LuxN Listonella anguillarum (721) ----------------------------FLIN-----NKAP-T-TIVDDKEVQ
      LuxN Vibrio sp Venter (743) ----------------------TQAENQPASSHLA-T-A-TIVDDKEVQ
 LuxN Photobacterium profundum (814) IDGINDHQAFLHSLESLIDNDLFAKLGSLIGK--L-TVADMQMN
LuxN Photobacterium phosphoreum (811) FRISDSLPLFAQSLKLLIDSGSLKPLGHLIGKRN-LV-ADMQIN
        LuxN Vibrio fischeri (704) --------------------------SLK-D---HVDDKK-Q
       LuxN Vibrio angustum (812) IDTLNGALAFECSLEAIINDTKFEAPLGSLNDK-N-DDMHAN
            LuxN Vibrionales (661) ------------------------------SITF-L-LVDDKEVQ Section 21
                              (861) 861        870        880        890        903
     LuxN Vibrio harveyi (733) RALWQMYLNQLGVNSIQANKEMAWEVFKANHVPEINLVQMP
LuxN Vibrio parahaemolyticus (732) RTLWQMYVNRLGVNSIQANMGAMAVELFKTHKVPELNLVQMP
    LuxN Vibrio splendidus (753) RTLWQMYLNRLGVNSIQAKMGEMAWBLFHSHKIPLVLRDVQMP
   LuxN Vibrio alginolyticus (733) RTLWQMYLKRLGVNSIQANMGASAWBLFHSHKIPLVLMDVQMP
 LuxN Listonella anguillarum (740) RSLWQMYINQLGVNNIQANMGEMAWBLFKANSIPLVLMBFQMP
      LuxN Vibrio sp Venter (768) RTLWQMYISRLGVNSIQAKMGEMAVBLFRSHKVPLVLMDVQMP
 LuxN Photobacterium profundum (857) RMLWQMYIASEGITVVQASSGDEAIBKVKKEPFNVLABIQMP
LuxN Photobacterium phosphoreum (854) RMLWQFYIAQEGITVIQAHKGSVALCIAEQERPDLVLMNIHMP
        LuxN Vibrio fischeri (718) RMLIHTFINKDNLTLLQAEKGEAVEIATNNKLPLVLFMDSRMP
       LuxN Vibrio angustum (855) RLMKAFISKEINVIQAASGYEAIDQVKKNNIPLVLMDIHMP
            LuxN Vibrionales (676) RTLWQMYINRLGVNSIQAKMGEMAIBLFRKNHVPELALVQMP
```

CHARACTERIZATION OF AI-1 ANTAGONISTS

| ID NO. | WT.,mg | FORMULA *STRUCTURE | MOL. WT. | VOL. DMSO (mL) | g/L | CONC. (M) | SPECIFICITY | HIGHEST TESTED CONC. (uM) | CHEM. NAME |
|---|---|---|---|---|---|---|---|---|---|
| 6807-0002 | 1.1 | C14H11NO4S2 | 321.37 | 0.2 | 5.5 | 0.0171 | LuxN | 171.142297 | 4-METHYL-N-(2-OXOBENZO[d][1,3]OXATHIOL-5-yl)BENZENESULFONAMIDE |
| 8008-8157 | 1 | C19H12Cl2O3S | 391.27 | 0.2 | 5 | 0.0128 | LuxN | 127.789948 | (4-CHLOROPHENYL)(4-(4-CHLOROPHENYLSULFONYL)PHENYL)METHANONE |
| C104-0038 | 1.1 | C18H17ClN2 | 296.79 | 0.2 | 5.5 | 0.0185 | LuxN | 185.3162169 | 2-BENZYL-8-CHLORO-2,3,4,4a,5,9b-HEXAHYDRO-1H-PYRIDO[4,3-b]INDOLE |
| C105-2488 | 1 | C17H18N4O3S2 | 390.48 | 0.2 | 5 | 0.0128 | LuxN | 128.0475312 | 3-(1,3-DIHYDROBENZO[c][1,2,5]THIADIAZOLE-4-SULFONAMIDO)-N-(4-ETHYLPHENYL)PROPANAMIDE |
| 3448-8396 | 1 | C13H13F3N4OS | 330.33 | 0.2 | 5 | 0.0151 | LuxN | 151.3637877 | 2-(4-METHYL-4H-1,2,4-TRIAZOL-3-YLTHIO)-N-(3-(TRIFLUOROMETHYL)BENZYL)ACETAMIDE |
| 3578-0898 | 1.2 | C12H14N2O2S | 250.32 | 0.2 | 6 | 0.0240 | LuxN | 239.6931927 | ISOPROPYL 2-(1H-BENZO[d]IMIDAZOL-2-YLTHIO)ACETATE |
| 3643-3503 | 1 | C21H27NO2 | 325.44 | 0.2 | 5 | 0.0154 | LuxN | 153.6381514 | N-sec-BUTYL-2-(4-(2-PHENYLPROPAN-2-yl)PHENOXY)ACETAMIDE |
| 4052-1355 | 1 | C18H16N2OS | 308.44 | 0.2 | 5.5 | 0.0178 | LuxN | 178.3166904 | (Z)-4-(3-ALLYL-4-PHENYLTHIAZOL-2(3H)-YLIDENEAMINO)PHENOL |
| 4248-0174 | 1.1 | C22H27NO2 | 337.46 | 0.2 | 5.5 | 0.0163 | LuxN | 162.982794 | N-CYCLOPENTYL-2-(4-(2-PHENYLPROPAN-2-YL)PHENOXY)ACETAMIDE |
| 4401-0054 | 1 | C15H17ClN2O | 276.76 | 0.2 | 5 | 0.0181 | LuxN | 180.6619454 | 6-CHLORO-N-ETHYL-2,3,4,9-TETRAHYDRO-1H-CARBAZOLE-1-CARBOXAMIDE |
| 4606-4237 | 1 | C15H18ClNO3S | 327.83 | 0.2 | 5 | 0.0153 | LuxN | 152.5180734 | 4-(4-CHLORO-2-METHYLPHENOXY)-N-2-(2-OXOTETRAHYDROTHIOPHEN-3-yl)BUTANAMIDE |
| C137-0541 | 1.2 | C14H13N3O4S3 | 383.47 | 0.2 | 6 | 0.0156 | LuxN | 156.4659556 | N-(6-METHOXYBENZO[d]THIAZOL-2-yl)-2-(THIOPHENE-2-SULFONAMIDO)ACETAMIDE |
| C450-0730 | 1 | C23H28ClN3O4S | 478 | 0.2 | 5 | 0.0105 | LuxN | 104.6025105 | 2-(1-ACETYLINDOLINE-5-SULFONAMIDO)-N-(4-CHLOROBENZYL)-4-METHYLPENTANAMIDE |
| C540-0010 | 1 | C20H23N3OS | 353.48 | 0.2 | 5 | 0.0141 | LuxN | 141.4507186 | (2-ETHYLPIPERIDIN-1-yl)(3-METHYL-6-PHENYLIMIDAZO[2,1-d]THIAZOL-2-YL)METHANONE |
| C646-0078 | 1 | C21H25N3O4S2 | 447.57 | 0.2 | 5 | 0.0112 | LuxN | 111.7143687 | N-(4-METHOXYBENZYL)-3-METHYL-2-(2-METHYLBENZO[d]THIAZOLE-6-SULFONAMIDO)BUTANAMIDE |

AHL QUORUM SENSING
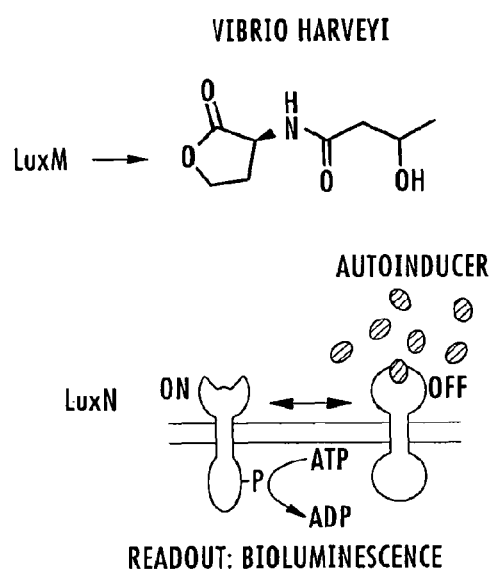
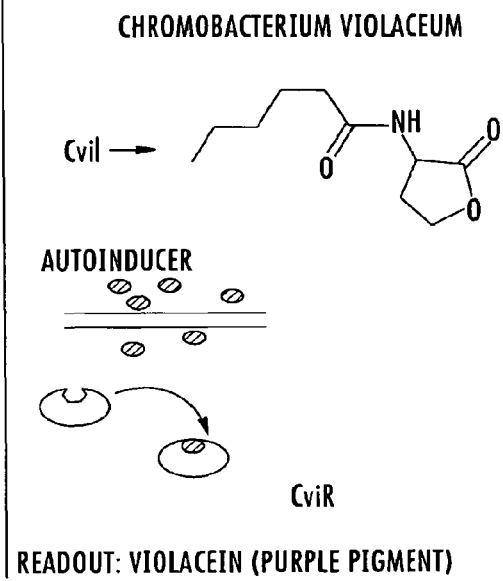
FIG. 10A
FIG. 10B

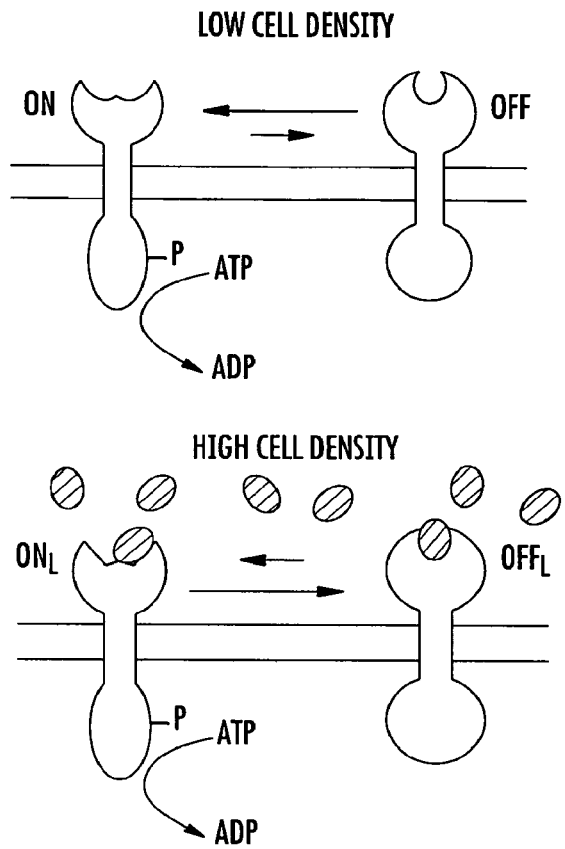
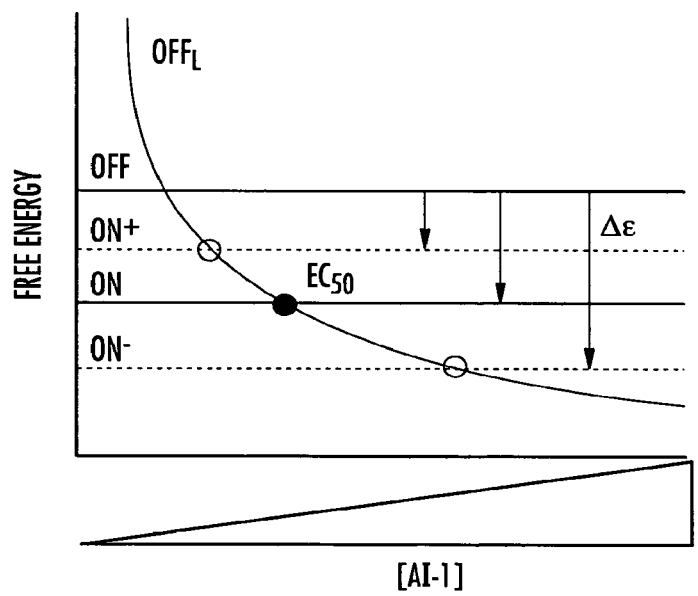
FIG. 14A
FIG. 14B

SEQUENCE LISTING

<160> NUMBER OF SEQ ID NOS: 11

<210> SEQ ID NO 1
<211> LENGTH: 849
<212> TYPE: PRT
<213> ORGANISM: Vibrio harveyi

<400> SEQUENCE: 1

Met Phe Asp Phe Ser Leu Glu Ala Ile Val Tyr Ala Lys Ala Ile Ser
1               5                   10                  15

Leu Leu Ala Thr Val Ala Val Val Met Met Trp Leu Phe Tyr Tyr Cys
            20                  25                  30

Tyr Arg Leu Lys Gln Lys Asn Glu Val Ile Phe Gly Thr His His Ala
        35                  40                  45

Ala Tyr Ile Ala Tyr Ser Val Cys Ile Ile Ala Trp Ile Ser Ser Asn
    50                  55                  60

```
Ala Tyr Phe His Thr Asp Leu Leu Pro Glu Leu Gly Ala Ser Ala Gly
 65                  70                  75                  80

Met Phe Met Ala Lys Phe Ala Asn Leu Ala Ser Phe Ala Phe Ala
             85                  90                  95

Phe Ala Tyr Tyr Phe Ser Cys Gln Leu Ala Ala Glu Gln Arg Lys Gly
            100                 105                 110

Lys Val His Arg Trp Gln Gln Gly Ile Phe Val Ser Leu Thr Val Tyr
            115                 120                 125

Ser Leu Phe Ile Asn Leu Arg Pro Gly Leu Thr Val Glu His Val Asp
            130                 135                 140

Ile Val Gly Pro Ser Gln Phe Ile Ile Glu Phe Gly Pro His Thr Ser
145                 150                 155                 160

Tyr Phe Phe Ile Gly Leu Val Ser Phe Val Leu Thr Leu Val Asn
                165                 170                 175

Leu Val Ala Met Arg Thr Asn Ser Ser Lys Leu Thr Leu Ala Lys Thr
                180                 185                 190

Asn Tyr Met Ile Ala Gly Ile Leu Val Phe Met Leu Ser Thr Ala Val
            195                 200                 205

Ile His Leu Gly Met Thr Tyr Phe Met Gly Asp Phe Ser Leu Thr Trp
210                 215                 220

Leu Pro Pro Ala Leu Ser Ile Ser Glu Met Leu Phe Val Gly Tyr Ala
225                 230                 235                 240

Leu Leu Thr Ser Arg Phe Tyr Ser Val Lys Tyr Ile Ala Tyr Leu Ala
                245                 250                 255

Leu Ser Val Leu Leu Val Cys Ala Ile Phe Val Leu Pro Leu Gly Ala
            260                 265                 270

Ile Phe Ile Pro Leu Thr Glu Ser Asn Gln Trp Leu Ala Ile Pro
            275                 280                 285

Ile Cys Ala Leu Ile Gly Ile Thr Trp Gln Leu Leu Tyr Lys Lys Thr
290                 295                 300

Ser Arg Tyr Ala Ser Phe Leu Ile Tyr Gly Asp Lys Lys Thr Pro Val
305                 310                 315                 320

Gln Gln Ile Leu Ser Leu Glu Glu Asp Phe Lys Leu Ser Ile Asp Asp
                325                 330                 335

Ala Met Arg Arg Leu Gly Lys Leu Leu Gln Ile Pro Asn Asp Lys Leu
            340                 345                 350

Arg Leu Val Thr Ser Asn Tyr Asn Glu Thr Phe Tyr Glu Glu Tyr Leu
            355                 360                 365

Ser Ser Asn Arg Ser Val Leu Val Phe Asp Glu Leu Ser Glu Glu Leu
            370                 375                 380

Glu Tyr Lys Val Ser Ala Lys Arg Ser Met Lys Ala Leu Tyr Asp Lys
385                 390                 395                 400

Met Ser Ser Asn Asn Thr Ala Leu Val Met Pro Leu Phe Gly Gln Gly
                405                 410                 415

Lys Ser Val Thr His Leu Leu Ile Ser Pro His Lys Ser Asn Asn Gln
            420                 425                 430

Met Phe Ser Asn Glu Glu Ile Ser Ala Val Gln Thr Leu Leu Thr Arg
            435                 440                 445

Val Gln Ser Thr Ile Glu Ala Asp Arg Arg Ile Arg Gln Ser Arg Ala
            450                 455                 460

Leu Ala Asn Ser Ile Ala His Glu Met Arg Asn Pro Leu Ala Gln Val
465                 470                 475                 480
```

```
Gln Leu Gln Phe Glu Ala Leu Lys Gln His Ile Glu Asn His Ala Pro
                485                 490                 495

Val Glu Gln Ile Thr Leu Asp Ile Glu Asn Gly Gln Ala Ala Ile Gln
            500                 505                 510

Arg Gly Arg Gln Leu Ile Asp Ile Ile Leu Arg Glu Val Ser Asp Ser
        515                 520                 525

Ser Pro Glu His Glu Pro Ile Ala Met Thr Ser Ile His Lys Ala Val
    530                 535                 540

Asp Gln Ala Val Ser His Tyr Gly Phe Glu Asn Glu Lys Ile Ile Glu
545                 550                 555                 560

Arg Ile Arg Leu Pro Gln His Thr Asp Phe Val Ala Lys Leu Asn Glu
                565                 570                 575

Thr Leu Phe Asn Phe Val Ile Phe Asn Leu Ile Arg Asn Ala Ile Tyr
            580                 585                 590

Tyr Phe Asp Ser Tyr Pro Asp Ser Gln Ile Glu Ile Ser Thr Lys Thr
        595                 600                 605

Gly Pro Tyr Glu Asn Thr Leu Ile Phe Arg Asp Thr Gly Pro Gly Ile
    610                 615                 620

Asp Glu Thr Ile Ser His Lys Ile Phe Asp Asp Phe Phe Ser Tyr Gln
625                 630                 635                 640

Lys Ser Gly Gly Ser Gly Leu Gly Leu Gly Tyr Cys Gln Arg Val Met
                645                 650                 655

Arg Ser Phe Gly Gly Arg Ile Glu Cys Lys Ser Lys Leu Gly Thr Phe
            660                 665                 670

Thr Glu Phe His Leu Tyr Phe Pro Val Val Pro Asn Ala Pro Lys Ala
        675                 680                 685

Asp Thr Leu Arg Thr Pro Tyr Phe Asn Asp Trp Lys Gln Asn Lys Arg
    690                 695                 700

Ser Asn Glu His Lys Val Ala Pro Asn Val Gln Ile Asn Asn Gln Ser
705                 710                 715                 720

Pro Thr Val Leu Ile Val Asp Asp Lys Glu Val Gln Arg Ala Leu Val
                725                 730                 735

Gln Met Tyr Leu Asn Gln Leu Gly Val Asn Ser Leu Gln Ala Asn Asn
            740                 745                 750

Gly Glu Asn Ala Val Glu Val Phe Lys Ala Asn His Val Asp Leu Ile
        755                 760                 765

Leu Met Asp Val Gln Met Pro Val Met Asn Gly Phe Asp Ala Ser Gln
    770                 775                 780

Arg Ile Lys Glu Leu Ser Pro Gln Thr Pro Ile Val Ala Leu Ser Gly
785                 790                 795                 800

Glu Ser Gly Glu Arg Glu Leu Asp Met Ile Asn Lys Leu Met Asp Gly
                805                 810                 815

Arg Leu Glu Lys Pro Thr Thr Leu Asn Ala Leu Arg His Val Leu Gly
            820                 825                 830

Asn Trp Leu Asn Lys Asn Thr Ala Ser Ser Ala Cys Glu Ala Glu Arg
        835                 840                 845

Glu

<210> SEQ ID NO 2
<211> LENGTH: 850
<212> TYPE: PRT
<213> ORGANISM: Vibrio parahaemolyticus

<400> SEQUENCE: 2
```

```
Met Leu Asp Ile Gly Leu Ser Gly Leu Leu Tyr Pro Lys Ala Ile Thr
1               5                   10                  15

Leu Phe Ala Thr Val Ala Val Val Leu Val Trp Leu Tyr Tyr Cys
            20                  25                  30

Tyr Arg Leu Lys Gln Lys Asn Glu Val Ile Leu Gly Ser Tyr His Ala
            35                  40                  45

Pro Tyr Ile Ala Tyr Ser Thr Cys Ile Ile Ile Trp Ile Ser Ser Asn
50                      55                  60

Ala Tyr Phe His Thr Asp Leu Leu Pro Leu Leu Gly Ser Glu Gly Gly
65                  70                  75                  80

Ile Phe Met Ala Lys Leu Ala Asn Leu Ala Ser Phe Phe Ala Phe Ala
                85                  90                  95

Phe Ala Phe Tyr Phe Ser Cys Gln Leu Ala Ala Glu Gln Lys Lys Gly
                100                 105                 110

Lys Val Lys Leu Trp Gln Gln Gly Ile Phe Val Ala Leu Thr Val Tyr
                115                 120                 125

Ser Leu Val Ile Asn Leu Arg Pro Asn Leu Thr Val Glu Asn Val Leu
        130                 135                 140

Ile Asp Gly Pro Ser Gln Phe Val Ile Glu Phe Gly Pro His Thr Ser
145                 150                 155                 160

Tyr Phe Phe Met Gly Leu Val Thr Phe Val Val Met Thr Leu Thr Asn
                165                 170                 175

Leu Ile Ser Met Arg Ala Asn Ser Ser Lys Leu Ser Ile Ala Lys Asn
                180                 185                 190

Asn Tyr Met Ile Ala Gly Ile Leu Val Phe Met Leu Ser Thr Ala Val
            195                 200                 205

Ile His Leu Gly Met Thr Tyr Phe Leu Gly Asp Phe Ser Leu Thr Trp
        210                 215                 220

Leu Pro Pro Ala Leu Ser Ile Ser Glu Met Leu Phe Val Gly Tyr Ala
225                 230                 235                 240

Leu Leu Thr Ser Arg Phe Tyr Ser Ala Lys Tyr Leu Ala Tyr Leu Thr
                245                 250                 255

Ile Ser Val Leu Phe Val Cys Thr Ile Phe Val Leu Pro Leu Gly Ala
                260                 265                 270

Val Phe Ile Pro Met Ser Glu Asp Asn Gln Trp Leu Ile Ser Ile Pro
        275                 280                 285

Ile Cys Ala Leu Ile Gly Ile Thr Trp His Leu Val Tyr Lys Arg Val
        290                 295                 300

Ser Arg Val Ala Ser Phe Phe Ile Tyr Gly Asn Arg Gln Thr Pro Val
305                 310                 315                 320

Gln Gln Ile Leu Ala Leu Glu Glu Phe Lys Arg Ser Ile Asp Asp
                325                 330                 335

Ala Val His Gln Leu Ser Thr Leu Leu Asn Ile Pro Asn Asp Lys Leu
                340                 345                 350

Gln Leu Val Thr Ser Asn Tyr Thr Glu Thr Phe Tyr Glu Asp Tyr Leu
            355                 360                 365

His Ser Asn Asp Ser Val Leu Val Leu Asp Glu Leu Ser Glu Arg Leu
        370                 375                 380

Asp Glu Lys Pro Ser Lys Gly Ser Ile Lys Ala Leu Tyr Glu Arg
385                 390                 395                 400

Met Arg Ser Ser Asn Thr Ala Leu Val Met Pro Leu Phe Gly Arg Glu
                405                 410                 415

Lys Ser Val Ser His Leu Leu Ile Ser Ser His Lys Ser Asp Asn Lys
```

```
            420                 425                 430
Leu Phe Ser Asn Glu Ile Ser Ala Leu Gln Thr Leu Leu Ile Arg
            435                 440                 445

Val Gln Asn Thr Ile Glu Ser Asp Arg Lys Ile Arg Gln Ser Arg Ala
            450                 455                 460

Leu Ala Asn Ser Ile Ala His Glu Met Arg Asn Pro Leu Ala Gln Val
465                 470                 475                 480

Gln Leu Gln Phe Glu Ala Leu Lys Gln His Ile Asp Ser Asn Ala Ser
            485                 490                 495

Asp Asp Lys Ile Arg Ser Asp Ile Glu Lys Gly Gln Ala Ala Ile Gln
            500                 505                 510

Arg Gly Arg Gln Leu Ile Asp Ile Ile Leu Arg Glu Val Ser Asp Thr
            515                 520                 525

Ser Ala Val His Glu Pro Leu Ser Leu Thr Ser Ile His Lys Ala Val
            530                 535                 540

Asp Leu Ala Val Ser Arg Tyr Gly Phe Glu Asn Glu His Ile Ile Glu
545                 550                 555                 560

Arg Val Lys Leu Pro Thr Gln Asn Asp Phe Val Ala Lys Ile Asn Glu
            565                 570                 575

Thr Leu Phe Asn Phe Val Ile Phe Asn Leu Ile Arg Asn Ala Ile Tyr
            580                 585                 590

Tyr Phe Asp Ser Tyr Pro Asp Ser Gln Ile Glu Ile Arg Thr Leu Val
            595                 600                 605

Gly Pro Tyr Glu Asn Thr Leu Val Phe Arg Asp Thr Gly Pro Gly Ile
            610                 615                 620

Asp Asp Ser Ile Leu His Lys Ile Phe Asp Asp Phe Phe Ser Phe Gln
625                 630                 635                 640

Lys Ser Gly Gly Ser Gly Leu Gly Leu Gly Tyr Cys Gln Arg Val Met
            645                 650                 655

Arg Ser Phe Gly Gly Arg Ile Glu Cys Lys Ser Val Thr Asn Glu Phe
            660                 665                 670

Thr Glu Phe Tyr Leu His Phe Pro Val Val Pro Asn Ala Pro Lys Val
            675                 680                 685

Glu Thr Leu Arg Thr Pro Asn Phe Tyr Asn Trp Asn Gln Lys Val Lys
            690                 695                 700

Thr Lys Pro Ser Pro Glu Pro Val Val Gln Ile Asn Lys Asp Ala Pro
705                 710                 715                 720

Thr Val Leu Ile Val Asp Asp Lys Glu Val Gln Arg Thr Leu Val Gln
                725                 730                 735

Met Tyr Leu Asn Arg Leu Gly Val Asn Ser Leu Gln Ala Asn Asn Gly
            740                 745                 750

Ala Asn Ala Val Glu Leu Phe Gln Ser His Gln Val Asp Leu Val Leu
            755                 760                 765

Met Asp Val Gln Met Pro Val Met Asn Gly Phe Asp Ala Ser Glu Lys
            770                 775                 780

Ile Lys Gln Cys Ser Pro Thr Thr Pro Ile Ile Ala Leu Ser Gly Glu
785                 790                 795                 800

Ser Gly Glu Lys Glu Leu Glu Met Ile Ala Lys Leu Met Asp Gly Arg
            805                 810                 815

Leu Glu Lys Pro Thr Thr Leu Asn Ala Leu Arg Asp Val Leu Val Arg
            820                 825                 830

Trp Leu His Phe Asp Lys Ile Ser Val Thr Asn Ser Tyr Gln Ile Ala
            835                 840                 845
```

Asn Glu
    850

<210> SEQ ID NO 3
<211> LENGTH: 871
<212> TYPE: PRT
<213> ORGANISM: Vibrio splendidus

<400> SEQUENCE: 3

Met Asn Met Phe Asp Phe Gly Leu Glu Ala Ile Val Tyr Ala Lys Ala
1               5                   10                  15

Ile Thr Leu Leu Ala Thr Val Ala Ile Val Met Trp Leu Leu Tyr
            20                  25                  30

Tyr Cys Tyr Arg Leu Arg Gln Lys Asn Lys Val Ile Phe Gly Thr His
        35                  40                  45

His Ala Pro Tyr Ile Ala Tyr Ser Ile Cys Ile Val Ala Trp Ile Cys
    50                  55                  60

Ser Asn Ala Tyr Phe His Thr Asp Leu Leu Pro Glu Leu Gly Ala Ser
65                  70                  75                  80

Ala Ala Val Tyr Ala Ala Lys Leu Ala Asn Leu Ala Ser Phe Cys Ala
                85                  90                  95

Phe Ala Phe Ala Tyr Tyr Phe Ser Cys Lys Leu Ala Ala Glu Gln Arg
            100                 105                 110

Asn Ser Lys Val His Pro Trp Gln Gln Ala Ile Phe Val Thr Leu Thr
        115                 120                 125

Val Tyr Ser Phe Phe Ile Asn Leu Ser Pro Gly Leu Thr Val Glu His
    130                 135                 140

Val Thr Ile Ala Gly Pro Ser Glu Phe Val Ile Glu Phe Gly Pro Tyr
145                 150                 155                 160

Thr Pro Tyr Phe Phe Thr Gly Val Ile Ser Leu Ile Ile Leu Thr Leu
                165                 170                 175

Leu Asn Leu Leu Ala Met Arg Ala Asn Ser Ser Lys Leu Ile Leu Ala
            180                 185                 190

Lys Thr Asn Tyr Met Ile Thr Gly Ile Leu Val Phe Met Leu Ser Thr
        195                 200                 205

Ala Thr Val His Ile Gly Ile Ala Tyr Phe Ile Arg Asp Phe Ser Leu
    210                 215                 220

Thr Trp Leu Pro Pro Ala Leu Ser Ile Ser Glu Met Leu Phe Val Gly
225                 230                 235                 240

Tyr Ala Leu Leu Thr Ser Arg Phe Tyr Ser Val Lys Tyr Leu Ala Tyr
                245                 250                 255

Met Ser Leu Asn Thr Leu Leu Val Cys Ala Ile Leu Val Ile Pro Phe
            260                 265                 270

Gly Ala Ile Phe Ile Pro Leu Thr Asp Asp Asn Gln Trp Leu Ile Ala
        275                 280                 285

Ile Pro Ile Cys Ala Val Ile Gly Ile Thr Trp His Leu Leu Tyr Lys
    290                 295                 300

Arg Val Ser Asp Tyr Ala Ser Phe Phe Ile Tyr Gly Asn Lys Lys Thr
305                 310                 315                 320

Pro Val Gln Gln Ile Leu Ala Leu Glu Glu Asp Phe Lys Leu Ser Ile
                325                 330                 335

Asp Asp Ala Met Arg Arg Leu Gly Ser Leu Leu Gln Ile Pro Glu Asp
            340                 345                 350

Lys Leu Arg Leu Val Asn Ser Asn Tyr Asn Glu Thr Phe Tyr Glu Asp

-continued

```
              355                 360                 365
Tyr Leu Ser Thr Asn Lys Ser Val Leu Val Phe Asp Glu Leu Ser Gln
            370                 375                 380

Glu Leu Asp Tyr Thr Ala Pro Ala Lys Arg Ser Ile Lys Ala Leu Tyr
385                 390                 395                 400

Asp Lys Met Ser Ser Asn Asp Thr Ala Leu Val Met Pro Leu Phe Gly
                405                 410                 415

Gln Gly Lys Ser Val Thr His Leu Leu Val Ser Ser His Lys Ser Asn
            420                 425                 430

Asp Gln Met Phe Ser Asn Glu Glu Ile Ser Ala Leu Gln Thr Leu Leu
                435                 440                 445

Thr Arg Val Gln Ser Thr Ile Glu Ala Asp Arg Arg Ile Arg Gln Ser
            450                 455                 460

Arg Ala Leu Ala Asn Ser Ile Ala His Glu Met Arg Asn Pro Leu Ala
465                 470                 475                 480

Gln Val Gln Leu Gln Phe Glu Leu Leu Lys Gln His Ile Asp Asn Gln
                485                 490                 495

Ala Pro Ala Lys Gln Ile Leu Leu Asp Ile Glu Asn Gly Gln Ala Ala
                500                 505                 510

Ile Gln Arg Gly Arg Gln Leu Ile Asp Ile Leu Arg Glu Val Ser
            515                 520                 525

Asp Ser Ser Pro Glu His Gly Pro Ile Thr Met Thr Ser Ile His Lys
530                 535                 540

Ala Val Asp Gln Ala Val Ser His Tyr Gly Phe Glu Asn Glu Lys Ile
545                 550                 555                 560

Ile Glu Arg Ile Arg Leu Pro Pro His Ala Asp Phe Val Ala Lys Leu
                565                 570                 575

Asn Glu Thr Leu Phe Asn Phe Val Ile Phe Asn Leu Ile Arg Asn Ala
            580                 585                 590

Ile Tyr Tyr Phe Asp Ser Tyr Pro Asp Ser Gln Ile Glu Ile Ser Thr
            595                 600                 605

Lys Thr Gly Ala Tyr Glu Asn Val Leu Thr Phe Arg Asp Thr Gly Pro
    610                 615                 620

Gly Ile Asp Glu Ala Ile His Lys Ile Phe Asp Asp Phe Phe Ser
625                 630                 635                 640

Tyr Gln Lys Ser Gly Gly Ser Gly Leu Gly Leu Gly Tyr Cys Gln Arg
                645                 650                 655

Val Met Arg Ser Phe Gly Gly Lys Val Glu Cys His Ser Lys Leu Gly
                660                 665                 670

Glu Phe Thr Glu Phe His Leu Tyr Phe Pro Val Val Pro Asn Ala Pro
            675                 680                 685

Lys Ala Asp Ala Leu Arg Thr Pro Tyr Phe Asn Asp Trp Lys Ser Asn
    690                 695                 700

Gln Ala Ala Thr Glu Asn Lys Thr Asn Val Asp Ala Lys Pro Asp Asn
            705                 710                 715                 720

Gln Ala Ala Thr Gln Asn Ser Glu Pro Thr Ser Thr Leu Thr Pro Gly
                725                 730                 735

Asn His Leu Ala Pro Thr Val Leu Ile Val Asp Asp Lys Glu Val Gln
                740                 745                 750

Arg Thr Leu Val Gln Met Tyr Leu Ser Arg Leu Gly Val Asn Ser Leu
            755                 760                 765

Gln Ala Lys Asn Gly Glu Asn Ala Val Glu Leu Phe Lys Thr His Lys
            770                 775                 780
```

```
Val Asp Leu Ile Leu Met Asp Val Gln Met Pro Ile Met Asn Gly Phe
785                 790                 795                 800

Asp Ala Ser Gln Ile Ile Lys Ala Arg Ser Pro Gln Thr Pro Ile Ile
            805                 810                 815

Ala Leu Ser Gly Glu Ser Gly Gln His Glu Leu Asp Met Ile Ser Lys
            820                 825                 830

Leu Met Asp Gly Arg Leu Glu Lys Pro Thr Ser Leu Lys Ala Leu Gln
            835                 840                 845

His Val Leu Asp Asn Trp Leu Glu Lys Gly Trp Ala Ser Asn Thr Ser
        850                 855                 860

Lys Glu Thr Glu Ser Glu Glu
865                 870

<210> SEQ ID NO 4
<211> LENGTH: 846
<212> TYPE: PRT
<213> ORGANISM: Vibrio alginolyticus

<400> SEQUENCE: 4

Met Leu Asp Val His Leu His Gly Leu Phe Tyr Pro Lys Ala Met Ala
1               5                   10                  15

Leu Tyr Ala Thr Val Leu Ile Val Phe Ala Trp Leu Leu Tyr Tyr Cys
            20                  25                  30

Tyr Arg Leu Lys Gln Lys Ser Glu Ser Ile Leu Gly Ser His His Ala
        35                  40                  45

Pro Tyr Ile Ala Tyr Ser Ser Cys Ile Ile Val Trp Ile Ser Ser Asn
    50                  55                  60

Ala Tyr Phe His Thr Asp Leu Leu Pro Glu Leu Gly Ser Val Gly Gly
65              70                  75                  80

Ile Phe Met Ala Lys Leu Ala Asn Leu Ala Ser Phe Ala Phe Ala
            85                  90                  95

Phe Ala Phe Tyr Phe Ser Cys Gln Leu Thr Ala Asp Val Lys Lys Thr
            100                 105                 110

Ala Val Lys Val Trp Gln Lys Val Phe Val Thr Leu Ala Thr Tyr
        115                 120                 125

Ser Leu Tyr Ile Asn Leu Val Pro Asn Leu Thr Val Glu Asn Val Thr
130                 135                 140

Ile Ser Gly Pro Ser Gln Phe Val Ile Glu Phe Gly Pro His Thr Ser
145                 150                 155                 160

Tyr Phe Phe Ile Ser Leu Leu Ala Phe Val Leu Thr Leu Leu Asn
            165                 170                 175

Leu Ile Ala Met Arg Ala Asn Ser Ser Lys Leu Thr Leu Ala Lys Ser
            180                 185                 190

Asn Tyr Met Ile Ala Gly Ile Leu Val Phe Met Leu Ser Thr Ala Val
        195                 200                 205

Ile His Leu Gly Met Thr Tyr Phe Leu Gly Asp Phe Ser Leu Thr Trp
    210                 215                 220

Leu Pro Pro Ala Leu Ser Ile Ser Glu Met Leu Phe Val Gly Tyr Ala
225                 230                 235                 240

Leu Leu Thr Ser Arg Phe Tyr Ser Ala Lys Tyr Leu Tyr Leu Thr
            245                 250                 255

Val Ser Ala Leu Leu Val Cys Ala Ile Phe Val Leu Pro Leu Gly Ala
            260                 265                 270

Ile Phe Ile Pro Ile Ser Glu Asp Asn Gln Trp Leu Val Ala Val Pro
```

```
                275                 280                 285
Leu Cys Ala Leu Ile Gly Ile Thr Trp His Leu Phe Lys Arg Val
290                 295                 300
Ser Arg Tyr Ala Ser Tyr Phe Ile Tyr Gly Lys Arg His Thr Pro Val
305                 310                 315                 320
Gln Gln Ile Leu Gly Leu Glu Glu Glu Phe Lys Arg Ser Ile Asp Asp
                325                 330                 335
Ala Met His Gln Leu Ala Ser Leu Leu Asn Ile Pro Asn Asn Lys Leu
                340                 345                 350
Gln Leu Val Thr Ser Asn Tyr Thr Glu Thr Phe Tyr Glu Glu Tyr Leu
                355                 360                 365
Pro Ser Ser Lys Ser Val Leu Val Leu Asp Glu Leu Ser Glu Glu Ile
370                 375                 380
Asp Tyr Ala Ser Ser Lys Gly Ser Met Arg Lys Leu Tyr Glu Arg
385                 390                 395                 400
Met Arg Ser Ser Asn Thr Ala Leu Val Met Pro Leu Phe Gly Arg Gly
                405                 410                 415
Lys Ser Val Thr His Leu Leu Ile Ser Ser His Lys Ile Asp Asn Lys
                420                 425                 430
Leu Phe Ser Asn Glu Glu Ile Ser Ala Leu Gln Thr Leu Leu Val Arg
                435                 440                 445
Ile Gln Ser Thr Ile Glu Ala Asp Arg Lys Val Arg Gln Ser Arg Ala
450                 455                 460
Leu Ala Asn Ser Ile Ala His Glu Met Arg Asn Pro Leu Ala Gln Val
465                 470                 475                 480
Gln Leu Gln Phe Glu Ala Leu Lys Gln His Ile Glu Ser Asn Ala Ser
                485                 490                 495
Leu Asp Thr Leu Lys Arg Glu Ile Asp Lys Gly Glu Ala Ala Ile Gln
                500                 505                 510
Arg Gly Arg Gln Leu Ile Asp Ile Ile Leu Arg Glu Val Ser Asp Ser
                515                 520                 525
Ser Pro Glu His Glu Pro Leu Ala Leu Thr Ser Ile His Lys Ala Ile
530                 535                 540
Asp Gln Ala Val Ser Arg Tyr Gly Phe Glu Asn Asp Gln Ile Ile Glu
545                 550                 555                 560
Arg Ile Asn Leu Pro Gln Ala His Asp Phe Val Ala Lys Leu Asn Glu
                565                 570                 575
Thr Leu Phe Asn Phe Val Ile Phe Asn Leu Ile Arg Asn Ala Ile Tyr
                580                 585                 590
Tyr Phe Asp Ser Tyr Pro Asp Ser Gln Ile Glu Ile Arg Thr Gln Thr
                595                 600                 605
Gly Ala Tyr Glu Asn Ile Leu Ile Phe Arg Asp Ser Gly Pro Gly Ile
                610                 615                 620
Asp Ser Ser Ile Leu His Lys Ile Phe Asp Asp Phe Ser Tyr Gln
625                 630                 635                 640
Lys Ser Gly Gly Ser Gly Leu Gly Leu Gly Tyr Cys Gln Arg Val Met
                645                 650                 655
Arg Ser Phe Gly Gly Arg Ile Glu Cys Gln Ser Glu Leu Asn Glu Phe
                660                 665                 670
Thr Glu Phe Tyr Leu Tyr Phe Pro Val Val Pro Asn Ala Pro Lys Pro
                675                 680                 685
Glu Thr Leu Arg Ala Pro Asp Phe Asp Ser Trp Lys Ala Thr Pro Ser
                690                 695                 700
```

```
His Ser Glu Asn His Ser Ala Gln His Val Gln Val Cys Lys Asp Ala
705                 710                 715                 720

Pro Thr Val Leu Ile Val Asp Asp Lys Glu Val Gln Arg Thr Leu Val
                725                 730                 735

Gln Met Tyr Leu Lys Arg Leu Gly Val Asn Ser Leu Gln Ala Asn Asn
            740                 745                 750

Gly Ala Ser Ala Val Glu Leu Phe His Ser His Lys Ile Asp Leu Val
        755                 760                 765

Leu Met Asp Val Gln Met Pro Val Met Asn Gly Phe Asp Ala Ser Gln
    770                 775                 780

Arg Ile Lys Gln Ile Thr Ser Ser Val Pro Ile Ile Ala Leu Ser Gly
785                 790                 795                 800

Glu Ser Gly Ala Arg Glu Leu Glu Leu Ile Ser Lys Leu Met Asp Asp
                805                 810                 815

Arg Leu Glu Lys Pro Thr Thr Leu Asn Ala Leu Gln Val Val Ile Gln
            820                 825                 830

Arg Trp Leu Gln Asn Glu Asn Phe Ala Pro Ser Asn Thr Phe
        835                 840                 845

<210> SEQ ID NO 5
<211> LENGTH: 859
<212> TYPE: PRT
<213> ORGANISM: Listonella anguillarum

<400> SEQUENCE: 5

Met Leu Asn Leu Asn Leu Asp Pro Ile Leu Tyr Pro Lys Ala Ile Thr
1               5                   10                  15

Leu Ile Ala Ala Val Ala Met Val Leu Val Trp Leu Thr Tyr Tyr Cys
            20                  25                  30

Tyr Arg Leu Lys Gln Lys Asn Glu Val Ile Phe Gly Thr His His Ala
        35                  40                  45

Ser Tyr Ile Ala Tyr Ser Ser Cys Ile Ile Ala Trp Ile Gly Ser Asn
    50                  55                  60

Ala Tyr Phe His Thr Asp Trp Leu Val Glu Leu Gly Val Asn Arg Ala
65                  70                  75                  80

Ile Phe Met Ala Glu Ile Ala Asn Ile Ser Ala Ser Leu Ala Phe Val
                85                  90                  95

Phe Ala Tyr Tyr Phe Ser Cys Gln Leu Ser Ala Glu Gln Arg Lys Gly
            100                 105                 110

Lys Val His Leu Trp Gln Arg Leu Ile Phe Ile Thr Ile Ala Ala Tyr
        115                 120                 125

Ser Val Leu Ile Asn Leu Gln Ser Asn Leu Thr Val Lys His Val Asp
    130                 135                 140

Ile Val Gly Pro Ser Glu Phe Val Ile Glu Phe Gly Pro His Thr Pro
145                 150                 155                 160

Tyr Phe Phe Asn Ala Met Leu Cys Ser Val Ile Leu Thr Leu Phe Asn
                165                 170                 175

Leu Val Val Met Arg Thr Asn Ser Ser Lys Leu Ala Leu Ala Lys Thr
            180                 185                 190

Asn Tyr Ile Ile Ala Gly Ile Leu Val Tyr Met Leu Ser Thr Leu Val
        195                 200                 205

Ile His Ile Gly Ile Thr Phe Phe Phe Gln Asp Phe Ser Leu Ser Trp
    210                 215                 220

Leu Pro Pro Ala Leu Ser Ile Ser Glu Met Met Phe Val Gly Tyr Ala
```

-continued

```
            225                 230                 235                 240
Leu Ile Thr Ser Arg Phe Tyr Ser Val Lys Tyr Leu Ala Tyr Leu Cys
                245                 250                 255
Leu Asn Thr Ala Leu Val Cys Gly Val Leu Phe Ile Pro Leu Gly Ala
                260                 265                 270
Ile Phe Ile Pro Leu Thr Asp Ser Asn Gln Trp Leu Ile Ala Ile Pro
                275                 280                 285
Leu Cys Ala Leu Ile Gly Ile Thr Trp Asn Pro Leu Tyr Lys Arg Leu
                290                 295                 300
Ser Arg Tyr Ala Ser Leu Leu Ile Tyr Gly Asn Gln Gln Thr Pro Val
305                 310                 315                 320
Glu Gln Ile Leu Ala Leu Glu Asp Asp Phe Lys Arg Ser Ile Asp Asp
                325                 330                 335
Ala Met Arg Arg Leu Gly Gln Leu Leu Tyr Ile Ala Asp Asp Lys Leu
                340                 345                 350
Gln Phe Val Asn Ser Asn Tyr Asn Glu Thr Val Tyr Glu Arg Tyr Leu
                355                 360                 365
Ser Ser Lys Gln Thr Ala Leu Val Phe Asp Glu Leu Phe Glu Lys Leu
370                 375                 380
Asp Asn Lys Thr Ala Ala Lys Asn Ser Ile Lys Ala Leu Tyr Asp Lys
385                 390                 395                 400
Met Ser Ser Asn Asn Thr Ala Leu Val Met Pro Leu Phe Gly His Ser
                405                 410                 415
Lys Leu Val Thr His Leu Leu Ile Ser Pro His Lys Ile Asn Asn Gln
                420                 425                 430
Met Phe Ser Asn Glu Glu Ile Ala Ala Leu Gln Thr Leu Leu Thr Arg
                435                 440                 445
Ile Gln Ser Ile Ile Glu Ala Asp Arg Arg Val Cys Gln Ser Arg Ala
                450                 455                 460
Leu Ala Asn Ser Ile Ala His Glu Met Arg Asn Pro Leu Ala Gln Val
465                 470                 475                 480
Gln Leu His Phe Glu Ile Leu Lys Gln His Ile Asp Ser Gln Ala Pro
                485                 490                 495
Ala Gln Gln Ile Lys Gln Asp Ile Glu Asn Gly Gln Ala Ala Ile Gln
                500                 505                 510
Arg Gly Arg Gln Leu Ile Asp Ile Ile Leu Arg Glu Val Ser Asp Ser
                515                 520                 525
Ser Pro Glu His Glu Pro Ile Thr Met Thr Ser Ile His Lys Ala Val
                530                 535                 540
Asp Gln Ala Val Ser Gln Tyr Gly Phe Glu Asn Glu Lys Val Ile Glu
545                 550                 555                 560
Arg Ile His Leu Pro Gln Gln Asp Phe Val Ala Lys Leu Asn Glu
                565                 570                 575
Thr Leu Phe Asn Phe Val Ile Phe Asn Leu Ile Arg Asn Ala Ile Tyr
                580                 585                 590
Tyr Phe Asp Ser Tyr Pro Asn Ser Gln Ile Glu Ile Thr Thr Gln Ile
                595                 600                 605
Gly Thr Tyr Glu Asn Ile Leu Ile Phe Arg Asp Thr Gly Pro Gly Ile
                610                 615                 620
Asp Asp Ala Ile Ser Tyr Lys Ile Phe Asp Asp Phe Ser Tyr Gln
625                 630                 635                 640
Lys Ser Gly Gly Ser Gly Leu Gly Leu Gly Tyr Cys Gln Arg Val Met
                645                 650                 655
```

```
Arg Ser Phe Gly Gly Arg Val Glu Cys Lys Ser Lys Leu Gly Glu Phe
            660             665             670

Thr Glu Phe His Leu Tyr Phe Pro Met Val Pro Asn Ala Pro Gln Ala
            675             680             685

Asp Ser Leu Arg Thr Pro Asp Phe Lys Ser Trp Gln Gln Pro Lys Pro
690             695             700

Asn Thr Glu Gln Arg Thr Val Asp Asn Ile Gln Pro Ile Asp Lys Pro
705             710             715             720

Phe Leu Ile Asn Asn Lys Ala Pro Thr Val Leu Ile Val Asp Asp Lys
            725             730             735

Glu Val Gln Arg Ser Leu Val Gln Met Tyr Leu Asn Gln Leu Gly Val
            740             745             750

Asn Asn Leu Gln Ala Asn Asn Gly Glu Asn Ala Val Glu Ile Phe Lys
            755             760             765

Ala Asn Ser Ile Asp Leu Ile Leu Met Asp Ile Gln Met Pro Val Met
            770             775             780

Asn Gly Phe Glu Ala Ser Gln Ile Ile Lys Ala His Ser Pro Gln Val
785             790             795             800

Pro Ile Ile Ala Leu Ser Gly Glu Ser Gly Glu Arg Glu Leu Glu Met
            805             810             815

Ile Ser Lys Leu Met Asp Gly Arg Leu Glu Lys Pro Thr Ser Leu Asn
            820             825             830

Ala Leu Gln Gln Val Ile Ser His Trp Leu Asn Lys Asp Ile Val Pro
            835             840             845

Asn Ala His Thr Ala Lys Ser Gly Thr Val Ile
            850             855

<210> SEQ ID NO 6
<211> LENGTH: 885
<212> TYPE: PRT
<213> ORGANISM: Vibrio sp.

<400> SEQUENCE: 6

Met Lys Thr Phe Asp Leu Gly Leu Glu Ala Ile Phe Tyr Ala Lys Ala
1               5                   10                  15

Ile Thr Leu Leu Ala Thr Val Ala Val Val Met Trp Leu Phe Tyr
            20                  25                  30

Tyr Cys Tyr Arg Leu Lys Gln Lys Asn Glu Ala Ile Val Gly Thr His
            35                  40                  45

His Val Pro Tyr Ile Ala Tyr Ser Ile Cys Ile Thr Trp Ile Ser
        50                  55                  60

Ser Asn Ala Tyr Phe His Thr Gly Leu Leu Pro Gly Leu Gly Thr Thr
65              70                  75                  80

Ala Ala Ile Phe Ala Ala Lys Leu Ala Asn Leu Ser Ser Phe Leu Ala
                85                  90                  95

Phe Ala Phe Ala Tyr Tyr Phe Ser Cys Gln Leu Ala Ala Glu Asn Arg
            100                 105                 110

Ser Gly Lys Ile His Arg Trp Gln Lys Thr Ile Leu Ala Ser Ile Thr
            115                 120                 125

Gly Tyr Ser Phe Tyr Ile Asn Leu Thr Pro Gly Leu Thr Val Glu Asp
            130                 135                 140

Val Thr Ile Thr Ala Pro Ser Gln Phe Val Glu Phe Gly Pro His
145             150                 155                 160

Thr Pro Tyr Phe Phe Ile Gly Val Ile Ser Leu Ile Ala Leu Thr Leu
```

-continued

```
                165                 170                 175
Thr Asn Leu Val Thr Met Arg Ala Asn Ser Ser Lys Leu Thr Leu Ala
                180                 185                 190
Lys Thr Asn Tyr Met Ile Thr Gly Ile Leu Val Phe Met Leu Ser Thr
                195                 200                 205
Ala Thr Ile His Ile Gly Val Ala Tyr Phe Leu Arg Asp Phe Ser Leu
                210                 215                 220
Thr Trp Leu Pro Pro Ala Leu Ser Leu Ser Glu Met Leu Phe Val Gly
225                 230                 235                 240
Tyr Ala Leu Leu Thr Ser Arg Phe Tyr Ser Phe Lys Tyr Leu Thr Tyr
                245                 250                 255
Ile Ser Leu Asn Val Leu Leu Val Cys Ala Ile Leu Val Ile Pro Phe
                260                 265                 270
Cys Thr Val Phe Ile Pro Leu Thr Asp Gly Asn Gln Trp Leu Leu Ala
                275                 280                 285
Ile Pro Ile Cys Ala Ile Ile Gly Ile Thr Trp Ser Pro Ile Tyr Lys
                290                 295                 300
Arg Val Ser Pro Tyr Ser Ser Leu Leu Val Tyr Arg Asn Lys Lys Thr
305                 310                 315                 320
Pro Val Gln Gln Ile Leu Ala Leu Glu Glu Gly Phe Lys Leu Ser Ile
                325                 330                 335
Asp Asp Ala Met Arg Arg Leu Gly Arg Gln Leu Gln Ile Pro Glu Asp
                340                 345                 350
Lys Leu Arg Leu Val Asn Asn Tyr Asn Glu Thr Phe Tyr Glu Asp
                355                 360                 365
Tyr Leu Ser Ser Lys Glu Ser Val Leu Val Phe Asp Glu Leu Ser Glu
                370                 375                 380
Glu Leu Asp Asp Thr Ala Leu Ala Lys Arg Ser Leu Lys Ala Leu Tyr
385                 390                 395                 400
Asp Lys Met Ser Ser Asn Asn Thr Ala Leu Val Met Pro Leu Phe Gly
                405                 410                 415
His Lys Lys Ser Val Thr His Leu Leu Val Ser Ser His Lys Ser Asn
                420                 425                 430
Asn Arg Met Phe Ser Asn Glu Glu Ile Ser Ala Leu Gln Thr Leu Leu
                435                 440                 445
Thr Arg Val Gln Ser Thr Ile Glu Ala Asp Arg Arg Ile Arg Gln Ser
                450                 455                 460
Arg Ala Leu Ala Asn Ser Ile Ala His Glu Met Arg Asn Pro Leu Ala
465                 470                 475                 480
Gln Val Gln Leu His Phe Glu Val Leu Lys Gln His Ile Asp Asn Gln
                485                 490                 495
Ala Pro Thr Gln Gln Ile Leu Thr Asp Ile Glu Asn Gly Gln Ala Ala
                500                 505                 510
Ile Gln Arg Gly Arg Gln Leu Ile Asp Ile Leu Arg Glu Val Ser
                515                 520                 525
Asp Ser Ser Pro Glu His Gly Pro Ile Thr Met Thr Ser Ile His Lys
                530                 535                 540
Ala Val Asp Gln Ala Val Ser His Tyr Gly Phe Glu Asn Glu Lys Ile
545                 550                 555                 560
Ile Glu Arg Ile Arg Leu Pro Gln His Ala Asp Phe Val Ala Lys Leu
                565                 570                 575
Asn Glu Thr Leu Phe Asn Phe Val Ile Phe Asn Leu Ile Arg Asn Ala
                580                 585                 590
```

```
Ile Tyr Tyr Phe Asp Ser Tyr Pro Asp Ser Gln Ile Glu Ile Ser Thr
            595                 600                 605

Lys Thr Gly Ser Tyr Glu Asn Val Leu Thr Phe Arg Asp Thr Gly Pro
    610                 615                 620

Gly Ile Asp Glu Ala Ile Val His Lys Val Phe Asp Asp Phe Phe Ser
625                 630                 635                 640

Phe Gln Lys Ser Gly Gly Ser Gly Leu Gly Leu Gly Tyr Cys Gln Arg
                645                 650                 655

Val Met Arg Ser Phe Gly Gly Arg Val Glu Cys His Ser Lys Leu Gly
            660                 665                 670

Glu Phe Thr Glu Phe His Leu Tyr Phe Pro Ile Val Pro Asn Ala Pro
    675                 680                 685

Lys Ala Glu Thr Leu Arg Thr Pro Tyr Phe Asn Gly Trp Lys His Asn
690                 695                 700

Gln Ser Thr Glu Asp Lys Ala Glu Ala Asp Val Lys Pro Glu Ser Gln
705                 710                 715                 720

Thr Pro Ser Gly Asp Ile Glu Pro Pro Ala Ser Thr Leu Thr Glu
                725                 730                 735

Ser Lys Gln Thr Glu Arg Thr Gln Ala Glu Asn Gln Pro Ala Ser Ser
            740                 745                 750

His Leu Ala Pro Thr Val Leu Ile Val Asp Asp Lys Glu Val Gln Arg
    755                 760                 765

Thr Leu Val Gln Met Tyr Leu Ser Arg Leu Gly Val Asn Ser Leu Gln
770                 775                 780

Ala Lys Asn Gly Glu Asn Ala Val Glu Leu Phe Arg Ser His Lys Val
785                 790                 795                 800

Asp Leu Ile Leu Met Asp Val Gln Met Pro Ile Met Asn Gly Phe Asp
                805                 810                 815

Ala Ser Gln Ile Ile Lys Ala Arg Ser Pro Gln Thr Pro Ile Ile Ala
            820                 825                 830

Leu Ser Gly Glu Ser Gly Gln Arg Glu Leu Asp Met Ile Arg Lys Leu
    835                 840                 845

Met Asp Gly Arg Leu Glu Lys Pro Thr Ser Leu Asn Ala Leu Gln His
850                 855                 860

Leu Leu Asp Asn Trp Leu Glu Lys Gly Trp Ala Pro Asn Ala Ser Lys
865                 870                 875                 880

Glu Thr Glu Asn Glu
                885

<210> SEQ ID NO 7
<211> LENGTH: 960
<212> TYPE: PRT
<213> ORGANISM: Photobacterium profundum

<400> SEQUENCE: 7

Met His Asp Phe Ile Gln Ser Thr Leu Ala Asn Met Val Ala Ile Phe
1               5                   10                  15

Leu Val Ala Ile Ala Leu Val Val Ile Trp Ala Thr Tyr Phe Ala
            20                  25                  30

Arg Ile Leu Ala Lys His Leu Pro Gly Ser Ser Arg Gln Val Tyr Phe
        35                  40                  45

Pro Tyr Thr Leu Tyr Ser Val Phe Ile Ser Ala Trp Ile Leu Ser Asn
    50                  55                  60

Ala Tyr Phe Gln Ser Asp Leu Leu Val Tyr Phe Gly Ala Asp Thr Ala
```

-continued

```
             65                  70                  75                  80
    Ile Ile Met Ala Leu Leu Ala Asn Ile Phe Ser Gly Leu Ala Phe Ala
                     85                  90                  95
    Tyr Ala Phe Leu Phe Ser Cys Arg Leu Val Ser Glu Arg Thr Ser Phe
                    100                 105                 110
    Gln Leu Lys Thr Trp Gln Trp Ile Leu Phe Ser Leu Thr Cys Ile Ile
                    115                 120                 125
    Ile Leu Val Thr Asn Cys Val Pro Gly Leu Asn Val Lys Ser Val Asp
                    130                 135                 140
    Ile Glu Gly Ile Gly Ser Phe Val Ile His Phe Gly Pro Thr Ile Gly
    145                 150                 155                 160
    Val Phe Phe Gly Asn Leu Leu Leu Leu Ile Leu Thr Leu Gly Asn
                        165                 170                 175
    Phe Ile Leu Ser Ser Arg Ser Gln Leu Lys Leu Lys Gln Ile Lys Ala
                    180                 185                 190
    Asn Tyr Met Ile Phe Gly Met Met Ala Phe Ile Ser Thr Phe Phe
                195                 200                 205
    Ala His Phe Leu Ile Pro Ile Phe Leu Asn Asp Phe Ser Lys Ala Trp
                210                 215                 220
    Leu Pro Pro Ala Leu Ser Ile Ile Glu Val Ile Val Gly Tyr Ala
    225                 230                 235                 240
    Leu Leu His His Arg Phe Tyr Ser Ile Arg Tyr Ile Gly Leu Ile Thr
                    245                 250                 255
    Leu Ser Phe Val Ile Asn Ala Ala Ile Tyr Ile Ile Pro Ile Ala Ser
                260                 265                 270
    Val Gly Phe Val Gly Thr Gln Asp Ser Thr Leu Leu Val Ile Trp
                275                 280                 285
    Thr Leu Ile Thr Gly Ile Cys Trp Tyr Lys Ser Leu Ala Ile Ile Arg
            290                 295                 300
    Arg Ser Val Asn Arg Leu Leu Tyr Lys Glu Lys Gly Asp Pro Val Glu
    305                 310                 315                 320
    Asn Ile Cys Asn Leu Ile Gly Glu Phe Ser Tyr Ser Thr Asp Gln Ala
                    325                 330                 335
    Val Ile Lys Leu Asn Gln Val Leu Asn Ala Lys Ser Gly Arg Ile Gln
                340                 345                 350
    Lys Val Ser Gly Asn Thr Glu Asn Asn Ile Phe Val Ser Tyr Phe His
            355                 360                 365
    Gly Asn Arg Ser Val Leu Ile Lys Glu Glu Ile Glu Tyr Gln Leu Lys
        370                 375                 380
    His Glu Lys Pro Glu Gly Thr Lys Glu Leu Ser Asn Val Thr Arg Glu
    385                 390                 395                 400
    Met Val Asn Met Gly Val Ser Leu Val Leu Pro Ile Thr Asn Glu Arg
                    405                 410                 415
    Asn Glu Val Thr Gln Leu Tyr Met Val Ser Lys Glu Lys Glu Asn Val
                420                 425                 430
    Leu Phe Ser Ser Glu Glu Ile Met Gly Leu Gln Leu Leu Phe Asp Lys
                435                 440                 445
    Ala Asn Cys Phe Ile Val Thr Glu Asp Lys Ile Arg Lys Ser Gln Val
                450                 455                 460
    Leu Val Gly Thr Ile Ala His Glu Ile Arg Asn Pro Leu Thr Lys Ile
    465                 470                 475                 480
    Lys Tyr His Phe Glu Arg Ile Asp Ala Asp Met Phe Gly Ile Glu Asn
                    485                 490                 495
```

```
Thr Ser Leu Ser Pro Phe Ala Ser Lys Glu Met Lys Ile Tyr Gln
            500                 505                 510

Glu Leu Ser Glu Gly Gln Lys Ala Val Gln Leu Gly Ser Arg Phe Ile
            515                 520                 525

Asp Ala Ile Leu Asp Glu Leu Arg Gly Glu Ser Ile Gly Thr Thr Leu
            530                 535                 540

Phe Asp Asn Tyr Ser Val Ala Lys Leu Thr His Gln Ala Leu Asn Asp
545                 550                 555                 560

Phe Cys Phe Asn Ser Glu His Lys Leu Arg Ile Asn Ile Asp Thr
                565                 570                 575

Gln Ser Asp Phe Phe His Gly Ser Asp Thr Leu Tyr Ser Phe Val
            580                 585                 590

Leu Phe Asn Leu Ile Lys Asn Ala Val Tyr Tyr Phe Asp Thr Tyr Pro
            595                 600                 605

Asn Ser Gln Ile Arg Ile Tyr Phe Gln Lys Glu Arg Asn Tyr Asn Lys
            610                 615                 620

Val His Val Val Asp Thr Gly Pro Gly Ile Ser Pro Asp His Gln Lys
625                 630                 635                 640

His Ile Leu Glu Glu Phe Tyr Thr Asn Gly Lys Val Gln Gly Asn Gly
                645                 650                 655

Leu Gly Leu Ser Tyr Cys Lys Arg Val Ile Glu Ser Phe Gly Gly Thr
            660                 665                 670

Ile Thr Cys Gln Ser Glu Leu Gly Glu Tyr Thr Glu Phe Ile Leu Ser
        675                 680                 685

Phe Pro Ser Ile Asp Glu Lys Ile His Ser Glu Met Ser Lys Glu Lys
    690                 695                 700

Ile Lys Ser Tyr Leu Thr Gly Met Ser Gly Leu Val Leu Gly Ser Val
705                 710                 715                 720

Glu Val Gly Asn Trp Leu Ser Ser Glu Phe Lys Ser Leu Gly Val Glu
                725                 730                 735

Leu Cys Thr Ala Pro Asp Val Lys Thr Gly Leu His His Leu Ser Gln
            740                 745                 750

Gln Ala Val Asp Phe Ile Ile Met Asp His Met Leu Leu Asn Arg Glu
        755                 760                 765

Met Gly Ser Ile Lys Met Leu Arg Ala Gly Thr His Gly His Gln Ala
    770                 775                 780

Gln Thr Thr Pro Met Phe Leu Tyr Gly Tyr Thr Glu Asn Ser Glu His
785                 790                 795                 800

Leu Asn Ser Ile Glu Leu Ser Pro Phe Phe Gln Gly Gln Ile Asp Gly
                805                 810                 815

Ile Asn Asp His Gln Ala Phe Leu His Ser Leu Glu Ser Leu Ile Asp
            820                 825                 830

Asn Asp Leu Phe Ala Lys Leu Gly Ser Leu Ile Gly Lys Thr Val Leu
        835                 840                 845

Val Val Asp Asp Met Gln Val Asn Arg Met Leu Val Gln Ala Tyr Leu
    850                 855                 860

Ala Ser Glu Gly Ile Thr Val Val Gln Ala Ser Ser Gly Asp Glu Ala
865                 870                 875                 880

Ile Glu Lys Val Lys Lys Glu Pro Phe Asn Leu Val Leu Met Asp Ile
                885                 890                 895

Gln Met Pro Gly Met Ser Gly Ile Glu Ala Thr His Gln Ile Arg His
            900                 905                 910
```

-continued

```
Leu Phe Asp Ala Ile Pro Ile Val Ala Leu Ser Gly Glu Tyr Asn Glu
            915                 920                 925

Glu Ile Thr Arg Ala Ile Ser Glu Thr Met Asn Asp His Leu Val Lys
            930                 935                 940

Pro Ile Asn Lys Gln Gln Leu Leu Gln Thr Leu Thr Lys Trp Met Thr
945                 950                 955                 960

<210> SEQ ID NO 8
<211> LENGTH: 976
<212> TYPE: PRT
<213> ORGANISM: Photobacterium phosphoreum

<400> SEQUENCE: 8

Met Pro Asp Leu Pro Leu Leu Phe Ser Glu Pro Arg Gly Ala Leu
1               5                   10                  15

Leu Phe Phe Ala Ala Gly Ile Ile Leu Ala Trp Leu Gly Tyr Phe Ser
            20                  25                  30

Phe Thr Leu Phe Thr Ser Arg Pro Gly Ala Asn Arg Asn Val Tyr Tyr
        35                  40                  45

Pro Tyr Leu Ala Tyr Ser Val Ser Ile Phe Leu Trp Ile Leu Ser Asn
    50                  55                  60

Ala Tyr Phe Gln Ser Pro Leu Leu Thr Tyr Tyr Ser Glu Ser Thr Ala
65                  70                  75                  80

Val Thr Met Ala Leu Phe Ala Asn Leu Val Ser Phe Cys Ala Phe Ile
                85                  90                  95

Ser Ala Tyr Ser Phe Ser Cys Arg Leu Ile Ser Thr Gln Pro Asp Ser
            100                 105                 110

Asn Leu Ser Leu Tyr Gln Lys Leu Phe Ile Ser Ile Ser Leu Tyr
        115                 120                 125

Ala Leu Ile Ile Asn Ser Ser Pro Gly Leu Thr Val Lys His Val Asp
    130                 135                 140

Ile Val Ala Pro Gly Asp Phe Val Ile Phe Gly Pro Gln Thr Ser
145                 150                 155                 160

Trp Phe Phe Leu Cys Leu Met Ser Ala Val Phe Leu Thr Phe His Asn
                165                 170                 175

Phe Leu Ile Tyr Lys Lys Ala Gly Ser Pro Leu Ile Gln Lys Lys Ser
            180                 185                 190

Gln Tyr Met Ile Leu Gly Val Ile Ile Phe Met Leu Ser Thr Leu Ile
        195                 200                 205

Val His Leu Ile Ile Pro Phe Met Leu Asp Asp Phe Ser Leu Thr Trp
    210                 215                 220

Val Pro Pro Ala Leu Ala Ile Phe Glu Thr Leu Leu Ile Gly Tyr Ala
225                 230                 235                 240

Leu Leu Phe Asn Arg Phe Tyr Ser Pro Arg Tyr Ile Ile Ser Gln Phe
                245                 250                 255

Ile Ser His Leu Val Asn Val Thr Leu Tyr Leu Ser Pro Tyr Leu Leu
            260                 265                 270

Ile Ile Ala Ile Gly Tyr Glu Asp Asn Pro Leu Leu Ile Gly Leu Trp
        275                 280                 285

Ile Ala Leu Ile Gly Leu Gly Trp Lys Ser Ser Leu Ile Gln Ile Lys
    290                 295                 300

Arg Gly Thr Asn Arg Leu Leu Tyr Gly Lys Asn Gly Ser Pro Ser Glu
305                 310                 315                 320

Asn Ile Gln Arg Val Ile Gly His Phe Gln Tyr Ser Thr Glu Tyr Gly
                325                 330                 335
```

```
Leu Gly Lys Leu Asn Glu Leu Leu Asn Thr Arg Ser Gly Gln Ile Leu
            340                 345                 350

Asn Ile Asn Thr His Ser Asp Leu Ala Ala Leu Lys Ile Tyr Phe Glu
            355                 360                 365

Gly Lys His Ser Val Leu Val Lys Asp Glu Leu Glu Phe Gln Ile Gln
            370                 375                 380

Tyr Glu Thr His Thr Glu Leu Ser Asn Ile Ser Trp Leu Lys Lys Asn
385                 390                 395                 400

Met Asp Ala Asn Asn Ser Ala Leu Val Leu Pro Ile Val Ser Lys Asn
                405                 410                 415

Gly Asp Ile Ser His Leu Phe Met Val Ser Lys Lys Asp Arg Asp Gly
            420                 425                 430

Leu Phe Ser Ser Glu Glu Ile Asp Ala Leu Gln Val Leu Phe Glu Gln
            435                 440                 445

Ala Asn Gln Tyr Ile Arg Ser Glu Glu Gln Val Arg Lys Ser Gln Val
            450                 455                 460

Leu Ala Gly Ser Ile Ala His Glu Ile Arg Asn Pro Leu Ser Lys Ile
465                 470                 475                 480

Gln Tyr His Phe Glu Arg Ile Asp Ala Asp Leu Phe Asp Val Asn Asn
                485                 490                 495

Asn Ser Ala His Pro Phe Leu Ser Glu Gln Met Lys Gly Leu Tyr Lys
            500                 505                 510

Glu Leu Thr Glu Ser Lys Lys Ala Val Gln Leu Gly Thr Arg Phe Ile
            515                 520                 525

Asp Ile Ile Asp Glu Ile Lys Gly Asn Ser Ile Asn Ser Gln Thr
            530                 535                 540

Phe Ser Ser His Ser Ala Gly Arg Leu Thr Glu Gln Ala Leu Ser Glu
545                 550                 555                 560

Tyr Gly Phe Val Gly Asn Thr Tyr Gln Ala Arg Ile Ile Ala Asn Thr
                565                 570                 575

Gln Asn Asp Phe Gln Phe Trp Gly Asn Glu Thr Leu Phe Ser Phe Val
            580                 585                 590

Met Phe Asn Leu Val Lys Asn Ala Leu His Tyr Phe Ser Gln Tyr Pro
            595                 600                 605

Gln Ser Thr Leu Ser Ile His Leu Glu Arg Gly Glu Ser Glu Asn Cys
            610                 615                 620

Ile Ile Val Thr Asp Thr Gly Pro Gly Ile Ala Asp Asn Val Ile Pro
625                 630                 635                 640

His Ile Phe Asp Glu Phe Tyr Thr Leu Gly Lys Ser Asp Gly Ser Gly
                645                 650                 655

Leu Gly Leu Ala Tyr Cys Arg Arg Val Ile Asn Ala Phe Gly Gly Asn
            660                 665                 670

Ile His Cys Gln Ser Lys Tyr Gly Ser Tyr Thr Arg Phe Thr Leu Thr
            675                 680                 685

Phe Pro Ile Ile Asn Glu Glu Arg Ile Pro Asn Asn Leu Phe Asn Glu
            690                 695                 700

Leu Lys Glu Ala Leu Thr Gly Lys Gln Val Leu Val Ile Gly His Lys
705                 710                 715                 720

Glu Asn Thr Thr Leu Ile Ser Ser Leu Leu Ser Gly Phe Asn Ile Ile
                725                 730                 735

Val Ser Thr Val Asp Asn Gly Lys Ser Ala Ala Lys Tyr Ile Gly Asn
            740                 745                 750
```

```
Asn Asn Val Asp Phe Ala Phe Tyr Asp Leu Ser Leu Ser Pro Thr Gln
            755                 760                 765

Phe Glu Ala Leu Lys Lys Ile Arg Ser Gly Asp Phe Gly Ala Asn Ala
770                 775                 780

Gln Lys Ile Pro Leu Ile Ala Leu Ser Asn Glu Asn Thr Arg Ser Thr
785                 790                 795                 800

Arg Phe Asp Thr Asn Val Phe Gln Gly Glu Phe Arg Ile Ser Asp Ser
                805                 810                 815

Leu Pro Leu Phe Ala Gln Ser Leu Lys Leu Leu Ile Asp Ser Gly Ser
                820                 825                 830

Leu Lys Pro Leu Gly His Leu Ile Gly Lys Arg Val Leu Val Val Asp
            835                 840                 845

Asp Met Gln Ile Asn Arg Met Leu Val Gln Ser Tyr Leu Ala Gln Glu
850                 855                 860

Gly Ile Thr Val Leu Gln Ala His Asn Gly Ser Val Ala Leu Cys Ile
865                 870                 875                 880

Ala Glu Gln Glu Arg Pro Asp Leu Ile Leu Met Asp Ile His Met Pro
                885                 890                 895

Glu Met Asp Gly Leu Glu Val Ser Arg Ile Leu Arg Gln Arg Gly Tyr
                900                 905                 910

Asn Ile Pro Ile Ile Ala Leu Ser Gly Glu Cys Cys Asn Glu Val Thr
            915                 920                 925

Lys Glu Ile Ser Gln Tyr Met Asn Ala Tyr Leu Met Lys Pro Ile Thr
930                 935                 940

Arg Gln Gln Leu Ile Gln Lys Leu Gln Tyr Trp Ile Pro Glu Ser Glu
945                 950                 955                 960

Ala Asp Lys Val Ile Ser Lys Gln Asp Ile His Ile Val His Ser Ile
                965                 970                 975

<210> SEQ ID NO 9
<211> LENGTH: 820
<212> TYPE: PRT
<213> ORGANISM: Vibrio fischeri

<400> SEQUENCE: 9

Met Leu Thr Thr Leu Ser Lys Val Tyr Leu Leu Thr Thr Ser Ala
1               5                   10                  15

Ile Ile Leu Leu Trp Val Gly Tyr Phe Val Arg Ser Leu Tyr Lys Glu
            20                  25                  30

Arg Thr Lys Val Asn Pro Tyr Ile Tyr Ser Ser Tyr Ile Phe Tyr Ala
        35                  40                  45

Leu Phe Ile Ile Leu Trp Ile Leu Ser Asn Ala Tyr Phe Gln Ser Pro
50                  55                  60

Leu Leu Thr Tyr Phe Asp Glu Ser Ala Ala Ile Phe Met Ala Leu Phe
65                  70                  75                  80

Ala Asn Met Thr Ser Tyr Leu Ala Phe Ala Phe Ala Phe Leu Phe Ser
                85                  90                  95

Cys Arg Leu Ala Ser Lys His Pro Asp Lys Arg Leu Ser Lys Trp Gln
            100                 105                 110

Phe Gly Leu Thr Ser Ile Thr Thr Phe Ala Ala Leu Ile Val Asn Val
        115                 120                 125

Ile Pro Asn Leu Thr Val Ile Gly Val Thr Ile Gln Ala Pro Ser Val
130                 135                 140

Phe Thr Ile Glu Phe Gly Pro Phe Ala Pro Leu Phe Phe Leu Asn Ala
145                 150                 155                 160
```

-continued

```
Phe Leu Phe Val Ile Leu Thr Ser Ile Asn Phe Phe Lys Leu Arg Lys
                165                 170                 175

Ser Asn Ile Lys Leu Asn Lys Glu Lys Ser Ile Tyr Leu Met Val Gly
            180                 185                 190

Ile Phe Ile Tyr Met Ile Ser Thr Ile Ala Ser Gln Ile Ile Ile Pro
        195                 200                 205

Val Ile Trp Ala Asp Phe Ser Tyr Thr Trp Val Pro Pro Ala Leu Ser
    210                 215                 220

Val Thr Glu Ala Leu Leu Ile Gly Tyr Thr Leu Leu Tyr His Arg Leu
225                 230                 235                 240

Tyr Ser Phe Lys Tyr Leu Leu Phe Trp Ser Leu Ser Tyr Ser Ile Asn
                245                 250                 255

Leu Ile Leu Tyr Leu Ile Pro Ile Ile Ile Tyr Asp Leu Thr Thr
            260                 265                 270

Pro Ser Asp Leu Leu Tyr Ile Cys Ile Ile Glu Ile Phe Thr Gly
        275                 280                 285

Leu Phe Trp Asp Lys Thr Leu Lys Lys Thr Lys Lys Ile Ala Ser Ile
    290                 295                 300

Ile Ile Tyr Lys Asp Lys Gln Thr Pro Val Glu Lys Ile Tyr Lys Ile
305                 310                 315                 320

Ala Glu Glu Phe Lys Tyr Ser Ser Ser Asn Ala Ile Ile Lys Leu Ala
                325                 330                 335

Ser Ile Leu Asn Thr Pro Lys Glu Glu Leu Leu Leu Ile Gly Lys Asn
            340                 345                 350

Thr Asn Tyr Asn Ile Phe Ile Pro His Leu Asn Gln Ser His Ser Ala
        355                 360                 365

Leu Val Lys Asp Glu Leu Asp Tyr Gln Ile His Tyr Ser Pro Lys Thr
    370                 375                 380

Ala Asn Ala Glu Leu His Gln Val Gln Glu Lys Met Ser Glu Ser Lys
385                 390                 395                 400

Thr Ala Leu Ile Leu Pro Ile Phe Gly Glu Asn Lys Leu Ile Ser His
                405                 410                 415

Phe Leu Ile Ser Ala Asn Lys His Asp Asn Thr Thr Phe Ser Asn Glu
            420                 425                 430

Glu Ile Ser Ala Ile Gln Trp Val Leu Thr Lys Val Gln Gly Tyr Ile
        435                 440                 445

Glu Ser Glu Arg Lys Val Arg Gln Ser Gln Ala Leu Ala Asn Ser Ile
    450                 455                 460

Ala His Glu Met Arg Asn Pro Leu Ser Gln Leu Gln Tyr His Phe Glu
465                 470                 475                 480

Lys Ile Lys His His Tyr Gln Lys Asn Thr Glu His Glu Lys Gln Glu
                485                 490                 495

Gln Leu Ile Lys Asn Glu Leu Asn Gln Gly Cys Leu Ala Ile Gln Lys
            500                 505                 510

Gly Ala Gln Leu Ile Asp Ile Leu Ser Glu Ala Lys Asn Thr Ala
        515                 520                 525

Ile Ser Asp Asp Leu Phe His His His Ser Ile Ser Leu Leu Thr Gln
    530                 535                 540

Gln Ile Ile Asp Glu Tyr Val Phe Asp Ser Glu Glu Met Lys Gln Lys
545                 550                 555                 560

Ile Thr Leu Asp Leu Glu Asp Asp Phe Ile Val Asn Ile Asn Asp Thr
                565                 570                 575
```

-continued

```
Leu Tyr Gly Phe Ile Leu Phe Asn Leu Leu Arg Asn Ala Thr Tyr Tyr
                580                 585                 590

Phe Asp Glu Tyr Asn Ser Ser Ile Ser Ile Arg Leu Val Lys Gly Phe
            595                 600                 605

Ala Thr Asn Lys Leu Ile Phe Arg Asp Thr Gly Pro Gly Ile Asp Ser
        610                 615                 620

His Ile Leu Pro Asn Ile Phe Asp Asp Phe Phe Thr His Asn Lys Glu
625                 630                 635                 640

Gly Gly Ser Gly Leu Gly Ser Tyr Cys Leu Arg Val Met His Ala
                645                 650                 655

Phe Glu Gly Asn Ile Ala Cys Tyr Ser Thr Lys Gly Glu Phe Thr Glu
            660                 665                 670

Phe Val Leu Ser Phe Pro His Ile Glu Gly Asp Ile Asn Ala Leu Asn
        675                 680                 685

Ser His Lys Ser Asn Thr Pro Pro Leu Ile Asn Lys Lys Asp Asn Ser
690                 695                 700

Leu Lys Thr Val Leu Ile Val Asp Asp Lys Lys Val Gln Arg Met Leu
705                 710                 715                 720

Ile His Thr Phe Ile Asn Lys Asp Asn Leu Thr Leu Leu Gln Ala Glu
                725                 730                 735

Asn Gly Glu Glu Ala Val Glu Ile Ala Thr Asn Asn Lys Leu Asp Leu
            740                 745                 750

Ile Phe Met Asp Ser Arg Met Pro Val Met Asn Gly Ile Asp Ala Ala
        755                 760                 765

Lys Lys Ile Lys Ile Ile Tyr Pro Asn Leu Pro Ile Ile Ala Leu Thr
770                 775                 780

Gly Glu Ser Ser His Glu Glu Ile Ser Ala Ile Thr Gln Val Met Asp
785                 790                 795                 800

Gly Tyr Leu Thr Lys Pro Val Ser Lys Ala Gln Leu Gln Gln Val Val
                805                 810                 815

Asp Lys Trp Leu
            820

<210> SEQ ID NO 10
<211> LENGTH: 964
<212> TYPE: PRT
<213> ORGANISM: Vibrio angustum

<400> SEQUENCE: 10

Met Ala Asp Leu Tyr Gln Ala Val Thr Thr Asn Val Ile Ala Ile Phe
1               5                   10                  15

Leu Ile Ala Ile Ser Ala Val Ile Ala Val Trp Thr Gly Tyr Phe Ala
                20                  25                  30

Arg Phe Leu His Ser Lys Pro Ser Leu Ser His Asp Lys Arg Ile Tyr
            35                  40                  45

Phe Pro Tyr Ile Ile Tyr Thr Ser Phe Ile Ser Leu Trp Ile Leu Ser
        50                  55                  60

Asn Ala Tyr Phe Gln Ser Ser Leu Leu Ile Glu Arg Ser Asp Ile Val
65                  70                  75                  80

Ala Val Asn Ile Ala Leu Ala Ala Asn Ile Phe Ser Gly Leu Ala Phe
                85                  90                  95

Ile Phe Ala Tyr Leu Phe Ser Cys Arg Ile Thr Ser Lys Lys Asp Asn
            100                 105                 110

Phe Ser Leu Thr Phe Thr Gln Lys Phe Leu Leu Tyr Thr Ser Ile Ile
        115                 120                 125
```

```
Ile Thr Leu Leu Thr Asn Ile Ile Pro Arg Ile Asn Ile Thr Ser Ile
    130                 135                 140

Asp Ile Lys Ala Ile Gly Val Phe Tyr Ile Asn Phe Gly Glu Leu Ser
145                 150                 155                 160

Phe Ile Phe Phe Gly Met Leu Ile Ile Leu Leu Ser Thr Ile Ile
                    165                 170                 175

Asn Leu Leu Ile Leu His Lys Asn Asn Thr Cys Ile Asn Arg Val Lys
                180                 185                 190

Ala Lys Tyr Met Ile Thr Gly Ile Ile Ala Phe Ile Ser Ser Thr Phe
        195                 200                 205

Leu Ile His Phe Ile Ala Ala Val Ile Phe His Asp Phe Thr Ala Ala
    210                 215                 220

Trp Leu Pro Pro Ala Leu Ser Val Ile Glu Val Phe Leu Ile Gly Tyr
225                 230                 235                 240

Ala Leu Phe Asn Ser Arg Phe Tyr Ser Leu Lys Tyr Ile Ile Phe Ile
                245                 250                 255

Thr Ser Ser Thr Phe Ile Asn Ile Ile Phe Tyr Thr Ala Pro Val Ile
                260                 265                 270

Leu Leu Glu Leu Tyr His Ile Lys Gly Thr Pro Phe Phe Leu Val Leu
    275                 280                 285

Trp Thr Leu Ile Thr Gly Phe Phe Trp His Arg Thr Leu Arg Leu Val
    290                 295                 300

Arg Leu Phe Ala Asn Lys Ile Ile Tyr His Lys Lys Gly Asn Pro Val
305                 310                 315                 320

Glu Asn Ile Thr Lys Ile Ile Ser Glu Phe Lys Ile Ser Thr Asp Leu
                325                 330                 335

Gly Ile Ser Lys Leu Asn Thr Val Ile His Ser Asn Asn Gly Ile Ile
                340                 345                 350

Val Gln Val Ser Asn Lys Asn Gln Leu Leu Arg Asp Tyr Phe Lys Thr
        355                 360                 365

Gly Arg Asn Ile Leu Leu Lys Gln Asp Leu Asp Val Leu Leu Asn Asp
    370                 375                 380

Asn Val Leu Ala Asp Asn His Leu His Leu Val Ser Glu Gln Leu His
385                 390                 395                 400

Lys Met Gly Val Thr Leu Val Val Pro Ile Leu Asp Glu Ser Lys Lys
                405                 410                 415

Ile Thr His Phe Tyr Ile Ala Ser Lys Glu Met Ser Asn Val Leu Phe
                420                 425                 430

Ser Cys Glu Glu Ile Met Gly Leu Gln Arg Leu Phe Glu Arg Ala Asn
        435                 440                 445

Arg Phe Ile Asp Thr Glu Glu Lys Val Arg Lys Ser Gln Val Leu Ala
450                 455                 460

Gly Ser Ile Ala His Glu Ile Arg Asn Pro Leu Ser Lys Ile Lys Tyr
465                 470                 475                 480

His Phe Glu Lys Ile Asp Ser Asp Phe Leu Ser Val His Lys Glu Ser
                485                 490                 495

Ile Asn Ser Leu Ala Thr Leu Glu Ile Glu Lys Ile His Gln Glu Leu
                500                 505                 510

Thr Glu Gly Lys Lys Ala Leu Gln Leu Gly Thr Lys Phe Ser Asp Val
        515                 520                 525

Ile Leu Asp Glu Leu Arg Gly Ser Ser Ile Ser Thr Ser Phe Phe Gln
530                 535                 540
```

His Tyr Ser Ala Ala Ser Leu Thr Ser Gln Ala Leu Asn Asp Phe Ser
545                 550                 555                 560

Leu Tyr Ser Glu Glu His Lys Lys Arg Ile His Leu Glu Ala Thr Asn
            565                 570                 575

Asn Phe Tyr Phe Tyr Gly Ser Asp Thr Leu Phe Ser Phe Val Leu Phe
        580                 585                 590

Asn Leu Leu Lys Asn Ala Val Tyr Tyr Phe Asp Thr Phe Pro Glu Ser
    595                 600                 605

His Ile Ser Ile Gln Phe Glu Lys Gly Leu Lys His Asn Lys Ile His
610                 615                 620

Val Arg Asp Thr Gly Pro Gly Ile Thr Glu Glu Gln Leu Glu Asn Leu
625                 630                 635                 640

Phe Asp Glu Phe Tyr Ser Phe Gly Lys Val Ser Gly Asn Gly Leu Gly
            645                 650                 655

Leu Ala Tyr Cys Lys Lys Val Met Glu Ser Phe Ser Gly Ser Ile Ser
            660                 665                 670

Cys His Ser Ile Leu Gly Glu Phe Thr Glu Phe Thr Leu Thr Phe Pro
    675                 680                 685

Ala Ile Asn Ile Gln Ser Asn Gly Glu Leu Thr Asn Pro Arg Ile Lys
    690                 695                 700

Gln His Leu Ser Gly Gln Ser Cys Leu Ile Leu Ser Ala Ser Ser Leu
705                 710                 715                 720

Ser Lys Lys Leu Thr Glu Ser Phe Asn Gly Leu Asn Met Asn Ile Glu
            725                 730                 735

Cys Ser Asn Asp Pro Ser Ile Gly Phe Thr Arg Ile Lys Asp Cys Pro
            740                 745                 750

Phe Asn Phe Ile Val Ile Asp His Arg Leu Tyr Ile Thr His Tyr Asp
        755                 760                 765

Gln Ile Ser Met Leu Arg Glu Gly Lys Tyr Gly Tyr Leu Ala Gln Ile
770                 775                 780

Thr Pro Ile Phe Ile Phe Asn Ser Thr Ser Ile Asn Leu Asn Asn Asp
785                 790                 795                 800

Arg Ile Asn Val Pro Lys Tyr Thr Gln Gly Tyr Ile Asp Thr Leu Asn
            805                 810                 815

Gly Ala Leu Ala Phe Glu Cys Ser Leu Glu Ala Ile Ile Asn Asp Thr
        820                 825                 830

Lys Phe Ala Pro Leu Gly Ser Leu Asn Asp Lys Thr Val Leu Val Val
    835                 840                 845

Asp Asp Met His Ala Asn Arg Leu Leu Val Lys Ala Tyr Leu Ser Lys
850                 855                 860

Glu Gly Ile Asn Val Ile Gln Ala Ala Ser Gly Tyr Glu Ala Ile Glu
865                 870                 875                 880

Gln Val Lys Lys Asn Asn Ile Asp Leu Ile Phe Met Asp Ile His Met
            885                 890                 895

Pro Gly Met Asn Gly Ile Glu Thr Ala Lys Gln Leu Lys Glu Leu Asp
        900                 905                 910

Ser Thr Lys Pro Ile Ile Ala Ile Ser Gly Glu Tyr Gly Glu Lys Ile
    915                 920                 925

Val Ser Asp Ile His Lys Val Met Asp Asp Tyr Ile Val Lys Pro Ile
    930                 935                 940

Glu Lys Ser Thr Leu Val Ser Leu Thr Ser Lys Trp Leu Ile Ile Asn
945                 950                 955                 960

Lys Val Lys Asp

<210> SEQ ID NO 11
<211> LENGTH: 793
<212> TYPE: PRT
<213> ORGANISM: Unknown
<220> FEATURE:
<223> OTHER INFORMATION: Description of Unknown: LuxN Vibrionales polypeptide

<400> SEQUENCE: 11

```
Met Gly Thr Ala Val Phe Met Ala Lys Phe Ala Asn Ile Ala Ser Ser
1               5                   10                  15

Leu Ala Phe Ala Phe Ala Phe Tyr Phe Ser Cys Gln Leu Tyr Ala Glu
            20                  25                  30

Gln Arg Lys Asp Asn Val Tyr Leu Trp Gln Arg Leu Ile Phe Cys Leu
        35                  40                  45

Leu Val Thr Tyr Ser Leu Cys Val Asn Leu Gln Gln Asp Gln Thr Val
    50                  55                  60

Lys Tyr Val Glu Val Leu Gly Pro Ser Gln Phe Ser Ile Glu Phe Gly
65                  70                  75                  80

Pro His Thr Ser Tyr Phe Phe Asn Ala Met Leu Cys Ser Met Leu Leu
            85                  90                  95

Thr Leu Phe Asn Leu Leu Ala Met Arg Val Asn Ser Asn Arg Leu Thr
        100                 105                 110

Leu Ala Lys Thr Asn Tyr Met Ile Ser Gly Ile Leu Val Tyr Met Leu
    115                 120                 125

Ser Thr Leu Ala Ile Gln Val Gly Met Thr Tyr Phe Leu Lys Asp Phe
130                 135                 140

Ser Leu Thr Trp Leu Pro Pro Ala Leu Ser Ile Ser Glu Met Met Phe
145                 150                 155                 160

Val Gly Tyr Ala Leu Leu Thr Ser Arg Phe Tyr Ser Val Lys Tyr Leu
            165                 170                 175

Ala Tyr Leu Gly Leu Asn Thr Leu Leu Val Cys Val Ile Leu Val Ile
        180                 185                 190

Pro Phe Gly Val Ile Phe Ile Pro Gln Thr Asp Asp Asn Gln Trp Leu
    195                 200                 205

Ile Ala Ile Pro Ile Cys Ala Met Ile Gly Ile Ala Trp His Val Leu
210                 215                 220

Tyr Lys Arg Val Ser Arg Tyr Ala Ser Phe Phe Val Tyr Gly Asn Lys
225                 230                 235                 240

Lys Thr Pro Val Gln Gln Ile Leu Ala Leu Glu Glu Asp Phe Lys Leu
            245                 250                 255

Ser Ile Asp Asp Ala Met Arg Arg Leu Gly Gln Leu Leu Gln Ile Pro
        260                 265                 270

Glu Asp Lys Leu Arg Leu Val Asn Ser Asn Tyr Asn Glu Thr Phe Tyr
    275                 280                 285

Glu Asp Tyr Leu Ser Thr Asn Glu Ser Val Leu Val Phe Asp Glu Leu
290                 295                 300

Ser Gln Glu Leu Asp Tyr Lys Thr Pro Ser Lys Leu Ser Leu Lys Ala
305                 310                 315                 320

Leu Tyr Asp Lys Met Ser Leu Asn Asn Thr Ala Leu Val Met Pro Leu
            325                 330                 335

Phe Gly Gln Gly Lys Ser Val Thr His Leu Leu Val Ser Ser His Lys
        340                 345                 350

Ser Asn Asp Gln Met Phe Ser Asn Glu Glu Ile Ser Ala Leu Gln Thr
```

-continued

```
            355                 360                 365
Leu Leu Ala Arg Val Gln Ser Thr Ile Glu Ala Asp Arg Arg Val Arg
        370                 375                 380
Gln Ser Arg Ala Leu Ala Asn Ser Ile Ala His Glu Met Arg Asn Pro
385                 390                 395                 400
Leu Ala Gln Val Gln Leu His Phe Glu Val Leu Lys Gln His Ile Glu
                405                 410                 415
Asn Gln Ala Pro Glu Lys Gln Ile Gln Leu Asp Ile Lys Asn Gly Gln
                420                 425                 430
Ala Ala Val Glu Arg Gly Arg Gln Leu Ile Asp Ile Leu Arg Glu
                435                 440                 445
Val Ser Asp Ser Ser Leu Glu His Gly Pro Val Thr Met Thr Ser Ile
        450                 455                 460
His Lys Ala Ile Asp Gln Ala Val Ser His Tyr Gly Phe Glu Asn Glu
465                 470                 475                 480
Lys Ile Ile Glu Arg Ile Arg Leu Pro Gln His Thr Asp Phe Val Ala
                485                 490                 495
Asn Leu Asn Glu Thr Leu Phe Asn Phe Val Ile Phe Asn Leu Ile Arg
                500                 505                 510
Asn Ala Ile Tyr Tyr Phe Asp Ser Tyr Pro Asp Ser Gln Ile Glu Ile
                515                 520                 525
Ser Thr Gln Leu Gly Ser Tyr Glu Asn Ile Leu Thr Phe Arg Asp Thr
        530                 535                 540
Gly Pro Gly Ile Asp Glu Val Ile Arg His Lys Ile Phe Asp Asp Phe
545                 550                 555                 560
Phe Ser Tyr Gln Lys Ser Gly Gly Ser Gly Leu Gly Leu Gly Tyr Cys
                565                 570                 575
Gln Arg Val Met Arg Ser Phe Gly Gly Arg Val Glu Cys Gln Ser Glu
                580                 585                 590
Arg Gly Lys Phe Thr Glu Phe His Leu Tyr Phe Pro Val Val Pro Asn
                595                 600                 605
Ala Pro Lys Ala Asp Thr Leu Arg Thr Pro Tyr Phe Asn Asp Trp Gln
        610                 615                 620
Gln Arg Gln Thr Leu Val Asp Asn Thr Asp Glu Ala Ile Glu Gln Pro
625                 630                 635                 640
Gln Asn Ile Arg Ile Glu Glu Lys Gly Leu Asp Ala Ile Ala Thr Gln
                645                 650                 655
Ile Thr Thr Asn Ser Ile Thr Pro Thr Val Leu Ile Val Asp Asp Lys
                660                 665                 670
Glu Val Gln Arg Thr Leu Val Gln Met Tyr Leu Asn Arg Leu Gly Val
                675                 680                 685
Asn Ser Leu Gln Ala Lys Gly Glu Asn Ala Ile Glu Leu Phe Arg
        690                 695                 700
Lys Asn His Val Asp Leu Ile Leu Met Asp Val Gln Met Pro Val Met
705                 710                 715                 720
Asn Gly Phe Glu Ala Ser Gln Ile Ile Lys Ala Arg Ser Pro Asn Thr
                725                 730                 735
Pro Ile Ile Ala Leu Ser Gly Glu Ser Gly Gln Arg Glu Leu Glu Met
                740                 745                 750
Ile Ala Gln Leu Met Asp Ala Arg Leu Glu Lys Pro Thr Ser Ile Asp
                755                 760                 765
Ala Leu Lys Ile Val Leu Asp Lys Trp Leu Tyr Lys Asn Thr Thr Lys
        770                 775                 780
```

Glu Val Ser Lys Glu Ala Glu Ser Glu
785              790

INHIBITION OF QUORUM SENSING-MEDIATED PROCESSES IN BACTERIA

CROSS-REFERENCE TO RELATED APPLICATIONS

This application is a continuation of U.S. patent application Ser. No. 14/028,999, filed Sep. 17, 2013, which is a continuation of U.S. patent application Ser. No. 12/995,476, filed Jan. 13, 2011, which is a National Stage of PCT Application No. PCT/US09/03348, filed Jun. 2, 2009, which claims priority to U.S. Provisional Application No. 61/130,685, filed Jun. 2, 2008 and U.S. Provisional Application No. 61/188,310, filed Aug. 7, 2008, all of which are herein incorporated in their entirety.

STATEMENT OF GOVERNMENT INTEREST

This invention was made with government support under Grant No. GM065859; Grant No. GM787552 and Grant No. AI054442 awarded by the National Institutes of Health and under Grant No. MCB0343821 and Grant No. MCB0639855 awarded by the National Science Foundation. The government has certain rights in the invention.

The antagonist screen was partly funded with federal funds supplied to the National Cancer Institute's Initiative for Chemical Genetics, National Institutes of Health, under Contract No. N01-CO-12400 and has been performed with the assistance of the Chemical Biology Platform of the Broad Institute of Harvard and MIT. The content of this publication does not necessarily reflect the views or policies of the Department of Health and Human Service, nor does mention of trade names, commercial products or organizations imply endorsement by the U.S. Government.

FIELD OF THE INVENTION

This invention relates to quorum sensing activities, and more particularly to antagonists of the receptor for acyl-homoserine lactone-type autoinducer molecules. In particular, the invention provides novel small molecules and methods of use of those molecules for controlling bacterial growth and pathogenesis.

BACKGROUND OF THE INVENTION

Quorum sensing is a process of bacterial cell-cell communication that involves production and detection of secreted signaling molecules called autoinducers (AI). Quorum sensing allows bacteria to collectively regulate gene expression and thereby function as multi-cellular organisms. For example, the bioluminescent Gram-negative quorum-sensing bacterium *Vibrio harveyi* integrates information from three different diffusible autoinducers that together enable intra- and inter-species communication. The three *V. harveyi* autoinducers are AI-1 (3-hydroxybutanoyl homoserine lactone), AI-2 ((2S,4S)-2-methyl-2,3,3,4-tetrahydroxytetrahydrofuran-borate), and CAI-1 ((S)-3-hydroxytridecan-4-one). These signals are detected by the sensor-kinase proteins, LuxN, LuxQ, and CqsS, respectively (FIG. 1A) (Henke, J. M., and Bassler, B. L. (2004b). J Bacteriol 186, 6902-6914). At low cell density, (i.e., in the absence of autoinducers), these sensor kinases autophosphorylate and transfer phosphate to the shared phospho-transfer protein, LuxU. LuxU transfers the phosphoryl-group to the DNA-binding response regulator, LuxO, which activates transcription of genes encoding five redundant small regulatory RNAs called the quorum regulatory RNAs (Qrrs) (FIG. 1A). The Qrrs destabilize the mRNA transcript encoding the master quorum-sensing regulator, LuxR. Therefore, under low-cell-density conditions, the bacteria do not display quorum-sensing behaviors. In contrast, at high cell density the three autoinducers accumulate and bind to their cognate receptors. These binding events switch the receptors to phosphatases, resulting in dephosphorylation of LuxO and termination of Qrr production. The luxR transcript is stabilized, leading to LuxR protein production (FIG. 1A). LuxR controls the genes in quorum sensing, e.g., genes required for bioluminescence, siderophore production, type III secretion, and metalloprotease production (Fuqua, C., Winans, S. C., and Greenberg, E. P. (1996). Annu Rev Microbiol 50, 727-751; Hammer, B. K., and Bassler, B. L. (2003). Mol Microbiol 50, 101-104; Henke, J. M., and Bassler, B. L. (2004a). J Bacteriol 186, 3794-3805; McFall-Ngai, M. J., and Ruby, E. G. (2000). Curr Opin Microbiol 3, 603-607; Miller, M. B., and Bassler, B. L. (2001). Annu Rev Microbiol 55, 165-199; Waters, C. M., and Bassler, B. L. (2005). Annu Rev Cell Dev Biol 21, 319-346).

AI-1 is an acyl homoserine lactone (AHL) type autoinducer and it is the strongest of the three *V. harveyi* signals and, thus, the major input controlling quorum-sensing-regulated behaviors. Typically, AHL autoinducers are detected by cytoplasmic LuxR-type transcriptional activators (note: these LuxR-type proteins are unrelated to *V. harveyi* LuxR, FIG. 1A). *V. harveyi* is unusual because all three of its autoinducers, including AI-1, are detected by membrane-bound sensor-kinase proteins (in the case of AI-2, however, an additional periplasmic binding protein LuxP is required in conjunction with the membrane-bound two-component protein LuxQ). AI-1 is also the defining member of a growing family of recognized AHL type autoinducers that interact with membrane-bound sensor-kinases like LuxN, rather than with cytosolic LuxR-type proteins (Freeman, J. A., et al. (2000). Mol Microbiol 35, 139-149; Jung, K., et al. (2007). J Bacteriol 189, 2945-2948; Timmen, M., et al. (2006). J Biol Chem 281, 24398-24404). There are currently 11 LuxN homologs in the National Center for Biotechnology Information (NCBI) database, but nothing is known about how AHLs interact with this important class of receptors (FIG. 2A-H).

Bacteria that use the AI-1 signaling factor associate with higher organisms, i.e., plants and animals, at some point during their life cycles. Some examples include *Pseudomonas aeruginosa, Erwinia carotovora, Pseudomonas aureofaciens, Yersinia enterocolitica, V. harveyi*, and *agrobacterium tumefaciens*. *P. aeruginosa* is an opportunistic pathogen in humans with cystic fibrosis. *E. carotovora* infects certain plants and results in soft rot disease. *Y. enterocolitica* causes gastrointestinal disease in humans and reportedly produces an autoinducer. *P. aureofaciens* synthesizes antibiotics under autoinducer control that block fungus growth in the roots.

Quorum sensing takes place not only among luminous marine bacteria like *V. harveyi*, but also among pathogenic bacteria where it regulates the production of virulence factors. Thus, it would be an advance to identify compounds useful for controlling pathogenic bacteria, and for augmenting traditional antibiotic treatments.

SUMMARY OF THE INVENTION

The present invention provides molecules that can be used to positively and negatively manipulate quorum-sensing-mediated communication to control bacterial behavior. Fifteen small-molecules were identified.

Accordingly, in a first aspect, the invention features a small molecule compound characterized by its ability to bind to *Vibrio harveyi* LuxN at the autoinducer-1 (AI-1) binding site of LuxN, wherein the compound is not AI-1. The isolated compound is one embodiment of the invention.

In a preferred embodiment, the compound is one of the small molecules from the group consisting of the fifteen structures shown in FIGS. 3A-3O. The compound is an antagonist of *V. harveyi* LuxN.

In a related aspect, the invention features a method of disrupting detection of acyl-homoserine lactone autoinducer in Gram-negative bacteria comprising contacting the bacteria with the small molecule compound.

In another related aspect, the invention features a pharmaceutical composition comprising a pharmaceutically acceptable carrier, excipient or diluent and one or more of the compounds selected from the group consisting of the fifteen structures shown in FIGS. 3A-3O.

In a further related aspect, the invention features a method of inhibiting bacterial infection of a host comprising contacting the bacteria with the pharmaceutical composition, wherein the bacteria are Gram-negative quorum sensing bacteria. "Contacting the bacteria" is by means of administering the composition to the host, which can be topical administration or administration to the host internally by means known in the art.

In yet another related aspect, the invention features a bacterial biofilm-inhibiting composition comprising one or more compounds selected from the group consisting of the fifteen structures shown in FIGS. 3A-3O. In a preferred embodiment the composition also comprises DMSO.

In still another related aspect, the invention features a method of controlling growth of quorum sensing Gram-negative bacteria attached to a solid surface, comprising exposing the bacteria to the bacterial biofilm-inhibiting composition.

A related aspect of the invention features a method of preventing biofilm formation on a solid surface comprising administering the bacterial biofilm-inhibiting composition to the surface.

Another aspect of the invention features a method of inhibiting quorum sensing-mediated activity in Gram-negative bacteria comprising contacting the bacteria with the antagonist compound selected from the group consisting of the fifteen structures shown in FIGS. 3A-3O.

In a preferred embodiment, the quorum sensing-mediated activity is pathogenicity. In another embodiment the bacteria are pathogenic to humans, animals, or plants. In another embodiment the bacteria are pathogenic to marine life. In a particularly preferred embodiment the activity is pathogenicity and the bacterial species is selected from *V. harveyi* and *C. violaceum*.

In another preferred embodiment, the activity is bioluminescence, siderophore production, type III secretion, or metalloprotease production.

Another aspect of the invention features a use of one or more of the compounds from the group consisting of the fifteen structures (A-O) in FIGS. 3A-3O for preparation of a medicament for treatment of a bacterial infection wherein the bacteria are Gram-negative quorum sensing bacteria.

Yet another aspect of the invention features a medical device that is coated with one or more of the compounds from the group consisting of the fifteen structures (A-O) in FIGS. 3A-3O. In a preferred embodiment the device is a catheter.

Additional features and advantages of the present invention will be better understood by reference to the drawings, detailed description and examples that follow.

BRIEF DESCRIPTION OF THE DRAWINGS

Figure 2A:
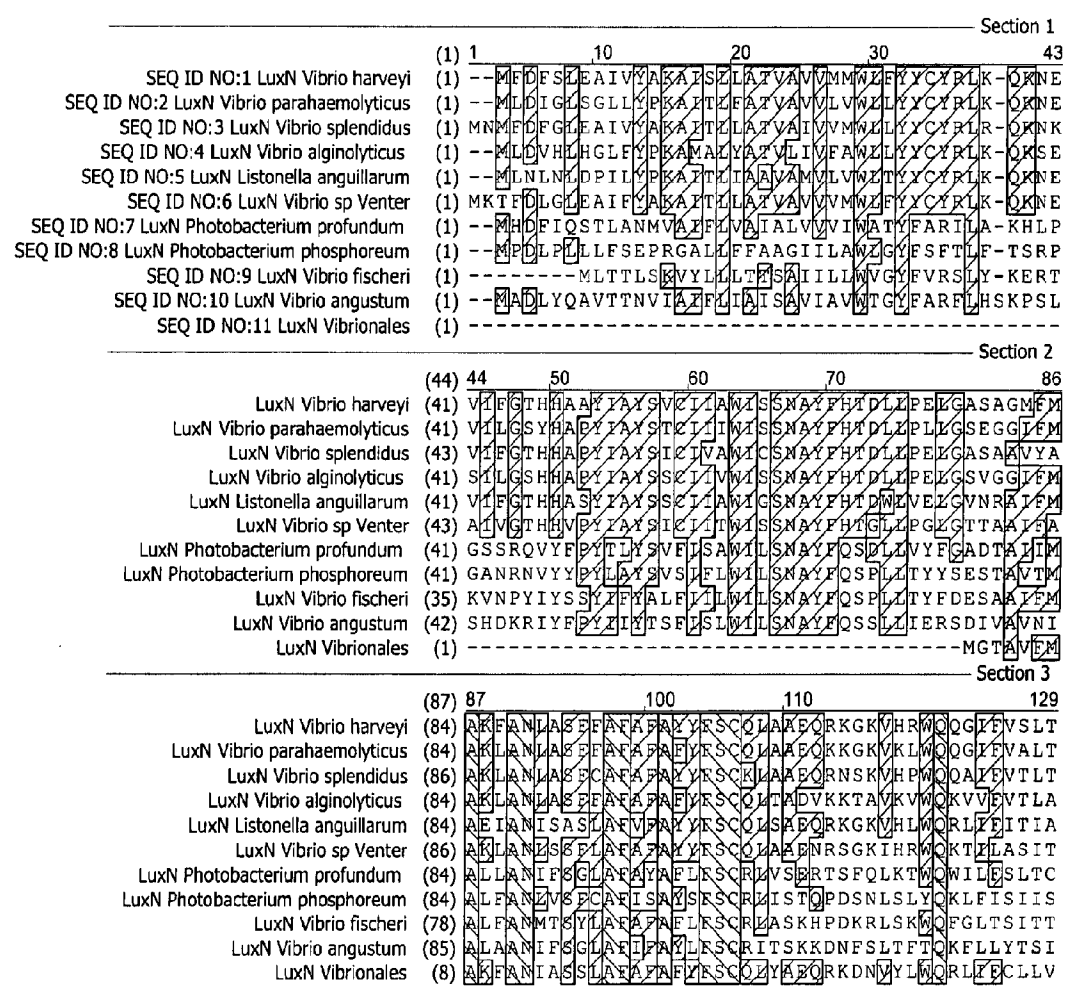
Figure 2B:
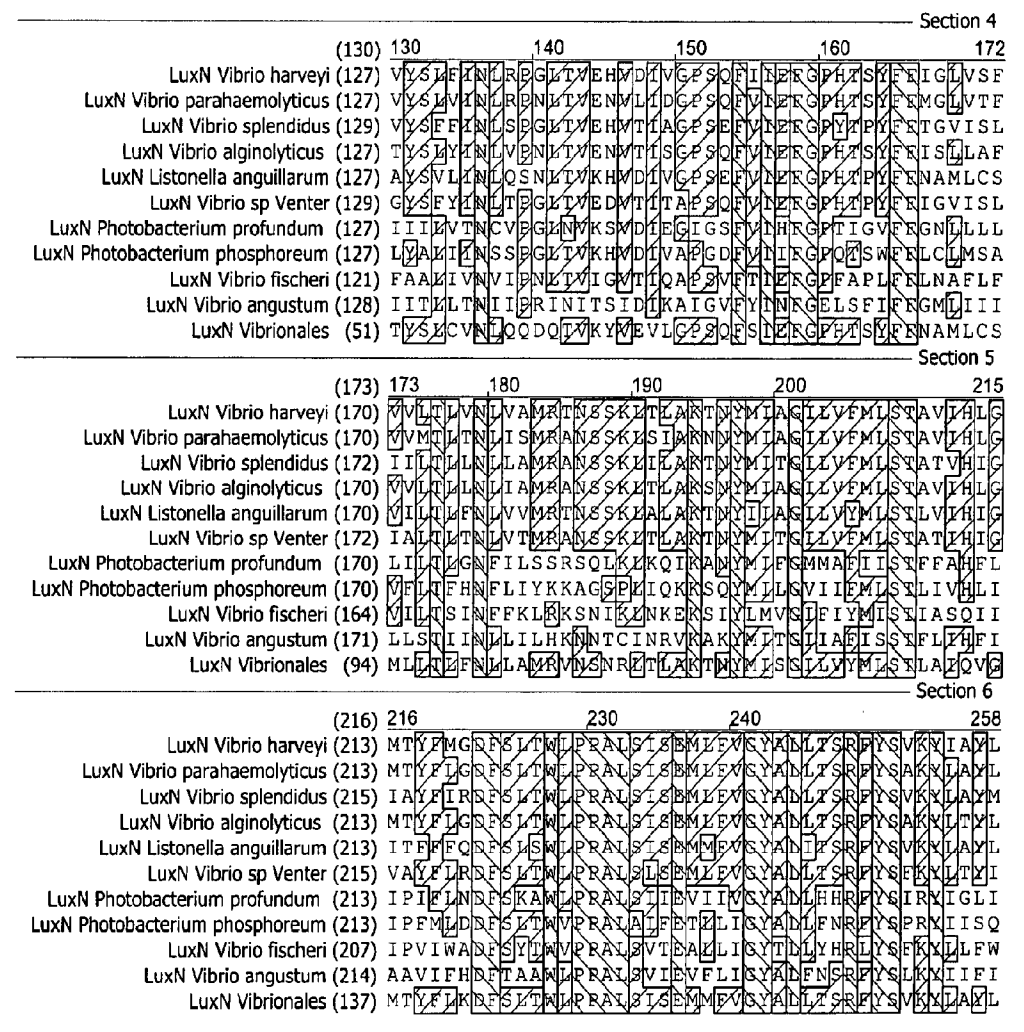
Figure 2C:
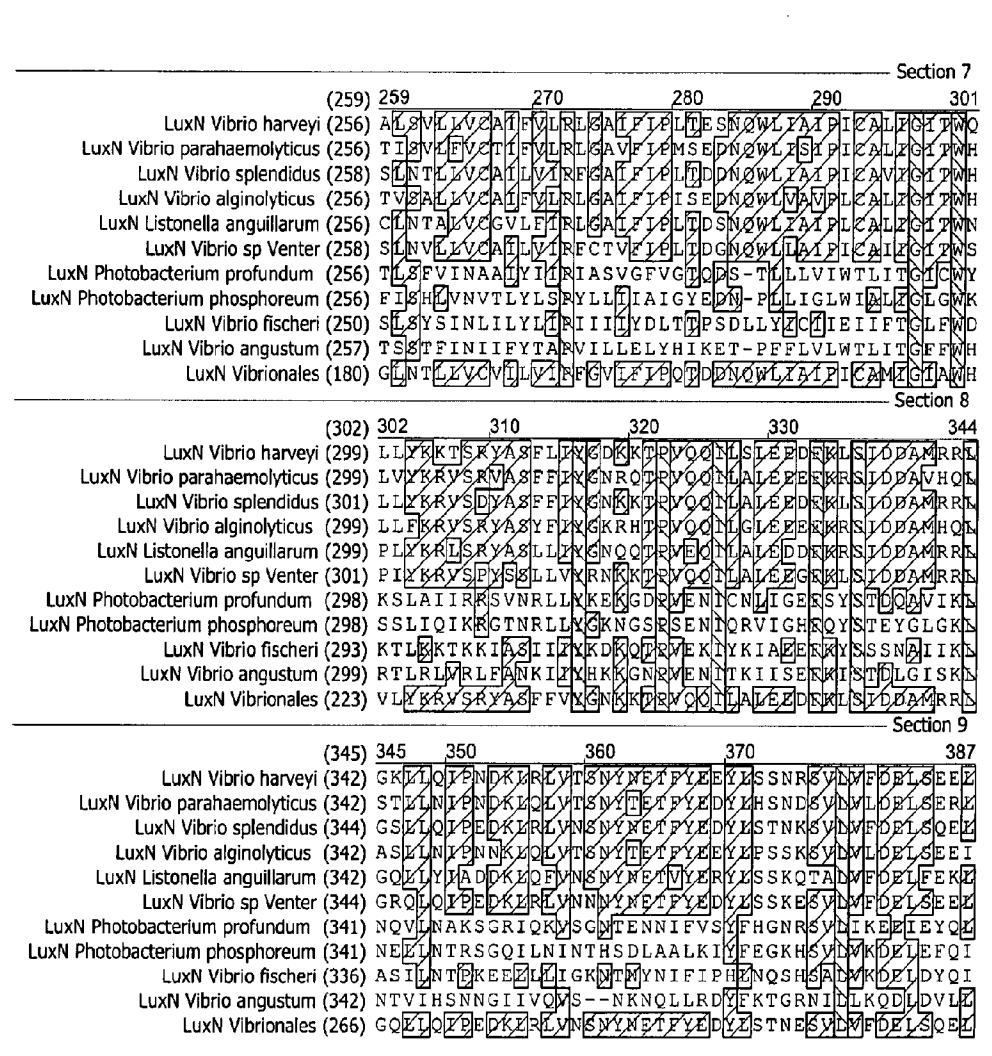
Figure 2D:
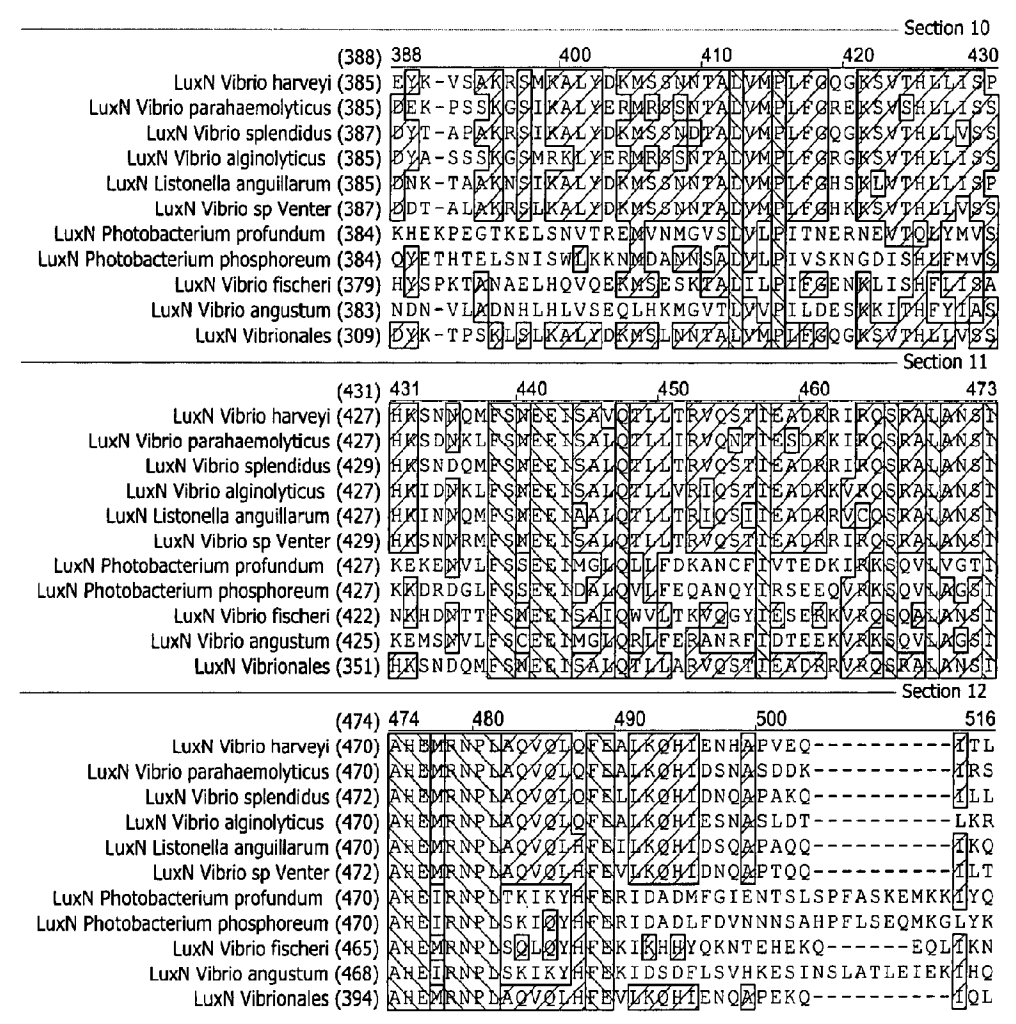
Figure 2E:
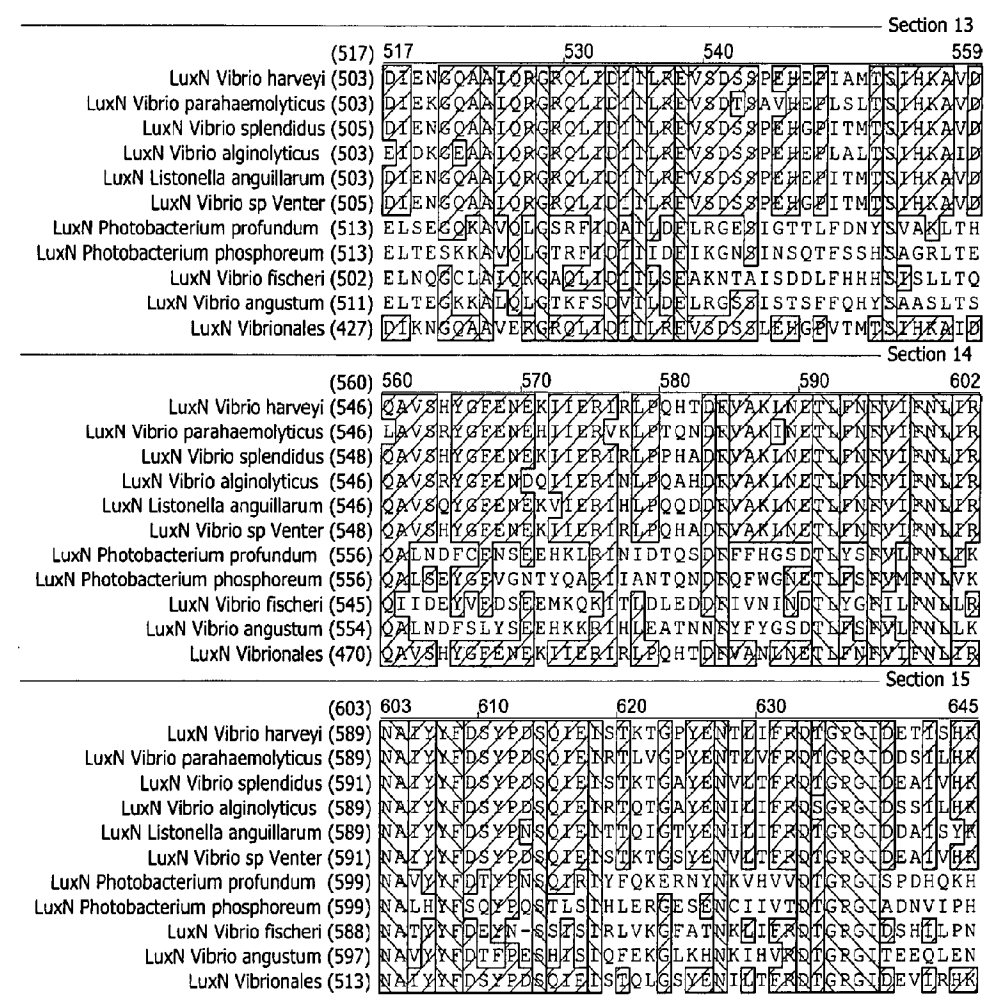
Figure 2F:
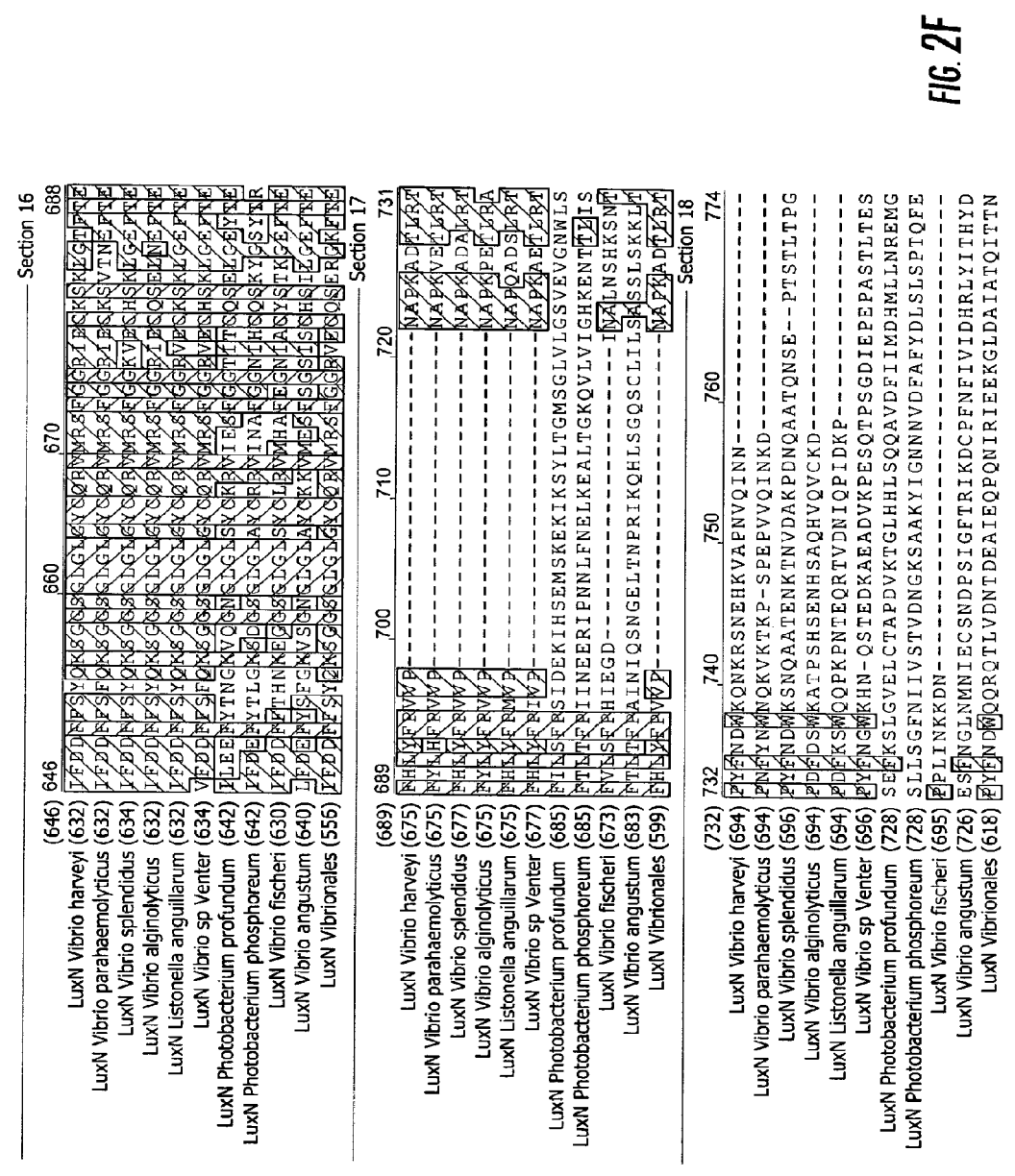
Figure 2H:
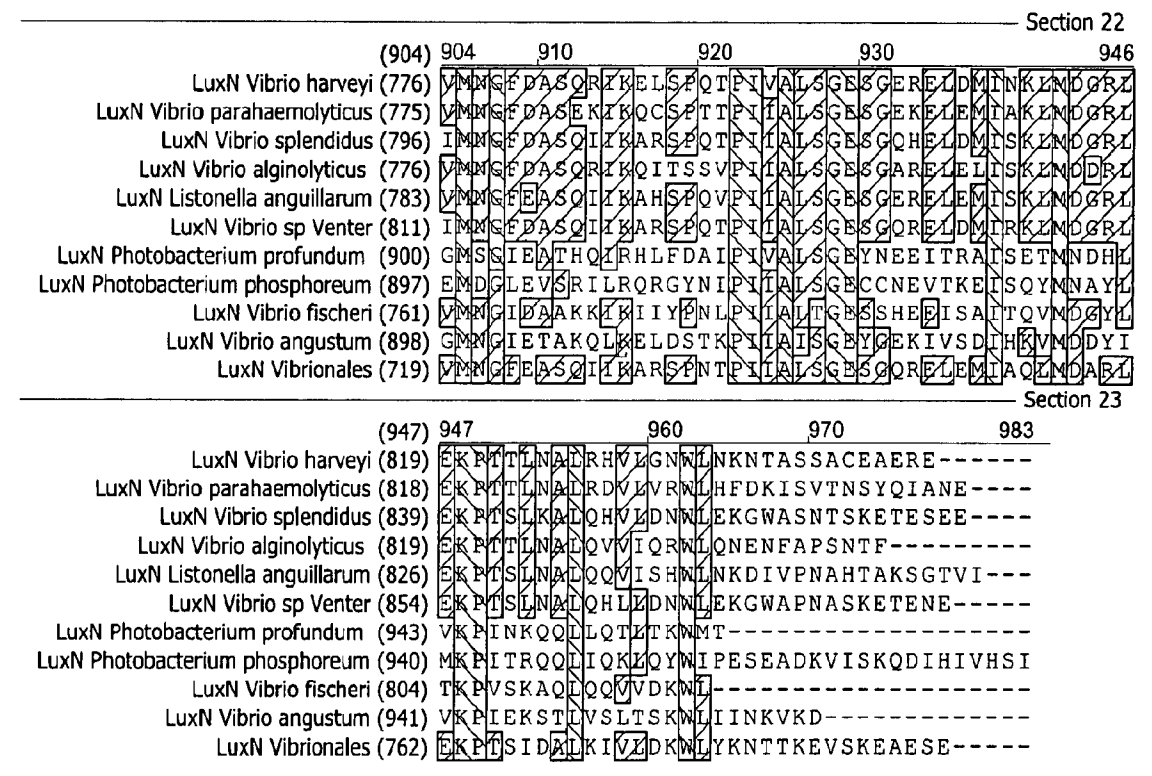

FIGS. 2A-2H. LuxN Sequence Alignment. *V. harveyi* LuxN was used to identify other LuxN homologs in the NCBI data base by a basic local alignment comparison. The LuxN homologs were aligned using the Vector NTI AlignX protocol. Dark gray shaded residues indicate a 100% conserved amino acid in all 11 LuxN homologs. Light gray shaded residues indicate that the particular amino acid is greater than 50% conserved.

*elegans* was infected with either wild type or mutant *C. violaceum* bacteria and survival times were recorded. The CviR mutant lacks the cytosolic receptor for the autoinducer. The CviI mutant lacks the autoinducer synthase, so the autoinducer is not produced.

Figure 6A:
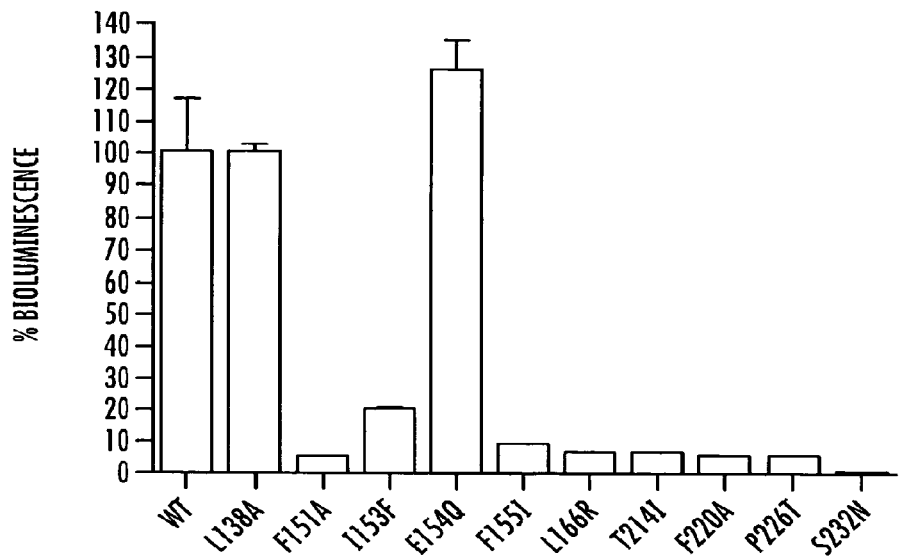
Figure 6B:
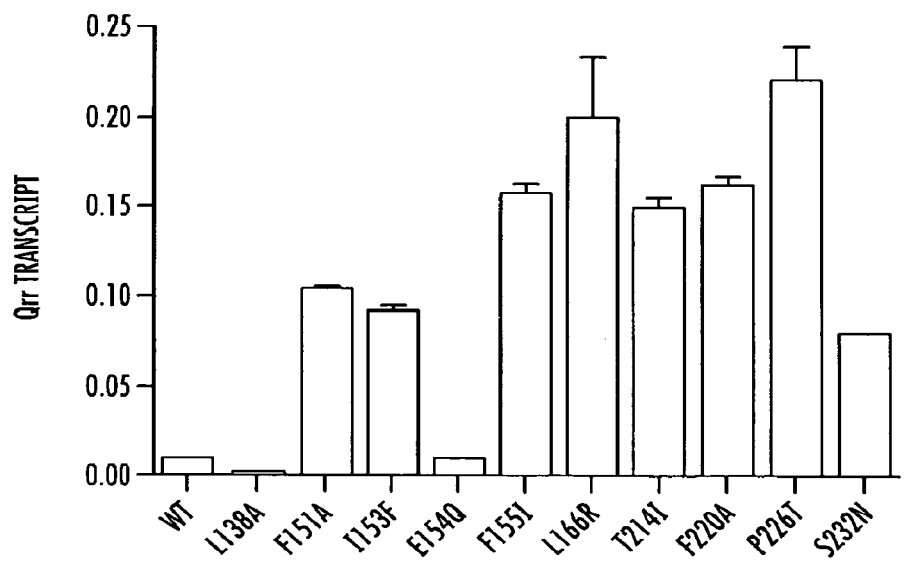

FIGS. 6A-6B. Representative LuxN Mutations that Reduce Light Production and Increase Qrr Transcription. (6A) Light production and (6B) Qrr4 transcript levels at steady state in wild-type and representative LuxN mutants. All cultures were grown and tested in triplicate. Light production from the wild type strain was set as 100%, and light production from each LuxN mutant was normalized to that reference. Qrr transcript levels were measured by qRT-PCR and are reported as relative transcript values. LuxN L138A and LuxN E154Q are control mutants that do not exhibit defects in light production or Qrr transcription.

Figure 7A:
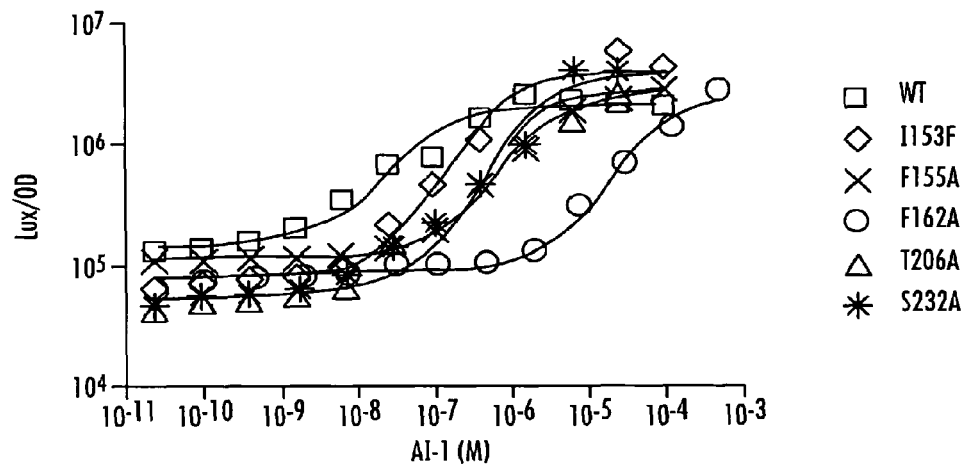
Figure 7B:
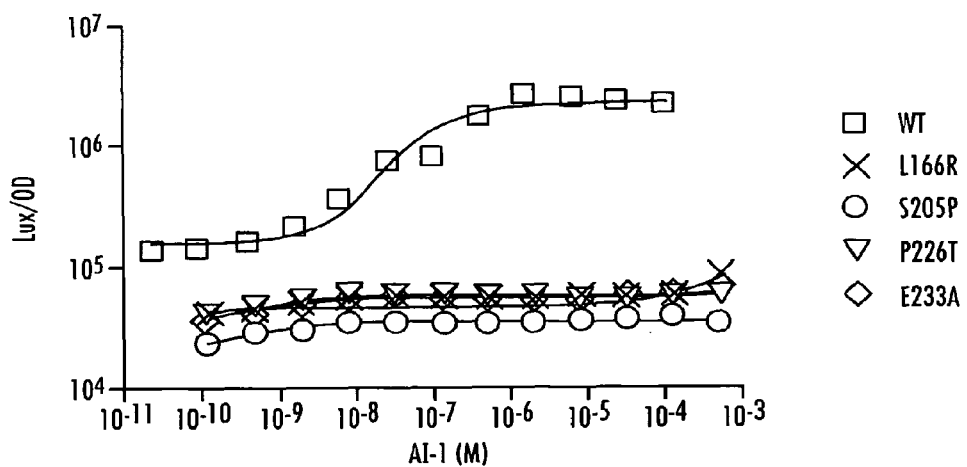
Figure 8A:
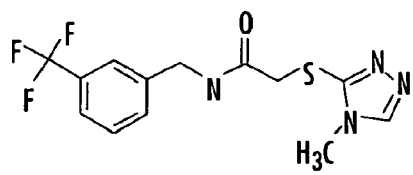
Figure 8A:
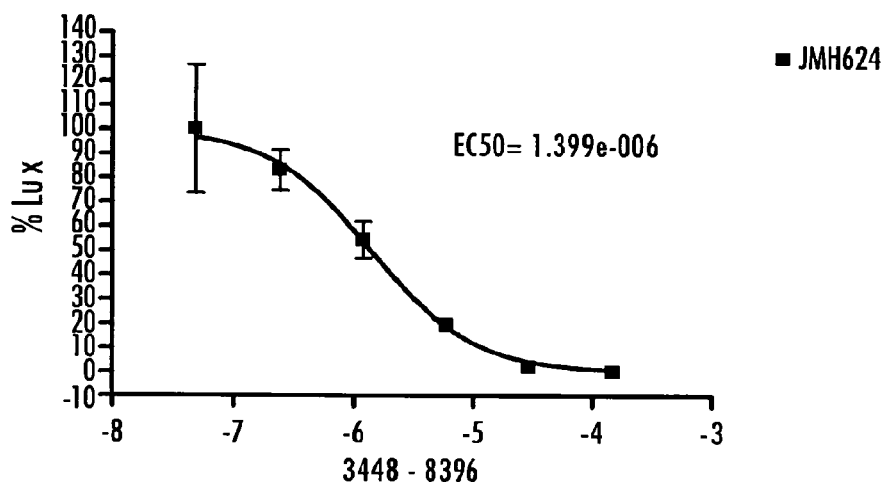
Figure 8B:
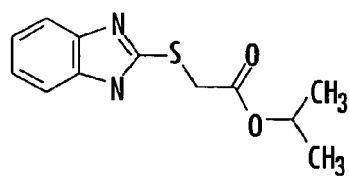
Figure 8B:
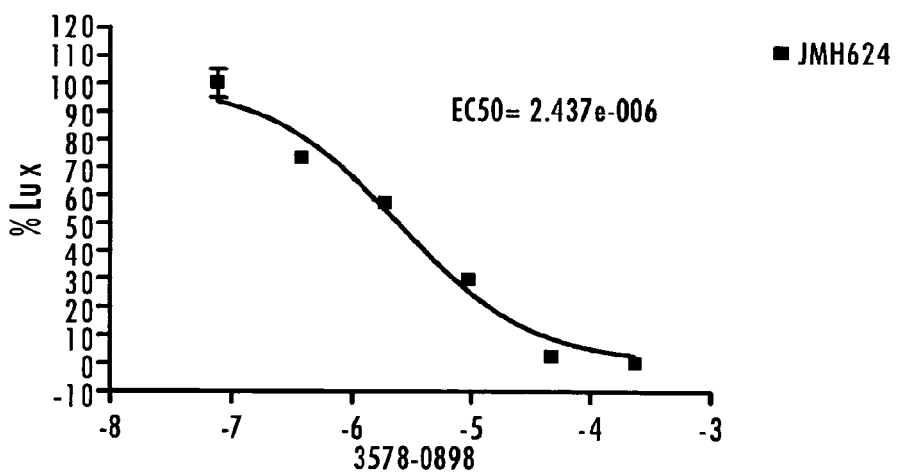
Figure 8C:
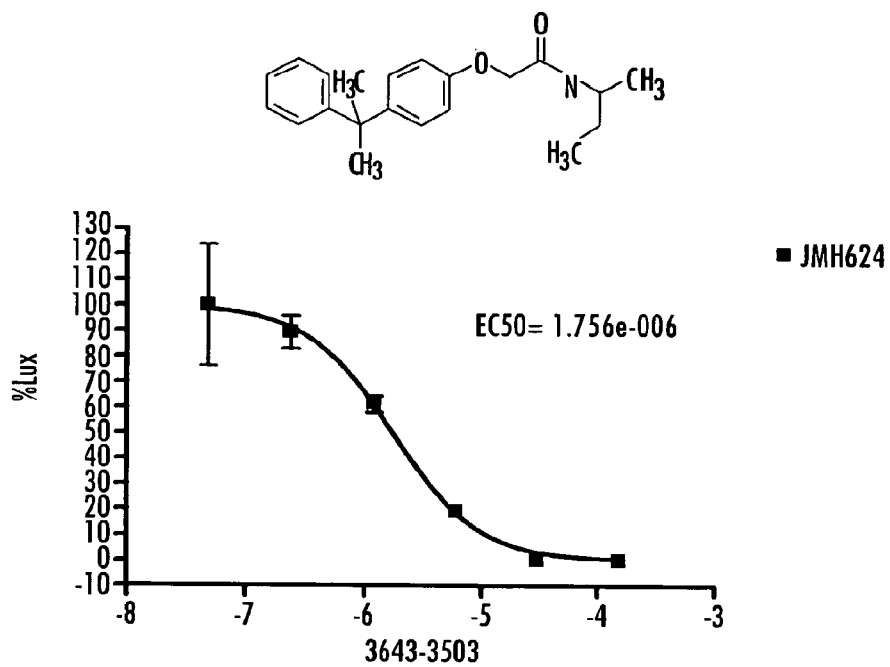
Figure 8D:
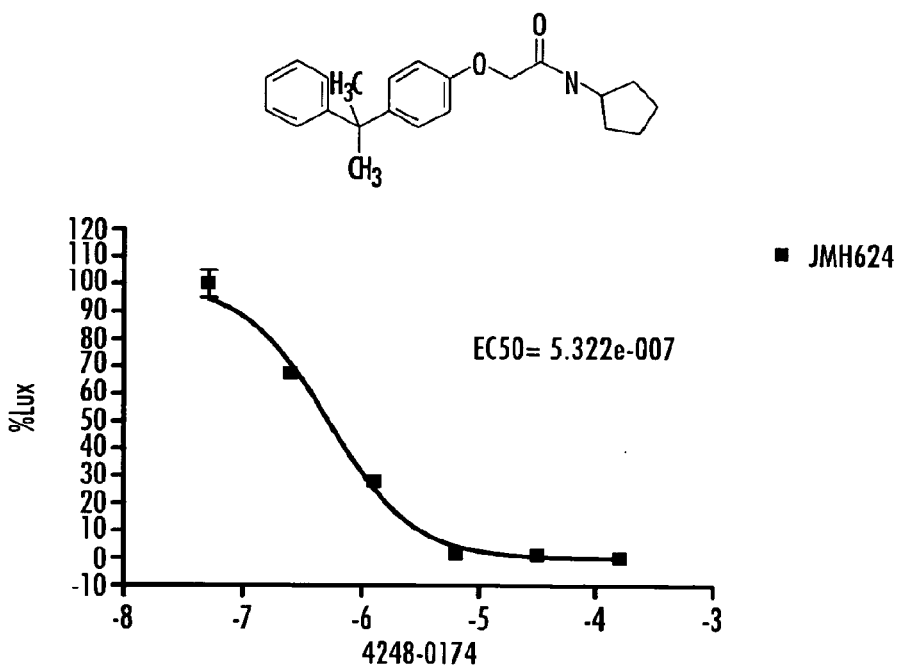
Figure 8E:
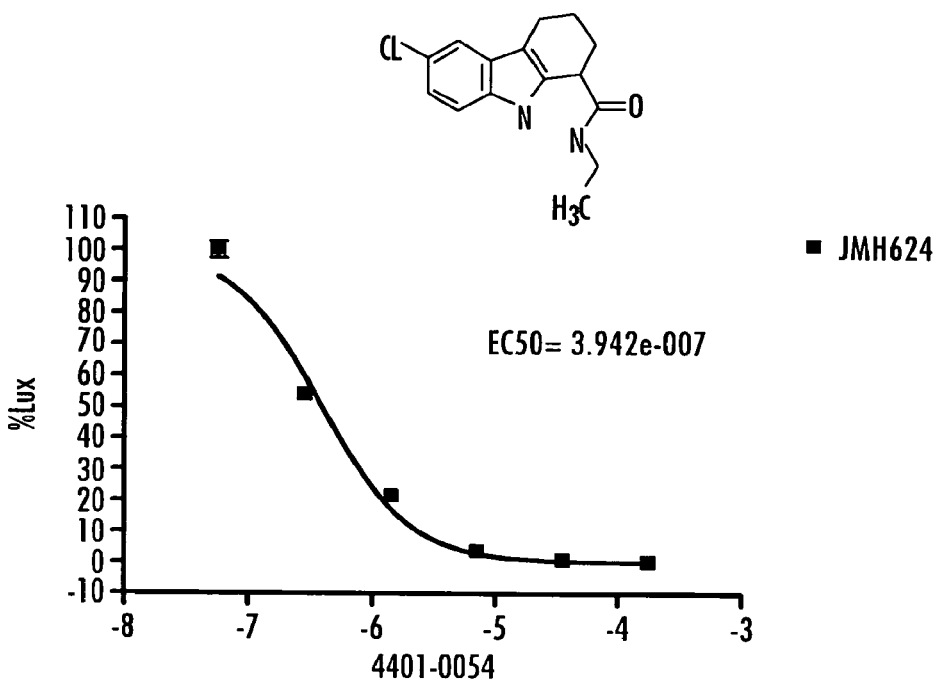
Figure 8F:
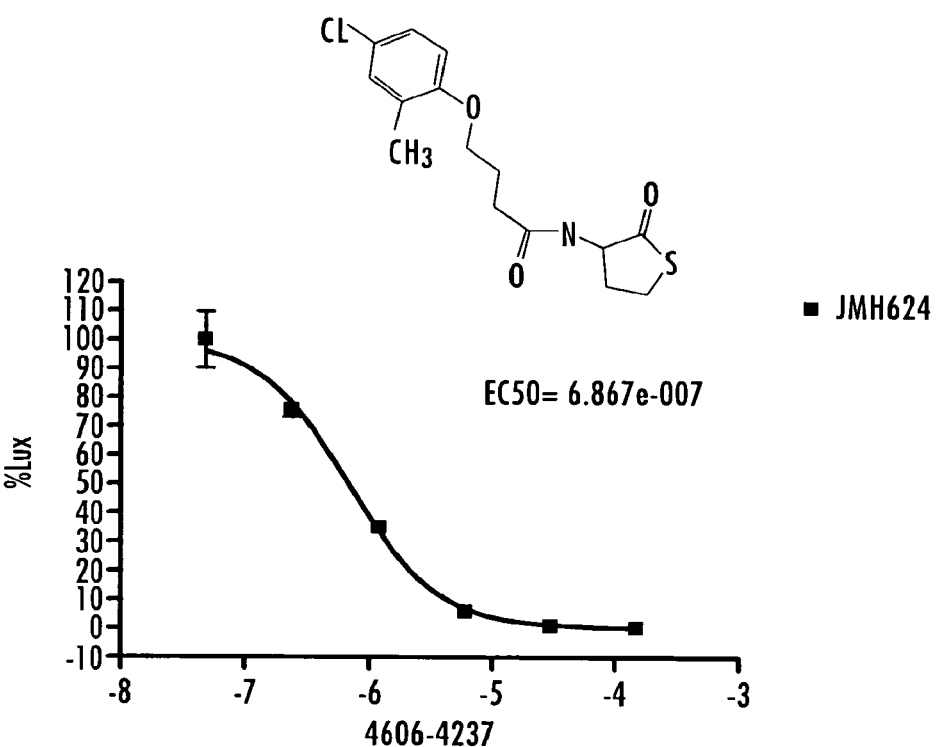
Figure 8G:
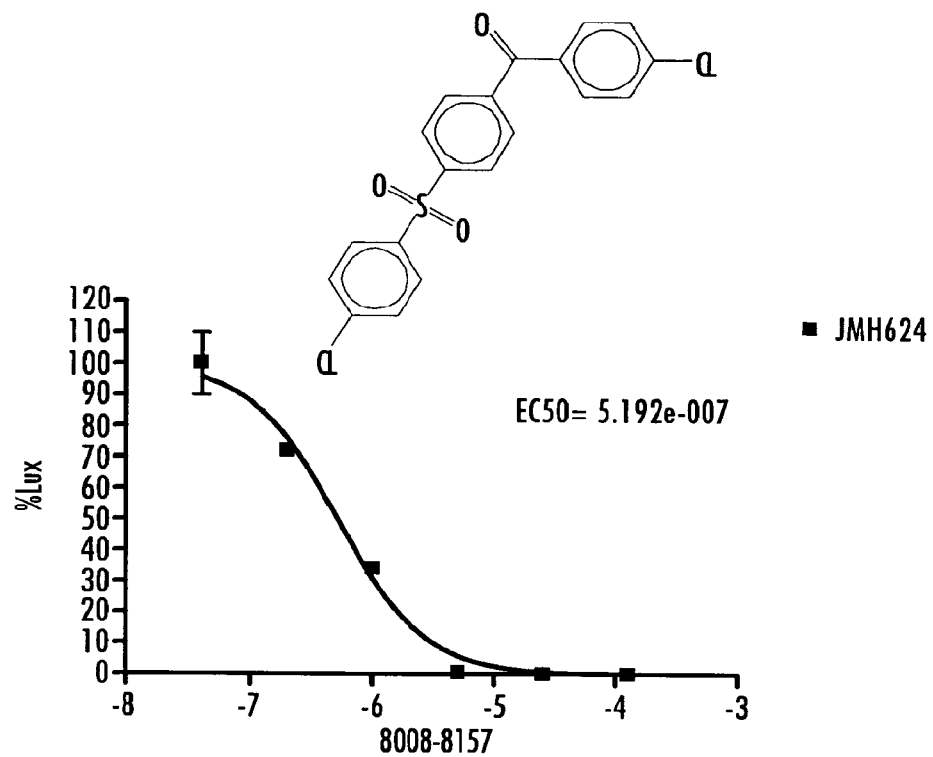
Figure 8H:
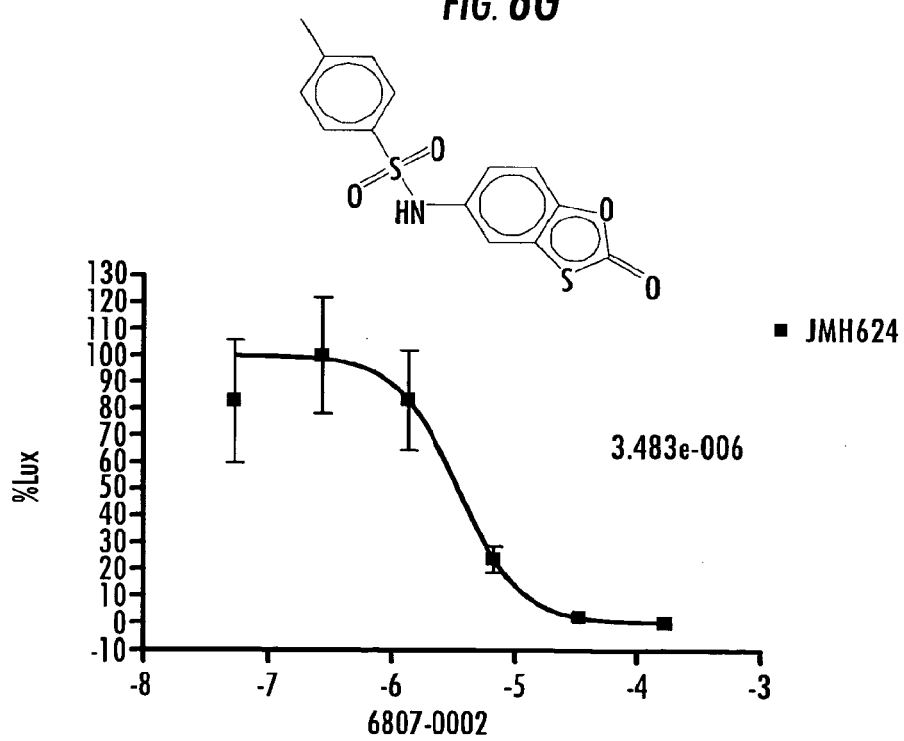
Figure 8I:
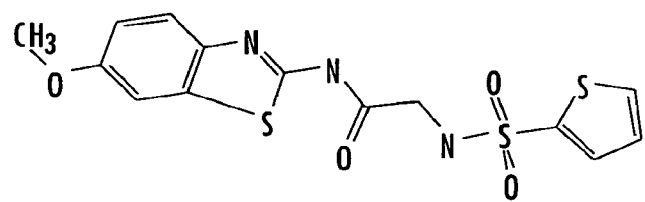
Figure 8I:
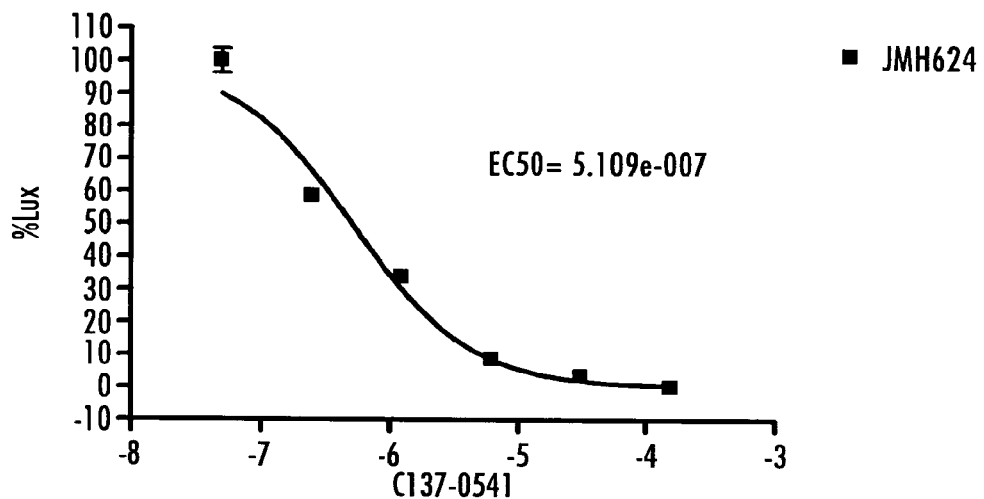
Figure 8J:
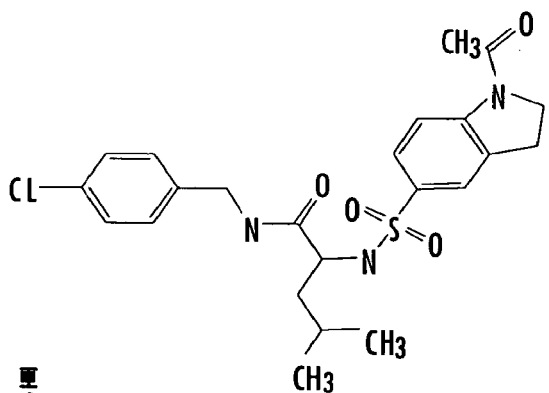
Figure 8J:
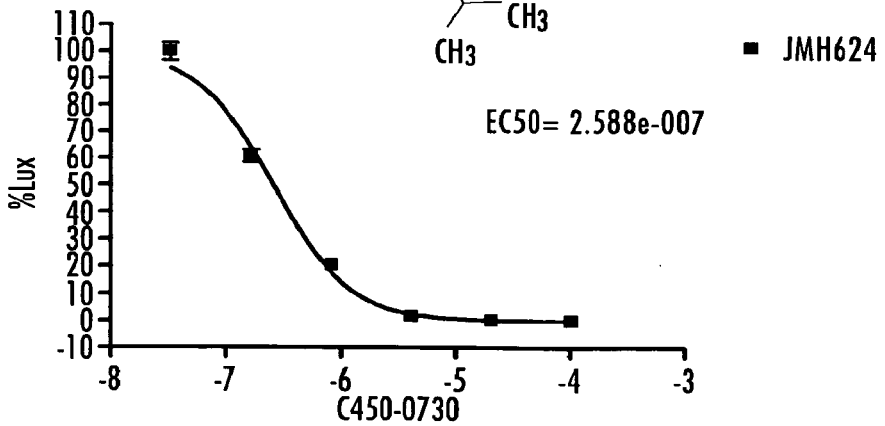
Figure 8K:
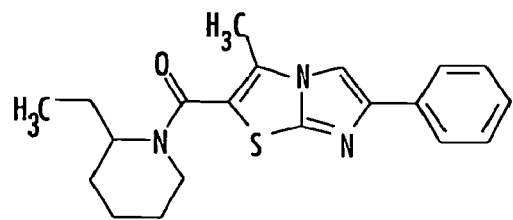
Figure 8K:
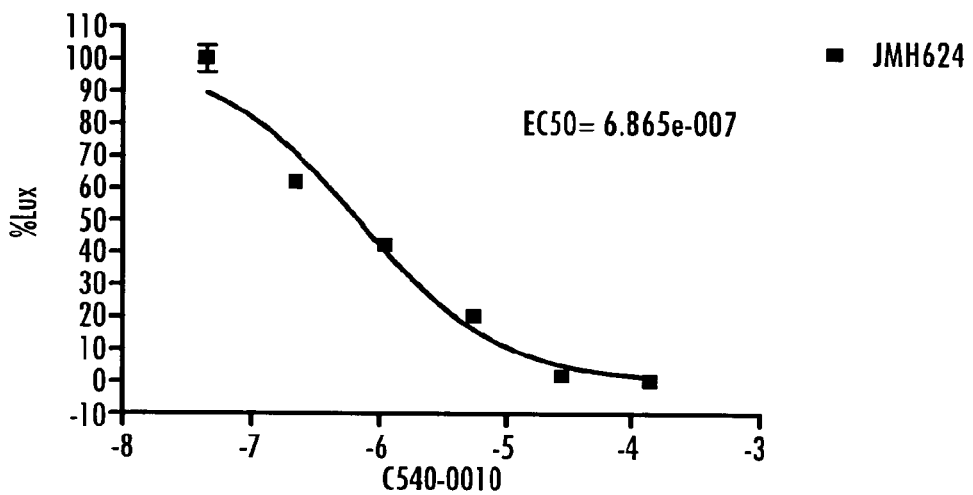
Figure 8L:
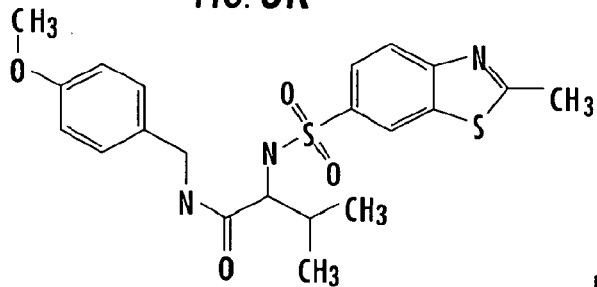
Figure 8L:
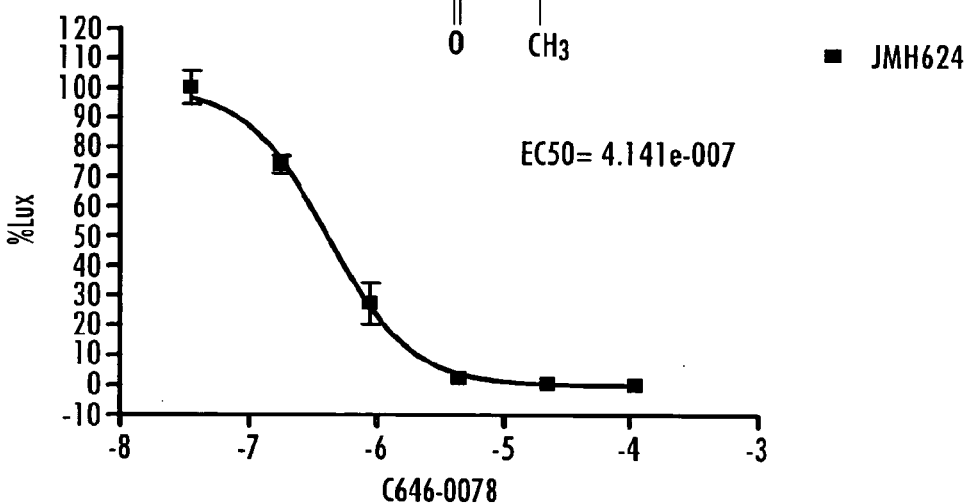

FIGS. 7A-7B. LuxN AI-1 Dose-Response Curves. (7A) Light production at various AI-1 concentrations is shown for wild-type LuxN and for representative LuxN mutants that have increased AI-1 EC-50 values. The data were fit with a variable-slope sigmoidal dose-response curve to determine the $EC_{50}$ values. (7B) Light production at various AI-1 concentrations is shown for wild-type LuxN and for representative LuxN mutations that cause constitutive dark phenotypes at all AI-1 concentrations. $EC_{50}$ values were not determined for these mutants.

FIGS. 8A-8L. Dose response of LuxN Antagonists. The concentration of the antagonist molecule is shown on the X-axis, the light output (% lux) is shown on the Y-axis. Squares denote the light output by the double sensor mutant *V. harveyi* strain JMH624 (ΔluxM, ΔluxPQ) in the presence of 20 nM AI-1 at various concentrations of the antagonist. The chemical structure of the antagonist and the effective concentration ($EC_{50}$) are given. (8A) Antagonist 3448-8396. (8B) Antagonist 3578-0898. (8C) Antagonist 3643-3503. (8D) Antagonist 4248-0174. (8E) Antagonist 4401-0054. (8F) Antagonist 4606-4237. (8G) Antagonist 8008-8157. (8H) Antagonist 6807-0002. (8I) Antagonist C137-0541. (8J) Antagonist C450-0730. (8K) Antagonist C540-0010. (8L) Antagonist C646-0078.

Figure 9A:
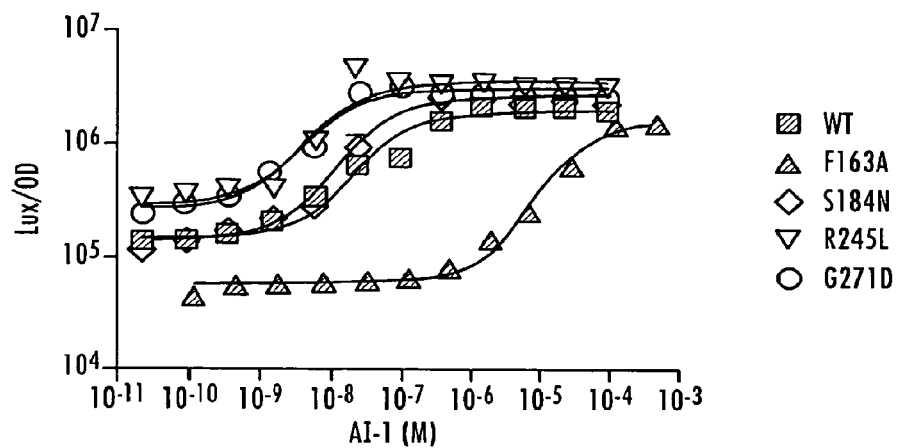
Figure 9B:
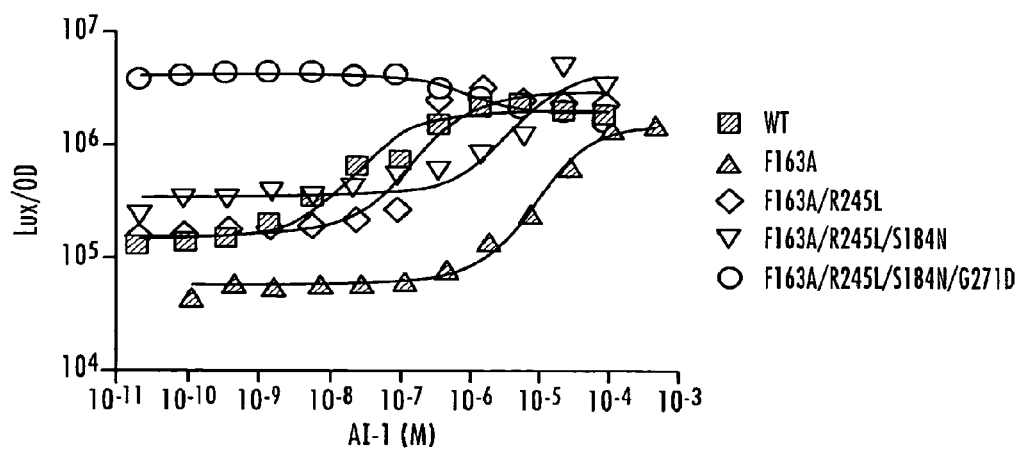

FIGS. 9A-9B. AI-1 Dose-response Curves of the LuxN* Suppressor Mutants. (9A) Light production of the wild-type LuxN, the LuxN* mutants, and LuxN F163A at various AI-1 concentrations. The data were fit with a variable-slope sigmoidal dose-response curve to determine the $EC_{50}$ value for each LuxN* mutant. (9B) Light production of the dark LuxN F163A mutant harboring combinations of LuxN* mutations. Data were fit and AI-1 $EC_{50}$ value was determined as above. An $EC_{50}$ value could not be determined for the quadruple mutant because it is constitutively bright at all AI-1 concentrations.

FIGS. 10A-10B. Two Quorum Sensing Mechanisms For Homoserine Lactone Autoinducer Detection. (10A) LuxN is the *Vibrio Harveyi* transmembrane receptor for autoinducer hydroxybutanoyl homoserine lactone, which requires LuxM synthase for its production. (10B) In *Chromobacterium violaceum*, the synthase CviI is responsible for production of the autoinducer. Autoinducer binds to the cytoplasmic receptor CviR.

Figure 11:
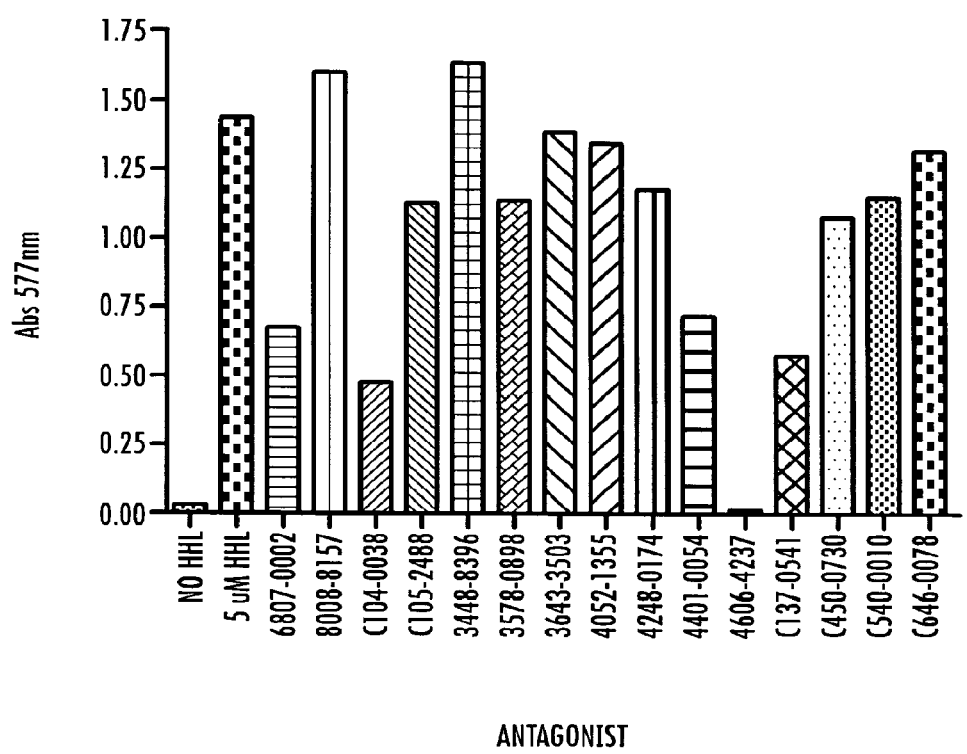

FIG. 11. Antagonist Violacein Screen. Effect of the antagonist molecules on the cytoplasmic LuxR-type receptor (CviR) of *Chromobacterium violaceum*. Receptor inhibition results in loss of production of the purple pigment violacein. Shown are the violacein readouts of the bacteria in the absence (no HHL) and presence (5 μM HHL) of hydroxybutanoyl homoserine lactone (HHL) and in the presence of the fifteen small molecule antagonists shown.

Figure 12:
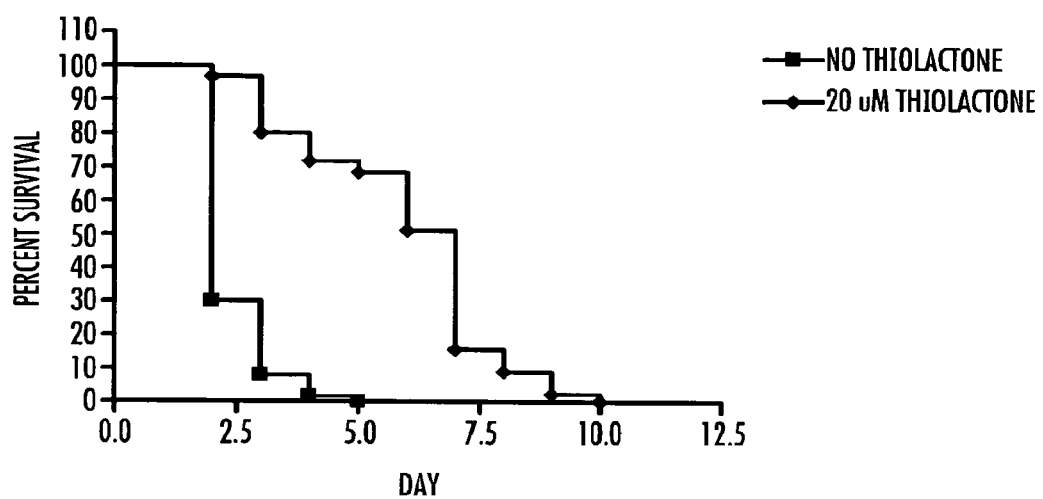

FIG. 12. *C. violaceum* (wild type) Pathogenicity is Inhibited by Thiolactone Antagonist. Survival graphs are shown for *C. elegans* infected with wild type *C. violaceum* with or without a supplement of the thiolactone drug 4606-4237.

Figure 13:
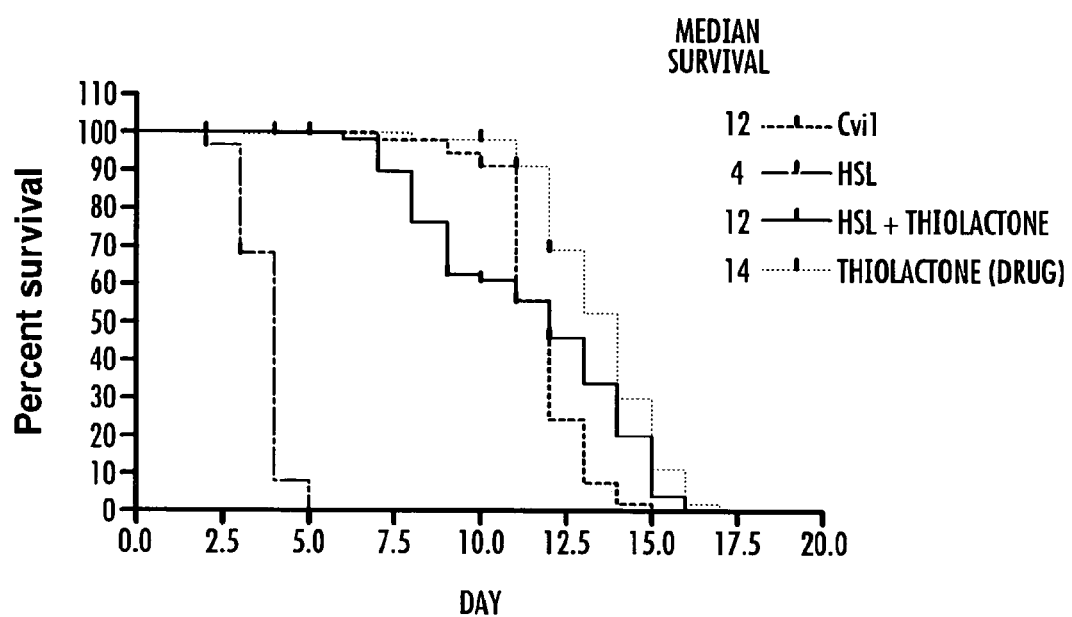

FIG. 13. *C. elegans* Survival Times after Infection with *C. violaceum* Supplemented with Homoserine Lactone, Thiolactone or a Combination of the Two. Survival graphs are shown for the nematode *C. elegans* infected with the synthase mutant strain of *C. violaceum* bacteria in the presence and absence of the homoserine lactone autoinducer and the thiolactone drug 4606-4237.

FIGS. 14A-14B. LuxN Signal Transduction Can Be Described by a Two-State Model. (14A) Wild-type LuxN toggles between two conformations indicated by the open and closed periplasmic domains. At low cell density, when the AI-1 concentration is negligible, LuxN is strongly biased toward its kinase state represented by the open periplasmic structure. At high cell density, in the presence of AI-1 (dark ovals), LuxN is biased toward the phosphatase state represented by the closed periplasmic structure. (14B) This two-state model is represented by a free-energy diagram that describes the two ligand-free forms of the protein as on (open periplasmic domain) or off (closed periplasmic domain). The free energies of these two states are independent of ligand concentration and are represented by horizontal black lines. The free energy of the on state is lower than the free energy of the off state, producing the bias toward the kinase mode at low cell densities (i.e. low autoinducer concentration). The free energy of LuxN in its phosphatase state and bound to ligand (off$_L$) is represented by the descending solid curve. The point at which the free energy of the off$_L$ state equals the free energy of the on state (solid circle) corresponds to the $EC_{50}$ value for AI-1. LuxN mutants identified in the genetic screen that possess increased AI-1 $EC_{50}$ values are represented as on$^-$. Compared to wild-type LuxN, they have lower on state free energies and therefore exhibit larger AI-1 $EC_{50}$ values. By contrast, the three LuxN* mutants that exhibit a bias toward the phosphatase state are represented as on$^+$. These mutants possess higher on state free energies than wild-type LuxN and therefore have decreased AI-1 $EC_{50}$ values. The $EC_{50}$ values of the on and on mutants are represented by the open circles.

Figure 15A:
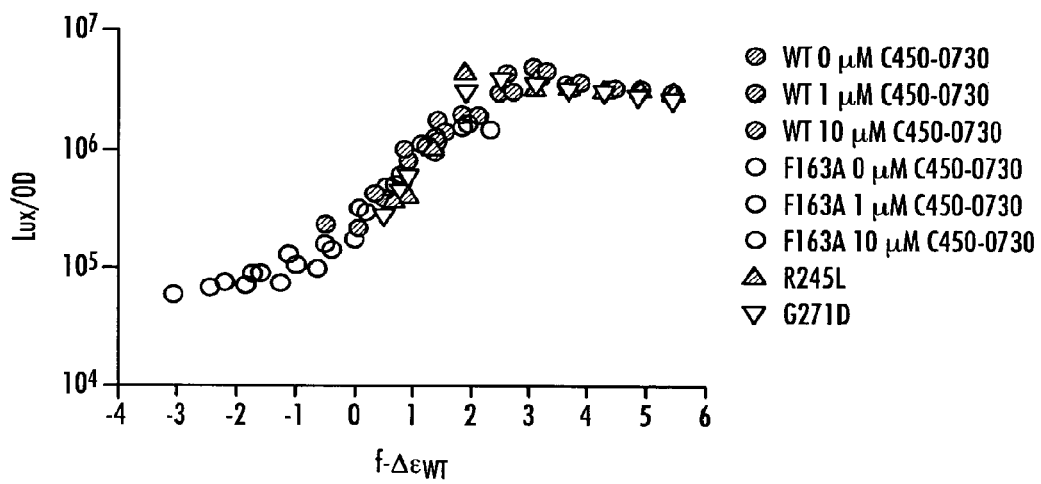
Figure 15B:
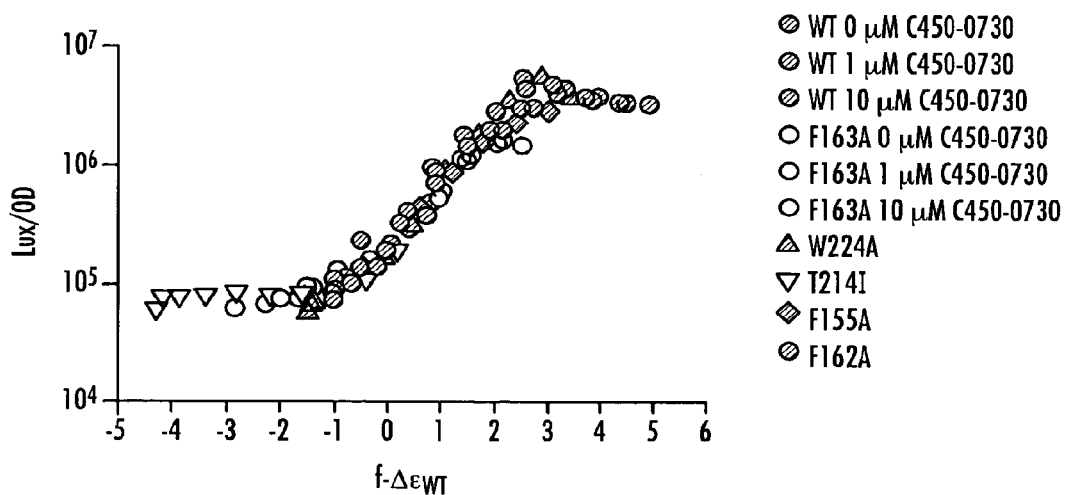

FIGS. 15A-15B. Data Collapse for LuxN*, LuxN Bias, and Combined LuxN*-Bias Mutants. (15A) Collapse of the dose-response data from LuxN* R245L and G271D mutants with the combined wild-type/LuxN F163A antagonist collapse from FIG. 4C. These LuxN* curves were collapsed by adjusting only the bias $\Delta\epsilon - \Delta\epsilon_{WT}$ to +0.5. (15B) Collapse of dose-response curves from representative dark LuxN mutants with the combined wild-type/LuxN F163A antagonist collapse from FIG. 4C. The LuxN W224A and LuxN T214I dose-response curves were collapsed by adjusting only the bias $\Delta\epsilon - \Delta\epsilon_{WT}$ to −1.5 and −4.3, respectively. The LuxN F155A and LuxN F162A dose-response curves were collapsed by adjusting the bias $\Delta\epsilon - \Delta\epsilon_{WT}$ parameter and increasing the $K_{off}^{AI-1}$: for LuxN F155A, $\Delta\epsilon - \Delta\epsilon_{WT} = -1.0$ and $K_{off}^{AI-1} = 10$ nM, for LuxN F162A, $\Delta\epsilon - \Delta\epsilon_{WT} = -1.0$ and $K_{off}^{AI-1} = 100$ nM.

DETAILED DESCRIPTION OF THE INVENTION

The novel strategies described herein are aimed at interfering with the detection of quorum sensing molecules known as autoinducers. Quorum sensing controls expression of traits essential for bacterial virulence. Quorum sensing plays a vital role in the pathogenicity of many bacteria because the ability to act as a coordinated group is essential for bacteria to successfully infect host organisms. Interference with either the production or the detection of autoinducer molecules can abolish bacterial communication and render bacteria non-pathogenic. Thus, the novel methods of the present invention, which interfere with bacterial detection of autoinducer are important in controlling populations of bacteria.

Figure 3A:
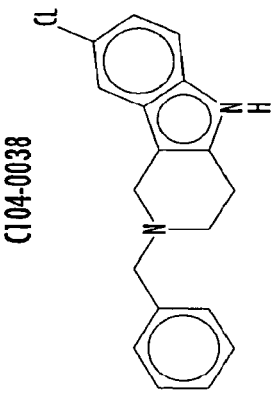
FIGS. 3A-3P. Identifying Data for Fifteen Antagonist Molecules. (3A) Antagonist 6807-0002. (3B) Antagonist 8008-8157. (3C) Antagonist C104-0038. (3D) Antagonist C105-2488. (3E) Antagonist 3448-8396. (3F) Antagonist 3578-0898. (3G) Antagonist 3643-3503. (3H) Antagonist 4052-1355. (3I) Antagonist 4248-0174. (3J) Antagonist 4401-0054. (3K) Antagonist 4606-4237. (3L) Antagonist C137-0541. (3M) Antagonist C450-0730. (3N) Antagonist C540-0010. (3O) Antagonist C646-0078. (3P) Table characterizing the molecules pictured in FIG. 3A-3O.
Figure 3B:
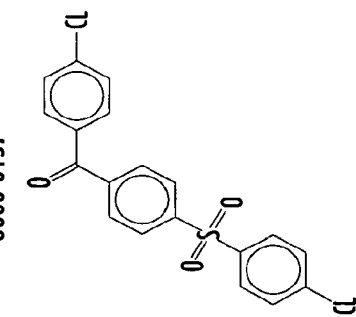
Figure 3C:
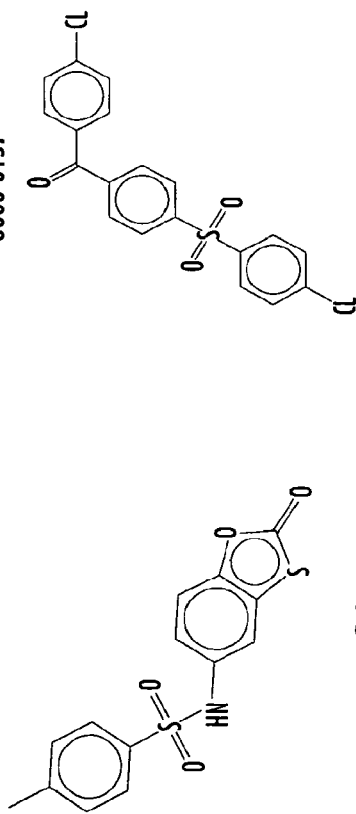
Figure 3E:
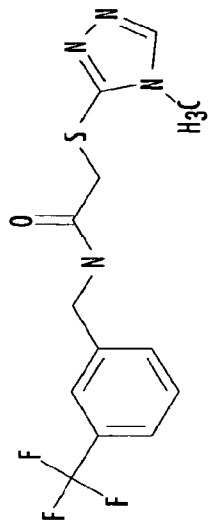
Figure 3D:
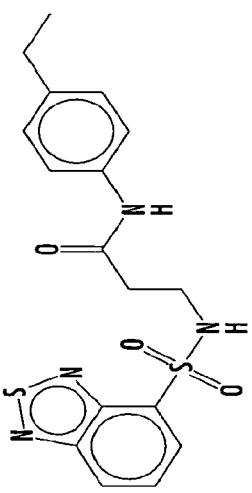
Figure 3G:
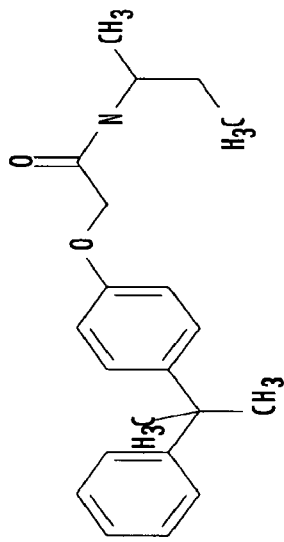
Figure 3I:
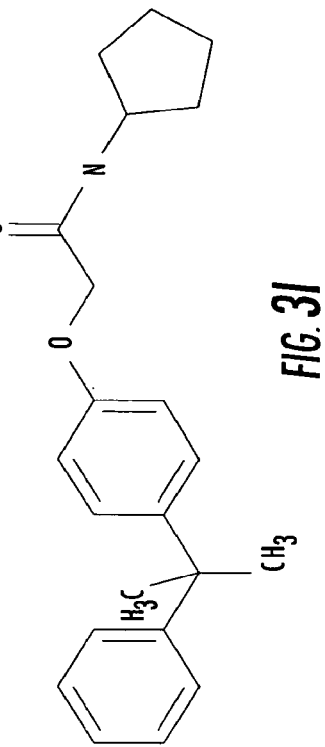
Figure 3F:
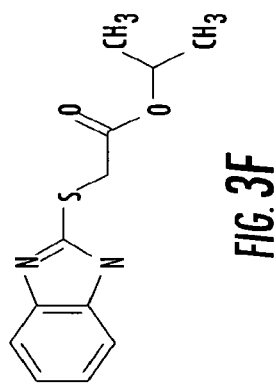
Figure 3H:
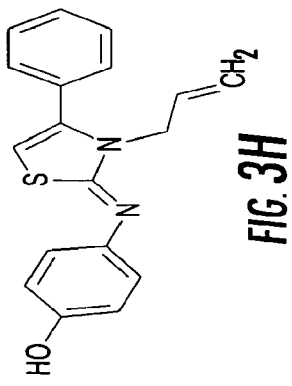
Figure 3J:
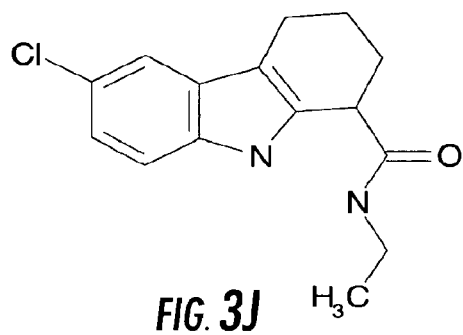
Figure 3K:
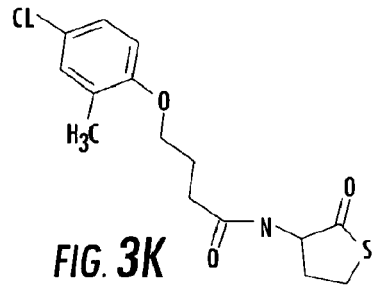
Figure 3L:
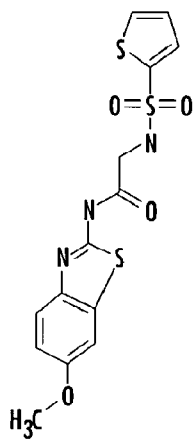
Figure 3M:
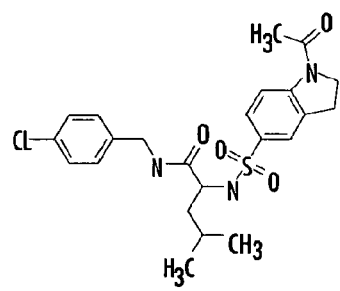
Figure 3O:
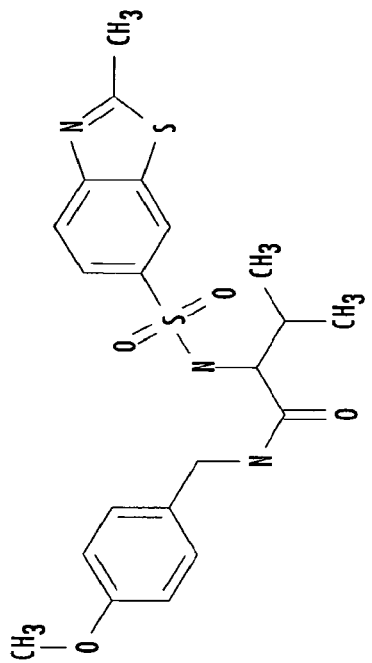
Figure 3N:
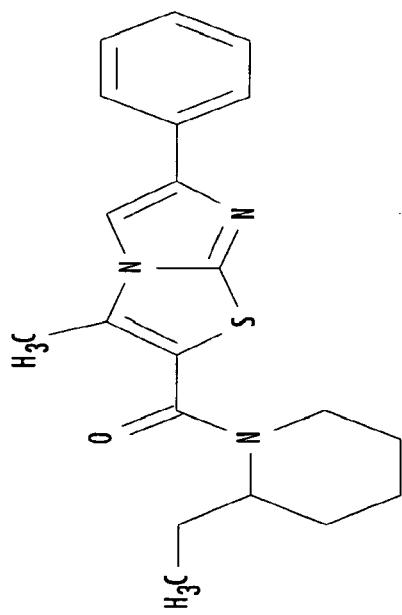

The present invention identifies fifteen small molecules that disrupt detection of acyl-homoserine lactone-type autoinducer in Gram-negative bacteria and thus inhibit quorum sensing mediated processes (FIGS. 3A-3O). These molecules antagonize membrane-bound and cytoplasmic autoinducer receptors. As representative of these two groupings of Gram-negative quorum sensing bacteria, the molecules were demonstrated to act in the model bacterial species *Vibrio harveyi* and *Chromobacterium violaceum* by detecting the quorum sensing mediated activities of bioluminescence and violacein production, respectively. *V. harveyi* is representative of those bacteria that have membrane bound sensor receptor for the autoinducer. *C. violaceum* is representative of those bacteria that have cytoplasmic sensor receptor for the autoinducer (FIGS. 10A-10B).

It is known that inhibitors of quorum sensing function to shut down entire pathogenicity regulons. It has been previously shown that use of bioluminescence as a convenient readout activity is an accurate reporter of the inhibition of all other quorum sensing target genes, e.g., virulence factor production, biofilm genes, type III secretion. Published research of Bassler and others in the field have demonstrated that convenient reporters such as bioluminescence, gfp, or violacein production, are accurate representations of what is happening for all the genes in the regulon.

Nonetheless, pathogenicity was studied in more detail in a model system using *Caenorhabditis elegans* as a model of a host animal infected by pathogenic bacteria. *C. violaceum* was used as a model of pathogenic bacteria capable of quorum sensing-mediated killing of the host. An antagonist molecule identified from a high-throughput chemical library screen protected *C. elegans* from quorum sensing-mediated killing by *C. violaceum* (FIG. 12).

It has previously been shown that the Type III secretion system (TTS) is a quorum sensing mediated activity. TTS systems are specialized secretion apparatuses used by many gram-negative plant and animal pathogens to inject effector virulence factors directly into the cytoplasm of eukaryotic host cells with which they are associated. Once inside the host cell, these effector proteins perform a range of functions that contribute to the propagation of the bacteria. TTS systems have been identified in numerous gram-negative bacterial pathogens, including enteropathogenic *Escherichia coli* and the marine bacteria *Vibrio parahaemolyticus* and *V. harveyi*. In enterohemorrhagic and enteropathogenic *Escherichia coli*, quorum sensing activates TTS at high cell density (in the presence of autoinducer). In contrast, at high cell density, quorum sensing represses TTS in the marine bacteria *V. harveyi* and *V. parahaemolyticus*. (Henke, J. M., and Bassler, B. L. (2004a). J Bacteriol 186, 3794-3805).

Thus, the small molecules of the present invention that have been shown to antagonize the LuxN receptor inhibit quorum sensing activity in *E. coli* at high cell density and make the bacterium avirulent because the bacterium needs to express TTS late in infection to result in virulence. In *Vibrio* infection, where TTS is required at low cell density, adding the antagonist small molecule causes the bacteria to express virulence traits at high cell density. This will make the bacterium avirulent because the antagonist will cause the bacterium to express, during late infection, the traits (TTS) that are actually needed early in infection, thus providing non-optimal conditions for infection, causing a growth disadvantage, and wasting energy.

Thus, in a further embodiment, the invention provides a pharmaceutical composition comprising the small molecule compounds of the present invention (FIGS. 3A-3O), or a pharmaceutically-acceptable salt thereof, and one or more pharmaceutically acceptable carriers, adjuvants or vehicles. The pharmaceutical composition of the invention can be used to treat infections in a warm-blooded animal caused by microorganisms possessing a quorum-sensing mechanism, which comprises administering to the animal a therapeutically effective amount of the pharmaceutical composition of this invention.

The pharmaceutical compositions can be administered by any mode known in the art, including, for example, oral, nasal, topical (including buccal and sublingual) or parenteral (including subcutaneous, intramuscular, intravenous and intradermal) administration. A skilled artisan can determine which form of administration is best and the therapeutic amount in a particular case for balancing the dose needed versus periodic delivery.

Oral administration can include solid dosage forms, such as capsules, tablets, pills, powders, tinctures and granules. In such solid dosage forms, the active compound is generally admixed with at least one inert pharmaceutically acceptable carrier such as sucrose, lactose, or starch. Such dosage forms can also comprise additional substances such as lubricating agents, for example, magnesium stearate. In the case of capsules, tablets and pills, the dosage forms can also comprise buffering agents. Tablets and pills can additionally be prepared with enteric coatings.

Infectious bacteria that use acyl-homoserine lactone quorum sensing strategies to produce virulence include pathogens to humans, animals, and plants. Some pathogens infect marine life and thereafter cause disease in humans who eat or otherwise come into contact with the marine life.

Bacterial infection in humans is facilitated by certain conditions such as burns, wounds, implants or use of a catheter. *Chromobacterium violaceum* is one species that may infect wounds. *Vibrio* may contaminate shellfish and cause food poisoning. Individuals with cystic fibrosis (CF) are plagued by bacterial infection of the lungs. Of the several species of bacteria that infect the lungs, *Pseudomonas aeroginosa* is most problematic.

The invention also provides for a medical device comprising one or more of the compounds shown in FIGS. 3A-3O, wherein the device is supplemented with the compound(s) and the compound is present in a concentration sufficient to disrupt detection of autoinducer-1. The compounds may be coated on the device. As used herein, the term "medical device" means a device having surfaces that contact tissue, blood, or other bodily fluids in the course of their operation. This definition includes within its scope, for example, surgical implants, surgical sutures, wound dressings, extracorporeal devices for use in surgery such as blood oxygenators, blood pumps, blood sensors, tubing used to carry blood and the like which contact blood which is then returned to the subject. The definition includes within its scope endoprostheses implanted in blood contact in a human or animal body such as vascular grafts, stents, pacemaker leads, heart valves, and the like that are implanted in blood vessels or in the heart. The definition also includes within its scope devices for temporary intravascular use such as catheters, guide wires, and the like which are placed into the blood vessels or the heart for purposes of monitoring or repair.

The small molecule compounds of the invention can be used to inhibit bacterial cell growth and biofilm formation on substrates used to manufacture medical devices associated with noninvasive and invasive medical procedures. Such substrates include tubular, sheet, rod and articles of proper shape for use in a number of medical devices such as vascular grafts, aortic grafts, arterial, venous, or vascular tubing, vascular stents, dialysis membranes, tubing or connectors, blood oxygenator tubing or membranes, surgical instruments, ultrafiltration membranes, intra-aortic balloons, stents, blood bags, catheters, sutures, soft or hard tissue prostheses, synthetic prostheses, prosthetic heart valves, tissue adhesives, cardiac pacemaker leads, artificial organs, endotracheal tubes, lenses for the eye such as contact or intraocular lenses, blood handling equipment, apheresis equipment, diagnostic and monitoring catheters and sensors, biosensors, dental devices, drug delivery systems, or bodily implants of any kind. For example, arthroscopic surgery is routinely performed with use of medical devices that minimize the invasiveness of the procedure. Such devices include, for example, ultrathin microfiberoptic endoscopes that offer the laryngologist unique access to the limited spaces of the temporal bone and skull base. In another example, a stent supplemented with a small molecule compound of the invention that deters bacterial infections resulting from the presence of the implanted stent can be constructed. Stents are used to maintain an open lumen in tissues including the tracheo-bronchial system, the biliary hepatic system, the esophageal bowel system, and the urinary tract system. U.S. Pat. No. 5,637,113 issued to Tartaglia, and incorporated herein by reference, teaches a stent with a sheet of polymeric film wrapped around the exterior. With regard to the present invention, the film may be loaded or coated with a small molecule compound or composition of the invention. Alternatively, the material used to manufacture the stent can be impregnated with a small molecule compound or composition of the invention.

A medical device may be further supplemented with, for example, one or more antibodies, analgesics, anticoagulants, anti-inflammatory compounds, antimicrobial compositions, cytokines, drugs, growth factors, interferons, hormones, lipids, demineralized bone or bone morphogenetic proteins, cartilage inducing factors, oligonucleotides polymers, polysaccharides, polypeptides, protease inhibitors, vasoconstrictors or vasodilators, vitamins, minerals, stabilizers and the like. Supplemented, as used herein, includes medical devices that are impregnated, infused, coated, covered, layered, permeated, attached or connected with a small molecule compound or composition of the invention. Methods for immobilizing biomaterials to a medical device are discussed in U.S. Pat. No. 5,925,552, which is incorporated herein by reference. Additional methods of coating surfaces of medical devices with antimicrobial compositions are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind antibiotics); U.S. Pat. No. 5,013,306 (laminating an antibiotic to a polymeric surface layer of a medical device); and U.S. Pat. No. 4,952,419 (applying a film of silicone oil to the surface of an implant and then contacting the silicone film bearing surface with antibiotic powders). U.S. Pat. No. 5,902,283 further discloses a method for coating a medical device with an antimicrobial agent such that the agent penetrates the exposed surfaces of the device and is impregnated throughout the material of the device.

It is further envisioned that the small molecule compounds or compositions of the invention can be used to aid wound repair. For example, U.S. Pat. No. 6,117,485 describes a foaming tissue sealant for treating wounded tissue in a subject. The sealant can be formulated to include a compound or composition of the invention. The sealant is useful for significantly diminishing or preventing blood or fluid loss from injured tissues, organs or blood vessels, while also providing a barrier to infection.

Another quorum sensing activity is biofilm formation. Biofilms are communities of bacterial cells adhered to surfaces. Biofilms are highly problematic in industrial processes such as clogging of cooling towers in manufacturing plants. The novel strategies of the present invention prevent or disrupt biofilms by interfering with quorum sensing.

In another embodiment, the invention provides a method of removing a biofilm from a surface that comprises treating the surface with a compound of the invention. The surface is preferably the inside of an aqueous liquid distribution system, such as a drinking water distribution system or a supply line connected to a dental air-water system, where removal of biofilms can be particularly difficult to achieve. The compound is preferably applied to the surface either alone or together with other materials such as conventional detergents or surfactants.

A further embodiment of the invention is an antibacterial composition comprising a small molecule compound of the invention together with a bacteriocidal agent. In the antibacterial compositions, the compound of the invention helps to remove the biofilm while the bacteriocidal agent kills the bacteria. The antibacterial composition is preferably in the form of a solution or suspension for spraying and/or wiping on a surface.

In yet another aspect, the invention provides an article coated and/or impregnated with a compound of the invention in order to inhibit and/or prevent biofilm formation thereon. The article is preferably composed of plastic with the compound of the invention distributed throughout the material.

It is further envisioned that the small molecule compounds or compositions of the invention can be used to inhibit bacterial cell growth and biofilm formation in or on products or devices used for personal hygiene. Soap, toothpaste, dental floss, laundry detergent or moisturizing lotion are examples of consumer products that would benefit from the inclusion of the small molecule compounds or composition of the invention. In addition, such a compound or composition can be included in a personal hygiene device such as a toothbrush, tongue depressor, or any other such device which comes in contact with a tissue.

Thus, the invention includes introduction of one or more small molecules of the invention into an environment where it is desired to prevent bacteria from acting communally in an undesirable activity such as in production of biofilms or virulence. Introduction of the small molecules of this invention is also contemplated as treatment where undesirable bacterial communities are already established. The particular quantity of the small molecule for prevention or treatment is to be determined experimentally by methods known to those skilled in the art. An example provided herein for guidance involves prevention of virulent bacterial activity in the animal model *Caenorhabditis elegans*.

Quorum sensing, a process of bacterial cell-cell communication, relies on production, detection, and response to autoinducer signaling molecules. LuxN, a nine transmembrane domain protein from *Vibrio harveyi*, is the founding example of membrane-bound receptors for acyl-homoserine lactone (AHL) autoinducers. Previously, nothing was known about signal recognition by membrane-bound AHL receptors. Using mutagenesis and suppressor analyses, the AHL-binding domain of LuxN has now been characterized. To extract signaling parameters, a strong LuxN antagonist was exploited, one of the fifteen small-molecule antagonists that were identified. Also identified as antagonists were phenoxy-acetamides, e.g., N-cyclopentyl-2-(4-(2-phenylpropan-2-yl)phenoxy) acetamide and N-sec-butyl-2-(4-(2-phenylpropan-2-yl)phenoxy) acetamide.

Figure 1A:
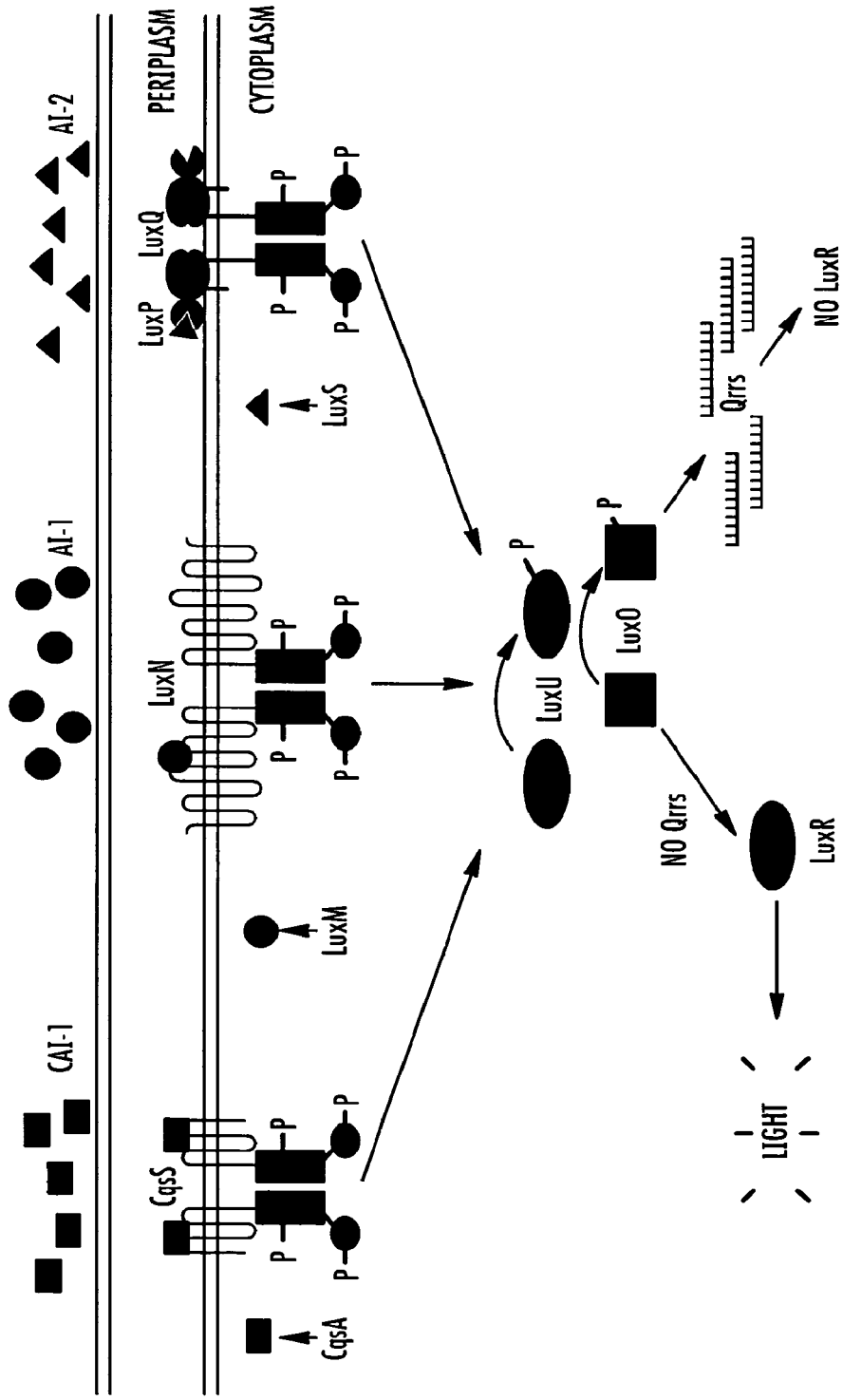
FIGS. 1A-1B. The *V. harveyi* Quorum-Sensing Circuit and the LuxN Trans-Membrane Domain. (1A) CAI-1 is (S)-3-hydroxytridecan-4-one (squares), AI-1 is 3-hydroxybutanoyl homoserine lactone (circles), and AI-2 is (2S,4S)-2-methyl-2,3,3,4-tetrahydroxytetrahydrofuran-borate (triangles), and they are synthesized by CqsA, LuxM, and LuxS, respectively. At low cell densities, in the absence of appreciable autoinducer, CqsS, LuxN, and LuxQ act as kinases funneling phosphate via LuxU to LuxO (arrows). Phospho-LuxO activates expression of the qrr genes; the Qrr sRNAs (comb shapes) are transcribed and they bind to and facilitate the degradation of the mRNA encoding LuxR. Without LuxR, there is no quorum sensing, and thus no light production. At high cell density, in the presence of autoinducers, the receptors act as phosphatases, draining phosphate from LuxO via LuxU. Transcription of the qrr genes is terminated, the LuxR mRNA is stabilized, and LuxR protein is produced. By activating and repressing a variety of genes, LuxR facilitates the transition of the cells into quorum-sensing mode. One operon activated by LuxR at high cell density encodes luciferase, so in the presence of autoinducers, *V. harveyi* produces light. (1B) The cartoon depicts the putative topology of the N-terminal region of LuxN (residues 1-303 of SEQ ID NO:1). Amino acids in the circle, when mutated, confer a dark phenotype. Amino acids in the squares denote sites where mutations enhance sensitivity of LuxN to AI-1. The amino acid in the triangle represents the LuxN* suppressor mutation that prevents C450-0730 antagonism.
Figure 1B:
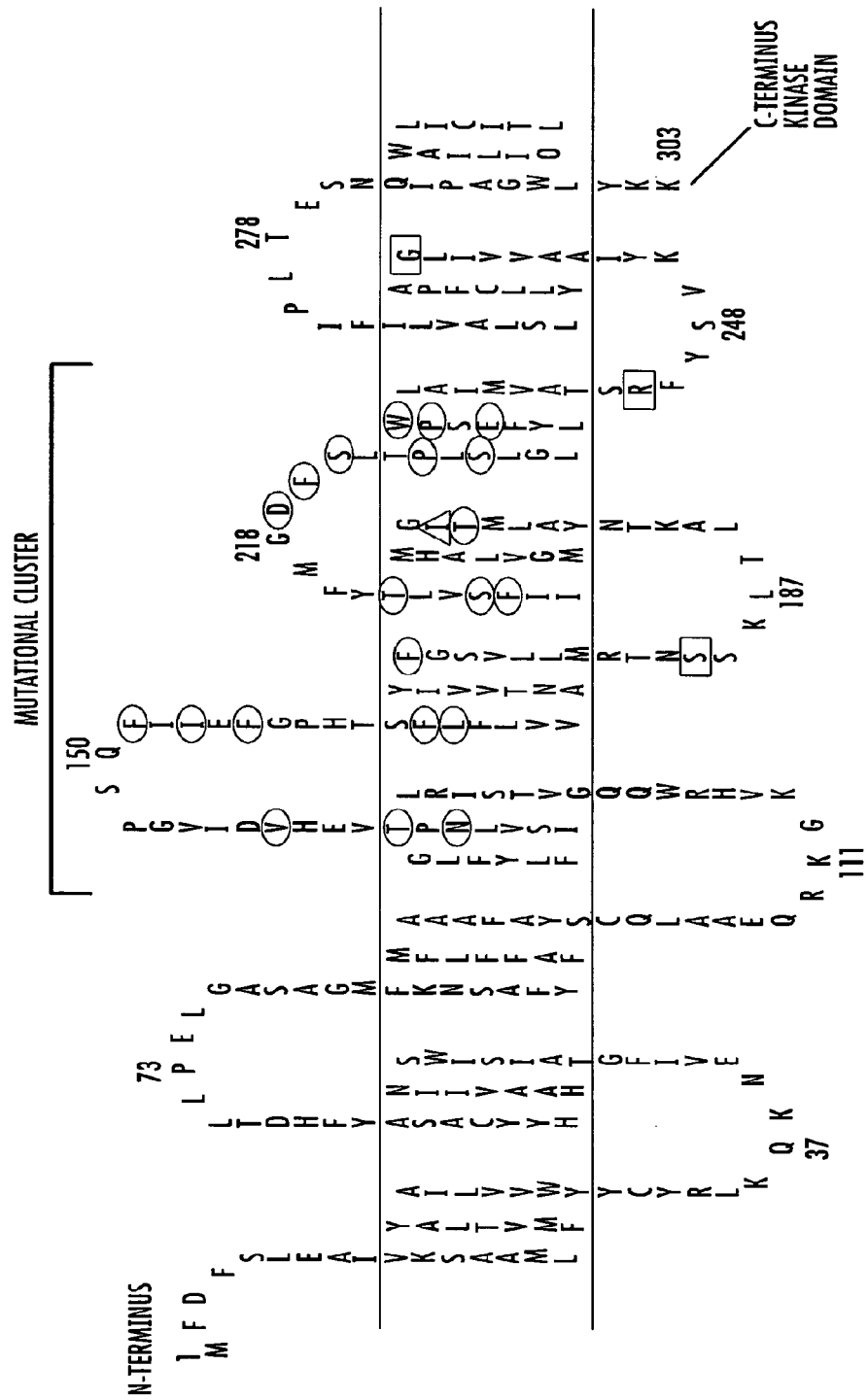

From membrane-topology analysis, it would appear that LuxN is bound to the bacterial inner-membrane by nine transmembrane (TM) spanning helices (FIG. 1B). From reporter-protein fusion analyses, it would appear that the N-terminus of LuxN is on the periplasmic side of the bacterial inner-membrane, while the histidine-kinase portion of LuxN resides in the cytosol (Jung et al., 2007). Therefore, LuxN contains four periplasmic loops and four cytosolic loops connecting the nine transmembrane domain (TM) segments (FIG. 1B). By analogy to homologous membrane-bound sensor kinases, LuxN is believed to assemble into homodimers.

To locate the AI-1 binding domain of LuxN, a genetic screen was performed to identify luxN mutants encoding proteins incapable of properly responding to AI-1 (Example 1). All of the identified amino-acid mutations that affect AI-1 signaling cluster in TM helices near the periplasmic face, or are located within periplasmic loops, indicating that LuxN most likely binds AI-1 on the periplasmic side of the membrane (FIG. 1B). The results indicated that the LuxN AI-1 binding domain is composed of TM helices 4, 5, 6, and 7 as well as the intervening periplasmic loops 2 and 3.

The large number of mutations identified in this work that affect AI-1 binding suggest that LuxN makes multiple contacts with AI-1. Further supporting our conclusion that TM4, TM5, TM6, and TM7 and periplasmic loops 2 and 3 encode the AI-1 binding domain of wild-type LuxN, a LuxN homolog was recently discovered that lacks the first 80 amino acids, which encode TM1, TM2, and periplasmic loop 1, indicating that this region of LuxN is dispensable for AI-1 binding and signaling (FIG. 2A-H and NCBI database). This truncated LuxN homolog retains all of the critical regions identified in our identified AI-1 binding domain, indicating that this LuxN variant can still respond to an autoinducer molecule (FIGS. 2A-2H). Interestingly, the most highly conserved domain in LuxN is centered at position P226, and contains a PPAL motif that is 100% conserved among all known LuxN homologs (FIGS. 2A-2H). Both proline residues of this motif were identified as critical for LuxN signaling by our random mutagenesis screen. Therefore, we deduce that the PPAL motif is essential for LuxN signal transduction.

Sequence alignment comparison of *V. harveyi* LuxN with other LuxN homologs confirmed that the homologs have conserved binding pockets that accommodate an AHL-type ligand and that likewise accommodate the small molecule compounds of this invention (FIGS. 2A-2H). These small molecules antagonize a broad spectrum of AHL type receptors.

A high-throughput chemical screen was used to identify the set of small molecules that were specifically demonstrated to antagonize the LuxN/AI-1 interaction in the model system of *V. harveyi* (Example 4). All of these LuxN antagonist molecules have $IC_{50}$ values in the low micromolar range, and, based on competition assays and genetic evidence, the most potent LuxN antagonist competes for the AI-1 binding site. These antagonists provided a molecular tool with which to further probe the AI-1 binding pocket and characterize the signaling properties of *V. harveyi* LuxN.

Figure 4A:
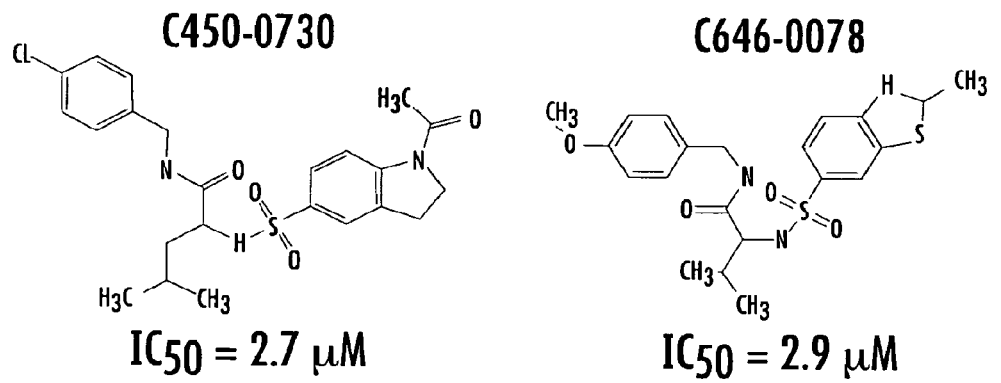
FIGS. 4A-4C. Molecules that Antagonize LuxN-AI-1 Binding or Signaling. (4A) Structures and designations of five molecules that inhibit LuxN signaling in response to AI-1. The $IC_{50}$ value for each antagonist molecule is given below its structure. (4B) Light production from wild-type LuxN and LuxN F163A was measured at the specified AI-1 concentrations in the presence of 0 µM, 1 µM, and 10 µM C450-0730. Data were fit as described above. (4C) The light production values in panel B were collapsed as a function of $f - \Delta \epsilon_{WT}$ as described in Experimental Procedures. $f$ is the ligand-dependent free-energy difference between the kinase active (on) and kinase inactive (off) states of LuxN, and $\Delta \epsilon_{WT}$ is the wild type value of $f$ in the absence of ligand. The binding parameters used are as follows: $K_{off}^{AI-1}=1$ nM, $K_{on}^{AI-1}=1$ mM, $K_{off}^{C450-0730}=1$ mM, $K_{on}^{C450-0730}=500$ nM. The collapse was obtained by using $\Delta \epsilon - \Delta \epsilon_{WT} = 3.2$ for the LuxN F163A mutant.
Figure 4A:
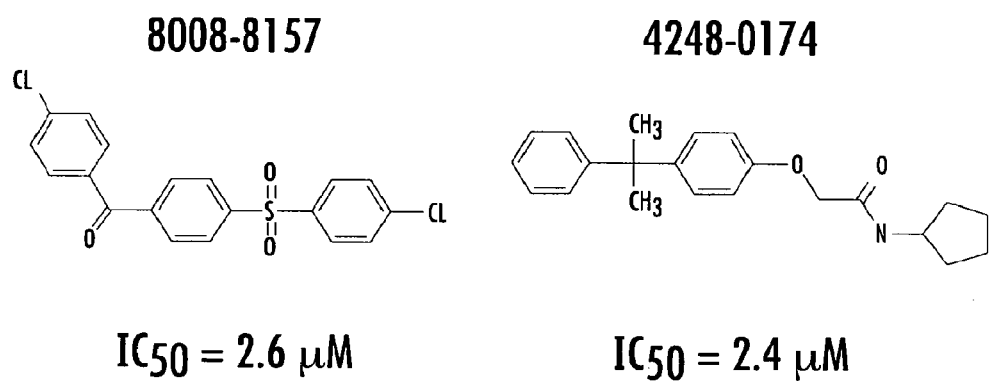
Figure 4A:
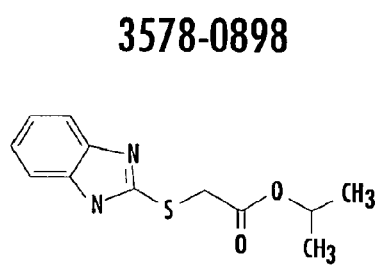
Figure 4B:
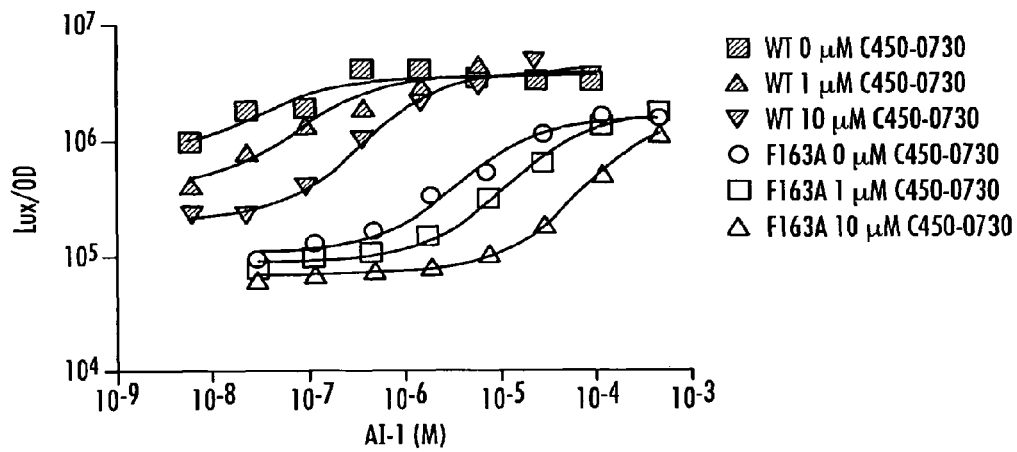
Figure 4C:
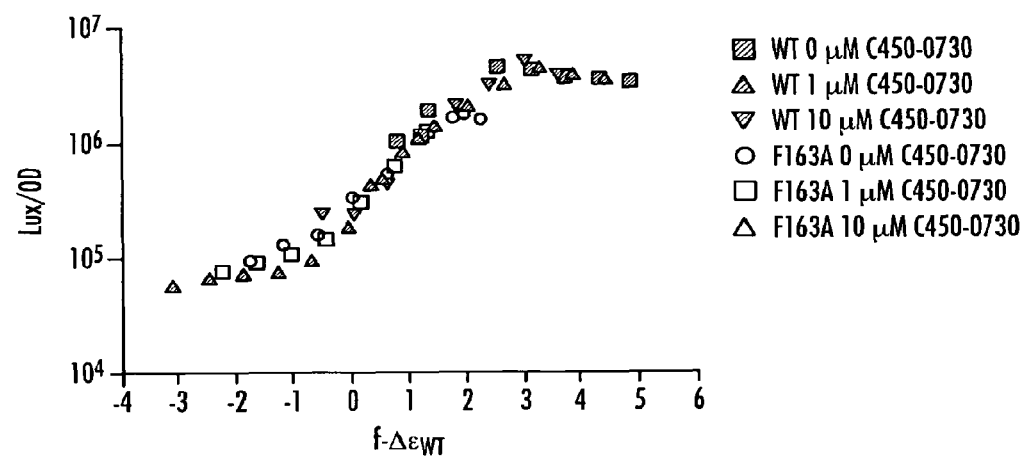

These are the first antagonist molecules that target an AHL membrane-bound sensor kinase. Importantly, the antagonists identified by this screen are not similar in structure to AI-1 (see, for example, FIG. 4A). Therefore, it is unlikely that rational-design experiments would have predicted these molecules as AHL antagonists. To explore whether the antagonists competed with AI-1 for binding to LuxN, we performed an antagonist-suppressor screen, and identified LuxN* I209F, which is not antagonized by C450-0730 (Example 6). Importantly, this mutation lies on the periplasmic side of TM 6, in the center of the proposed AI-1 binding domain, consistent with the possibility that C450-0730 competes for the AI-1 binding site (though the LuxN* mutation I209F does not affect AI-1 signaling). The AI-1 dose-response curves in the presence of different concentrations of C450-0730 for both wild-type LuxN and LuxN F163A provided a good data collapse indicative of competitive inhibition (FIGS. 4B and 4C). Combined, these results led to the conclusion that the C450-0730 antagonist is competing for the AI-1 binding pocket of LuxN. Because the LuxN* I209F mutation only affects the antagonistic ability of C450-0730, but does not interfere with AI-1 signaling, we deduce that C450-0730 makes at least some contacts with LuxN that are distinct from those made by AI-1.

In order to answer the question whether mutations in LuxN could shift the free-energy bias between receptor kinase and phosphatase states, a model was devised, shown schematically in FIG. 14. We propose that each LuxN can exist in any of four states: kinase (on) or phosphatase (off), with ligand bound or unbound. Receptor activity is determined by the thermal equilibrium among these states, characterized by the free-energy difference $f$ between the on and off states of LuxN (see Experimental Procedures). Within the model, the measured output, bioluminescence, is the same unknown function off for all strains, reflecting the fact that bioluminescence depends only on receptor activity, which at equilibrium depends only on f. The model predicts that mutations can cause EC50 to increase or decrease depending on the sign of the shift in $\Delta\epsilon$ the free-energy bias between kinase and phosphatase states. Indeed, the model is nicely supported by the data collapse in FIG. 4C, where the bioluminescence for the LuxN F163A mutant collapses well with wild type assuming only a shift in $\Delta\epsilon$. More generally, we have found that the bioluminescence data for many of our LuxN mutants collapse well with the combined wild-type and LuxN F163A data, allowing us to deduce changed $\Delta\epsilon$ values and in some cases also changed binding affinities (FIG. 15). This analysis supports a close functional analogy between LuxN and *E. coli* chemotaxis receptors, and suggests the general relevance of two-state, free-energy models for bacterial sensor kinases.

Little was known about how membrane-bound kinase proteins, like LuxN, detect AHLs. Our mutagenesis strategy, showing that LuxN most likely binds AI-1 on the periplasmic side of the membrane, indicates that AI-1 is released from *V. harveyi*, accumulates in the extracellular space, and subsequently triggers the LuxN quorum-sensing cascade. This mechanism is distinct from the previously characterized LuxR-type AHL-signaling mechanism. Typically, LuxR-type AHL receptors require significant intracellular AHL concentrations for folding. Thus, at low cell densities the LuxR proteins do not fold properly and are degraded, so quorum sensing does not occur. Degradation of the LuxR-type proteins in the absence of the AHL signal is presumed to be a mechanism preventing premature activation of quorum sensing in canonical LuxR-AHL systems. Apparently, *V. harveyi* has evolved a distinct mechanism to circumvent short circuiting its quorum-sensing pathway, namely by compartmentalizing the cytosolic production of AI-1 in a location inaccessible to the periplasmic sensing domain of LuxN. This spatial uncoupling of AI-1 production from AI-1 binding allows *V. harveyi* to exclusively monitor extracellular levels of AI-1. It must be noted that *V. harveyi* has three quorum-sensing circuits, all of which have similar architectures. Thus, all three systems have signal production spatially uncoupled from signal detection (FIG. 1A).

Furthermore, through quantitative analysis it was revealed that, unlike the paradigmatic two-state chemotaxis receptors which spend roughly equal time in the active and inactive states for maximum sensitivity to ligand, the quorum-sensing receptor LuxN spends ~96% of its time in the active/kinase state and requires establishment of a threshold concentration of autoinducer to inactivate it. Remarkably, although the chemotaxis and LuxN receptors are homologous, they solve fundamentally different biological problems by operating in different regimes. Chemotaxis, a system tuned for sensitivity, allows instantaneous alterations in behavior in response to small fluctuations in signal concentration. Quorum sensing, by contrast, a system built to ignore small perturbations, initiates a slow, all-or-nothing commitment program only upon reaching a signal threshold. We suggest that the distinct design properties inherent in the quorum sensing and chemotaxis signaling systems have evolved to optimally solve very different biological problems.

The following examples set forth the general procedures involved in practicing the present invention. To the extent that specific materials are mentioned, it is merely for purposes of illustration and is not intended to limit the invention. Unless otherwise specified, general molecular biology procedures, such as those set forth in Sambrook et al., Molecular Cloning, Cold Spring Harbor Laboratory (1989) (hereinafter "Sambrook et al.") or Ausubel et al. (eds) Current Protocols in Molecular Biology, John Wiley-Sons (1998) (hereinafter "Ausubel et al.") were used.

Example 1

Identification of LuxN Mutants with Defective Responses to AI-1

The aim of this study was to determine how LuxN and AI-1 interact in order to understand how trans-membrane receptors couple AHL signaling to changes in gene expression. However, as is the case for most histidine sensor kinases, the complex trans-membrane topology of LuxN makes direct structural analysis extremely difficult. Therefore, to pinpoint the AI-1 binding site in the periplasmic domain of LuxN, directed mutagenesis of the 1 kb region of luxN encoding the membrane-binding domain was performed using error-prone PCR. The library of luxN mutants generated by this approach was cloned into a version of the luxN gene lacking this region to regenerate full-length luxN. The mutant library was introduced into the double sensor mutant JMH625 (luxN luxQ), which has a bright phenotype because there is no flow of phosphate to LuxO (FIG. 1A). The CAI-1-CqsS system is intact in the strain used for this screen. Because saturating levels of CAI-1 are always present in these experiments, CqsS exists as a phosphatase and thus does not contribute in funneling phosphate to LuxO. Thus it is reasonable that when a wild-type copy of luxN is introduced into this strain in the presence of AI-1, it will remain bright because binding of AI-1 to LuxN induces phosphatase activity. However, if a mutant luxN allele encoding a LuxN protein that is incapable of binding or responding to AI-1 is introduced, it will confer a dark phenotype due to high levels of LuxN auto-phosphorylation and phospho-transfer to LuxO (FIG. 1A).

Approximately 30,000 luxN mutants were screened for those alleles causing a reduction in bioluminescence. Ten alleles were confirmed to produce dark phenotypes. These luxN genes were sequenced to identify the mutations (Table 2, FIG. 1B). Several candidates contained multiple mutations, and these mutations were uncoupled by site-directed mutagenesis to produce genes encoding LuxN proteins with single amino-acid substitutions (Table 2). Interestingly, in the case of LRS6 two of the uncoupled mutations independently caused dark phenotypes (Table 2). Further analyses were carried out on LuxN mutants containing only single amino-acid changes.

The mutations conferring dark phenotypes cluster to the periplasmic region of TMs 4, 5, 6, and 7 and periplasmic loops 2 and 3 (FIG. 1B circles) suggesting that the AI-1 binding site resides there. To explore this hypothesis further, the 11 available LuxN homologs were compared and every 100% conserved amino acid was replaced as well as the other most highly conserved amino acids within this region with alanine, and were screened as above. This analysis produced an additional 20 mutants defective in response to AI-1. (Table 1, FIG. 1B).

The LRS5 mutation, which confers a dark phenotype, is a single base-pair deletion at position 634 causing a premature stop codon at amino-acid residue 213 (Table 2). This mutation was unexpected because the premature stop codon would lead one to believe that the kinase domain of LuxN should not be synthesized, making it unclear how this mutation could confer a dark phenotype. To investigate this, a FLAG-epitope tag was fused to the C-terminus of this mutant LuxN and the protein was probed by western blot analysis. This analysis indicated that a truncated version of LuxN lacking approximately the first 220 amino acids is synthesized (data not shown). It appears that an alternative ribosome binding site exists downstream of the LRS5 deletion, enabling translation of a truncated form of LuxN. Because this truncation eliminates almost the entire proposed AI-1 binding domain from LuxN, only the cytoplasmic kinase domain is produced which, because it is unable to bind to AI-1, constitutively acts as a kinase causing a dark phenotype.

Example 2

LuxN Mutant Phenotypes

To characterize the signaling capabilities of the single-amino-acid-substituted LuxN mutants, a series of quantitative phenotypic analyses were carried out. First, we measured bioluminescence in stationary-phase cultures of strains carrying either wild-type luxN or each luxN allele conferring a dark phenotype. The bioluminescence produced by the strain with wild-type luxN was set at 100% (FIG. 6A). As negative controls, two luxN mutants harboring wild-type phenotypes (LuxN L138A and LuxN E154Q) which were randomly isolated from the screen were also included in the analysis and they produced the wild-type level of bioluminescence (FIG. 6A). By contrast, the LuxN mutants F151A, I153F, F155I, L166R, T214I, F220A, P226T, and S232N exhibited at least an 80% reduction in bioluminescence relative to wild type (FIG. 6A). To confirm that the dark phenotypes did not stem from increased LuxN protein levels, FLAG-epitope tags were incorporated at the C-terminus of a representative subset of the LuxN mutants shown in FIG. 6A as well as wild-type LuxN. Western blot showed that there were no differences in protein production (data not shown).

We reasoned that the LuxN mutants conferring dark phenotypes must be acting as kinases at high cell density, resulting in continued flow of phosphate through the quorum-sensing circuit. This in turn, should manifest itself in elevated qrr expression at high cell density (FIG. 1A). To test this idea, quantitative real-time PCR was performed and Qrr4 transcript levels were measured in each of the luxN mutant strains described above. As controls, Qrr4 transcript levels were measured in the wild type and the bright control strains, LuxN L138A and LuxN E154Q, and we found that indeed, in these three strains, Qrr4 levels are low, consistent with these LuxN proteins acting as phosphatases at high cell density (FIG. 6B). However, the luxN mutants exhibiting dark phenotypes (FIG. 6A) all have significantly increased Qrr4 transcript levels (10 to 30-fold higher than wild type) (FIG. 6B). This result confirms that the decrease in bioluminescence observed in the dark LuxN mutants is the direct result of an alteration in signaling through the LuxN quorum-sensing pathway.

Example 3

AI-1 Dose-Response Curves

Two possible mechanisms were considered underlying the dark LuxN phenotypes. First, a particular mutation could abolish AI-1 binding. If so, this type of mutation would cause LuxN to act as a kinase at high cell density in the presence of AI-1. Alternatively, a mutation could allow AI-1 binding, but disrupt the ability of LuxN to transduce the signal to the cytoplasm. We first determined which LuxN mutant proteins could bind AI-1 by measuring the AI-1 dose-response of each LuxN missense mutant. For this, *V. harveyi* strain HLS253 ΔluxMN, ΔluxPQ, ΔluxS was used. *V. harveyi* HLS253 is constitutively bright because the luxN and luxPQ genes, encoding the quorum-sensing receptors, have been deleted. Also, *V. harveyi* HLS253 does not produce AI-1 or AI-2, due to the luxM and luxS deletions, respectively. Introduction of a wild-type copy of luxN into *V. harveyi* HLS253 confers a dark phenotype because, in the absence of AI-1, LuxN acts as a constitutive kinase. However, addition of exogenous AI-1 to HLS253 harboring a wild-type copy of luxN induces bioluminescence. Introduction of a luxN mutant encoding a LuxN protein incapable of binding AI-1 or incapable of signaling the AI-1 binding event to the cytoplasm will confer a dark phenotype to HLS253. And, such defects will cause the LuxN proteins to remain as kinases even in the presence of AI-1. By contrast, if a particular LuxN mutant is introduced that is capable of binding AI-1, even with lower affinity than wild-type LuxN, these LuxN proteins will switch to phosphatase activity following the addition of sufficient AI-1, and bioluminescence will be induced.

To determine AI-1 $EC_{50}$ values, wild-type LuxN and each LuxN mutant were assayed for response to AI-1 at concentrations ranging from 24 pM to 500 µM. A subset of the dose-response curves is shown in FIG. 7A, and the remainder of the $EC_{50}$ data is provided in Table 1. The $EC_{50}$ for wild-type LuxN binding to AI-1 is 23 nM. The control mutants, LuxN L138A and LuxN E154Q, as expected, have $EC_{50}$ values of 30 nM and 55 nM, respectively, similar to wild-type LuxN (Table 1). Many of the LuxN mutants have drastically increased $EC_{50}$ values (Table 1). For example, LuxN I153F, F155A, F162A, T206A, and S232A have $EC_{50}$ values of 130 nM, 580 nM, 93 µM, 310 nM, and 400 nM, respectively (FIG. 7A). In five cases, LuxN L166R, F202A, S205P, P226T, and E233A, the mutants conferred a dark phenotype to *V. harveyi* even at 500 µM AI-1 (FIG. 7B) and therefore $EC_{50}$ values were unable to be assigned. Nonetheless, we successfully determined the AI-1 $EC_{50}$ values for 25 of the 30 LuxN mutants that conferred a dark phenotype. We conclude that LuxN mutant proteins that produce measurable $EC_{50}$ values, albeit higher than wild type, can bind AI-1 at least with some capacity.

Example 4

Identification of LuxN Antagonists

To probe the LuxN/AI-1 interaction further, small molecules were identified that interfere with *V. harveyi* quorum sensing by disrupting the binding of AI-1 to LuxN. To do this, a high-throughput chemical screen was carried out using the chemicals collection of the Broad Institute (Massachussetts, USA), which identified small molecules that specifically antagonize LuxN signaling in *V. harveyi*. The *V. harveyi* strain, JMH624 ΔluxPQ, ΔluxM, which lacks the AI-2 receptor, LuxPQ, as well as the AI-1 synthase, LuxM, was used for the antagonist screen. *V. harveyi* JMH624 is dark because there is no AI-2 receptor and the lack of AI-1 causes LuxN to act as a kinase (FIG. 1A). However, following exogenous addition of 20 nM AI-1, bioluminescence is induced because LuxN switches to phosphatase mode. Potential antagonist molecules were tested for the ability to reduce bioluminescence of *V. harveyi* JMH624 in the presence of 20 nM AI-1. To eliminate molecules causing general toxicity and those that interfere with luciferase or other downstream components of the quorum-sensing bioluminescence pathway, a second screen was carried out using a *V. harveyi* ΔluxN, ΔluxS control strain, JMH610. *V. harveyi* JMH610 lacks the AI-1 receptor LuxN and the AI-2 synthase, LuxS. In this case, because of the lack of AI-2, LuxQ acts as a kinase, and *V. harveyi* JMH610 is dark. However, following exogenous addition of AI-2, bioluminescence is induced because LuxQ switches to phosphatase mode (FIG. 1A). Any molecule that reduced bioluminescence in both JMH610 in the presence of AI-2 and JMH624 in the presence of AI-1 was eliminated from further analysis. Approximately 35,000 low-molecular-weight compounds were screened for specific inhibition of bioluminescence through the LuxN quorum-sensing pathway; 45 molecules were selected for further analysis, and a representative subset of these molecules with varying levels of antagonistic activity is shown in FIG. 4A. For example, molecule C450-0730 has an $IC_{50}$ value of 2.7 µM while a weaker antagonist, 3578-0898 has an $IC_{50}$ of 62.3 µM. Interestingly, the molecular cores of two of the strongest LuxN antagonists, C450-0730 and C646-0078, are very similar (FIG. 4A). A larger subset of these molecules is shown in FIG. 8.

It was not initially known whether the potent LuxN antagonist, C450-0730, was competing for the LuxN AI-1 binding site. To examine this, AI-1 $EC_{50}$ values were determined in the presence of 0 µM, 1 µM, and 10 µM C450-0730. Our rational is that, if C450-0730 competes with AI-1 for binding, the AI-1 $EC_{50}$ value should increase with increasing concentrations of C450-0730. Indeed, this is the case, as the AI-1 $EC_{50}$ values are 23 nM, 76 nM, and 376 nM at 0 µM, 1 µM, and 10 µM C450-0730, respectively (FIG. 4B). Indeed, the AI-1 dose-response curves at these three C450-0730 concentrations can be collapsed onto a single curve, consistent with competitive inhibition (FIG. 4C and Experimental Procedures). The principal underlying the data collapse is that there is a fixed (albeit initially unknown) quantitative relation between measured bioluminescence and the free-energy difference between the active and inactive configurations of LuxN (Keymer et al., 2006). Therefore, all the dose-response curves should reproduce this same relation, i.e. the curves should "collapse" when bioluminescence is plotted versus free-energy difference. However, to plot the data this way, it is necessary to know how to relate ligand concentrations to free-energy differences, which means that it is necessary to know the ligand dissociation constants $K_D$ for both the active and inactive configurations of LuxN. In practice, we iteratively improve our estimates for $K_D$ values by attempting to collapse the dose-response curves and infer the true values from the best data collapse. This is a reliable procedure here, since the dose-response curves contain more data than the number of unknown $K_D$ values. A major benefit of collapsing the data in this way is that it allows us to deduce the state-dependent $K_D$ values for LuxN from the in vivo data: in the phosphatase (off) state $K_{off}^{AI-1} \approx 1$ nM, and in the kinase (on) state $K_{on}^{C450-0730} \approx 500$ nM.

We had reasoned that the dark phenotypes of our LuxN mutants could stem from (i) a defect in the ability to bind AI-1, (ii) a bias favoring the kinase state, (iii) a defect in signaling, or (iv) some combination of the above. The method of data collapse provides a powerful tool to distinguish among these possibilities. For example, consider the case of the mutant LuxN F163A (FIG. 4B) which has an AI-1 $EC_{50}$ value 378-fold higher than that of wild-type LuxN and for which dose-response curves were obtained in the presence of 0 μM, 1 μM, and 10 μM of the antagonist C450-0730. First, we were able to collapse the three antagonist dose-response curves using the identical $K_{on/off}^{AI-1/C450-0730}$ as we used to collapse the wild-type LuxN data indicating that LuxN F163A is not defective in its ability to bind AI-1 (eliminating possibility (i)). Second, the LuxN F163A data could all be collapsed onto the wild-type LuxN antagonist curves simply by adjusting the free-energy bias between the kinase (on) and phosphatase (off) states (FIG. 4C). This analysis allows us to conclude that LuxN F163A has an increased AI-1 $EC_{50}$ value exclusively because it has an altered free-energy bias that favors the kinase (on) state, establishing that possibility (ii) accounts for the dark phenotype of this mutant. Similar analysis applied to our other dark mutants reveals examples of the different possibilities and allows us to deduce and quantify the origins of the dark phenotypes.

Example 5

Antagonist Suppressor Analysis

To better understand the mechanism of C450-0730 interaction with LuxN, a suppressor screen was performed to identify LuxN mutants no longer antagonized by C450-0730. Using error-prone PCR, 2,000 mutants in the luxN N-terminal region were generated and conjugated into the *V. harveyi* ΔluxMN ΔluxPQ ΔluxS strain, HLS253, and arrayed in 96-well micro-titer plates. As mentioned, *V. harveyi* HLS253 is constitutively bright due to the absence of the quorum-sensing receptors, LuxN and LuxPQ, and both autoinducer synthases, LuxM and LuxS. To verify our strategy, a wild-type luxN control plasmid was also conjugated into *V. harveyi* HLS253, which conferred a dark phenotype because wild-type LuxN is a kinase in the absence of AI-L. Bioluminescence is restored to HLS253 containing wild-type luxN by the exogenous addition of 100 nM AI-1. We found that 800 nM C450-0730 was required to inhibit bioluminescence of HLS253 carrying wild-type luxN in the presence of 100 nM AI-1. The luxN mutant library was screened in the presence of 100 nM AI-1 and 800 nM C450-0730 for luxN alleles that enabled bioluminescence in *V. harveyi* HLS253. To eliminate luxN null mutants, the luxN mutant library was also screened in *V. harveyi* HLS253 in the absence of both AI-1 and C450-0730. The luxN alleles that conferred a bright phenotype in the absence of AI-1 were not examined further. Five LuxN mutant strains, LRS112, LRS311, LRS129, LRS147, and LRS1511 (Table 2) displayed dark phenotypes in the absence of AI-1 and C450-0730, but were bright in the simultaneous presence of AI-1 and C450-0730, suggesting that these LuxN proteins were no longer antagonized by C450-0730. The luxN mutations were sequenced to identify the alleles (Table 2). Interestingly, LuxN G271D was identified twice. From here forward this class of suppressor mutants is referred to as LuxN*.

Example 6

Characterization of the LuxN* Mutants

We speculated that the LuxN* mutants could have increased AI-1 sensitivity or decreased C450-0730 binding ability. To distinguish between these two possibilities, the LuxN* AI-1 $EC_{50}$ values were determined (FIG. 9A). As a reference, the dark mutant LuxN F163A is also included in FIG. 9A. The $EC_{50}$ value of wild-type LuxN is 23 nM, while LuxN* S184N is 11 nM, LuxN* I209F is 39 nM, LuxN* R245L is 4.8 nM, and LuxN* G271D is 3.7 nM (Table 1). Interestingly, three of the four LuxN* mutants, LuxN S184N, R245L, and G271D show increased sensitivity to AI-1, suggesting that these alleles circumvent C450-0730 antagonism through increased AI-1 binding or signaling or via a bias to the phosphatase state of LuxN (see Discussion). However, LuxN* I209F responded more like wild type to AI-1 as indicated by an AI-1 $EC_{50}$ value of 39 nM (Table 1).

In the reciprocal experiment, we determined the ability of C450-0730 to antagonize the LuxN* mutants. C450-0730 $IC_{50}$ values were measured by titrating C450-0730 from 0.64 nM to 50 μM, while keeping the AI-1 concentration constant at 10 nM. The C450-0730 concentration required to inhibit LuxN* G271D, R245L, and S184N was similar to that required to inhibit wild-type LuxN, indicating that the observed "resistance" to C450-0730 was indeed due to increased sensitivity to AI-1. However, a 5-fold higher concentration of C450-0730 was required to antagonize LuxN* I209F. Therefore, the LuxN* I209F mutation appears to affect C450-0730 binding. Because 1209 is located within our proposed AI-1 binding site (FIG. 1B in triangle), and because it also affects C450-0730 antagonistic activity, we propose that C450-0730 could compete for the AI-1 binding site of LuxN. This conclusion is strongly supported by the good data collapse in FIG. 4C, which is based on competitive inhibition by C450-0730.

Example 7

Sensitive LuxN* Mutations are Epistatic to the LuxN Dark Mutations

For chemotaxis receptors in *E. coli*, adaptive methylation of specific cytoplasmic residues is known to additively bias receptors toward a kinase-active state. By analogy, we wondered whether some of our single-residue mutations might bias LuxN toward kinase or phosphatase states in an additive manner. To determine whether the LuxN G271D, R245L, and S184N mutants which have lower than wild type AI-1 $EC_{50}$ values are biased toward the phosphatase state, these mutations were engineered into the LuxN F163A mutant to test if they could shift the high $EC_{50}$ of LuxN F163A back toward a low $EC_{50}$. As a reminder, the F163A LuxN mutation has an increased AI-1 $EC_{50}$ value of 8.7 µM as compared to 23 nM for wild-type LuxN; therefore, it requires approximately 378 times more AI-1 to switch LuxN F163A into the phosphatase mode than the amount of AI-1 required to switch wild-type LuxN. A double mutant (LuxN F163A/R245L), a triple mutant (LuxN F163A/R245L/S184N), and a quadruple mutant (LuxN F163A/R245L/S184N/G271D) of LuxN were tested for their ability to respond to AI-1 (FIG. 9B). The incorporation of each LuxN* mutation into the context of the F163A mutation successively decreased the AI-1 $EC_{50}$ value approximately 10-fold, while the quadruple mutant had a constitutively bright phenotype (Table 1). From this analysis, we inferred that the LuxN* mutations are additive in their ability to bias LuxN toward the phosphatase mode.

Example 8

LuxN Antagonists Also Antagonize Cytoplasmic LuxR-Type Homoserine Lactone Receptor LuxN is the founding member of an increasingly large family of membrane bound homoserine lactone autoinducer binding proteins. In this receptor family, autoinducer binding information is transduced to a DNA binding protein by phosphorylation. There are two quorum sensing mechanisms for homoserine lactone autoinducer detection. First, through membrane bound receptors homologous to *V. harveyi*'s LuxN (FIG. 10A). Second, by cytoplasmic LuxR-type proteins, such as CviR from *Chromobacterium violaceum*, in which binding of the homoserine lactone signal allows the LuxR-type receptor protein to fold and bind DNA to alter transcription (FIG. 10B).

After having successfully screened for antagonists of LuxN, the membrane bound homoserine lactone receptor, we tested whether these same antagonists could antagonize a cytoplasmic LuxR-type homoserine lactone receptor. We used *Chromobacterium violaceum* CviR because inhibition results in loss of purple pigment production (FIG. 11). Five of the LuxN antagonists greatly inhibited the cytoplasmic CviR receptor. These data show that these molecules work on both the outside and the inside of the bacterial cell.

Molecule 4606-4237 allows the CviR protein to fold and bind DNA exactly as does the endogenous homoserine lactone ligand. However, the CviR-4606-4237 complex cannot activate transcription.

Example 9

Antagonist Molecules Inhibit Pathogenicity in Bacterial Pathogenesis Model System

Figure 5:
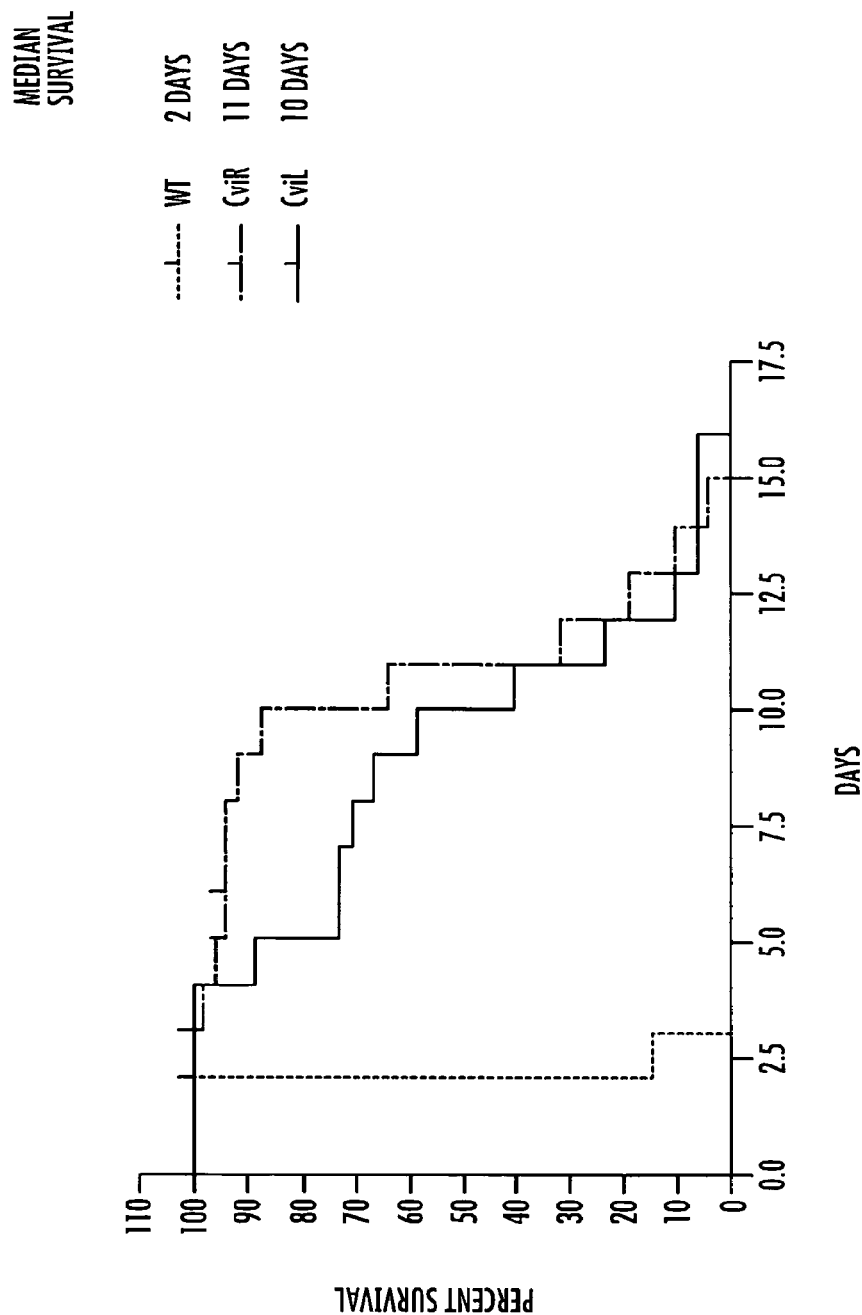
FIG. 5. *C. violaceum* (wild type) but not the Mutant ΔCviR or ΔCviI are Pathogenic to *C. elegans*. The nematode *C.*

*Chromobacterium violaceum* is pathogenic to the nematode *Caenorhabditis elegans*. This is a classic bacterial-host pathogenesis model. Killing of *C. elegans* is quorum-sensing controlled. As such, ΔCviI (homoserine lactone production) and ΔCviR (cytoplasmic receptor) mutants of *C. violaceum* are avirulent (FIG. 5). Wild type *C. violaceum* were pathogenic in *C. elegans* with median survival time of two days. In contrast, *C. elegans* infected with mutant *C. violaceum* that lacked a functioning CviI gene (controlling homoserine lactone production) or CviR gene (autoinducer receptor protein) had a median survival time of ten days or eleven days, respectively. Molecule 4606-4237, a thiolactone, inhibits *C. violaceum* from killing the nematodes (FIG. 13). This example utilized the synthase mutant strain (CviI) of *C. violaceum* (median survival 12 days) to infect *C. elegans*. When the bacteria were supplemented with exogenous homoserine lactone (HSL) autoinducer, the median survival of *C. elegans* was reduced to 4 days. However, the effect of HSL was abolished when the bacteria were supplemented with a combination of homoserine lactone and the thiolactone antagonist 4606-4237. Under those conditions, the median survival of *C. elegans* was 12 days. When the bacteria were supplemented with the thiolactone antagonist alone, median survival was 14 days. Inhibition requires CviR (the cytoplasmic receptor protein).

Experimental Procedures of the Examples

Bacterial Strains and Media

All *V. harveyi* strains were derived from *V. harveyi* BB120 and grown aerobically at 30° C. in either Luria-Marine (LM) broth or Autoinducer Bioassay (AB) broth. Plasmids were maintained in *E. coli* strain XL10Gold (Stratagene) at 37° C. in LB broth. Tri-parental conjugations were performed with the helper plasmid pRK2013 as described (Ditta, G., et al. (1980). Proc Natl Acad Sci USA 77, 7347-7351). When needed, chloramphenicol (Cm) was added to a final concentration of 10 µg/ml and IPTG to a final concentration of 500 µM. A list of strains and plasmids used in this study is provided in Table 3.

DNA Manipulations

DNA manipulations were performed as described in Sambrook et al (Sambrook et al., 1989). PCR reactions were performed using Herculase Enhanced DNA polymerase (Stratagene). Restriction endonucleases, dNTPs, and T4 ligase were purchased from New England Biolabs. Site-directed mutagenesis was performed using the Quickchange II Site-Directed mutagenesis kit (Stratagene). QIAGEN methods were used for plasmid preparations and PCR cleanups. Sequences of primers are available by request.

LuxN Mutant Library Construction

The luxN gene was amplified from wild-type *V. harveyi* BB120 by PCR and cloned into vector pFED343 at the EcoRI and NcoI sites, making pLS1001. Mutagenesis of the first 950 bases of luxN was performed using the error-prone PCR kit Genemorph II EZclone (Stratagene). Resulting mutations were cloned into vector pFED343. The luxN mutant library was conjugated into *V. harveyi* ΔluxN ΔluxPQ strain, JMH625. Ex-conjugates were selected on LM medium agar supplemented with Cm. Approximately 30,000 mutants were screened for reduced bioluminescence. Plasmids from dark mutants were isolated and backcrossed into *V. harveyi* JMH625 to confirm phenotypes. The luxN genes were sequenced and all mutations were engineered independently using Quikchange site-directed mutagenesis (Stratagene). All single luxN mutant constructs were conjugated into *V. harveyi* JMH625 to verify the phenotypes.

*V. harveyi* Strain Construction

To construct the *V. harveyi* ΔluxMN, ΔluxPQ, ΔluxS mutant strain, HLS253, the luxMN operon was deleted from strain FED119 (Neiditch, M. B., et al. (2006). Cell 126, 1095-1108). Specifically, cosmid pBB1754, carrying luxMN was modified by deleting DNA specifying the entire luxMN open reading frame. The resulting plasmid, p1754::ΔluxMN, was introduced into *V. harveyi* FED119, and the deletion transferred to the chromosome to generate *V. harveyi* strain, HLS253.

Bioluminescence Assays

AI-1 dose-response curves were generated in *V. harveyi* strain HLS253 containing a vector with wild-type luxN or one of the luxN mutants. *V. harveyi* strains were grown overnight in LM medium containing Cm and diluted 1:10000 in AB medium plus Cm and 0.5 mM IPTG in triplicate in 96-well microtiter plates. AI-1 was added at either 100 μM or 500 μM and serial 4-fold dilutions were made to final AI-1 concentrations of 24 pM and 119 pM, respectively. The cultures were allowed to grow to stationary phase, at which time bioluminescence and optical density were measured using a Perkin Elmer Envision plate reader.

Quantitative Real-Time PCR Analysis

Wild type and luxN mutant *V. harveyi* strains were grown in LM medium in triplicate to an $OD_{600}$ of 1.0 after which cell pellets were isolated and flash-frozen using liquid nitrogen. Pellets were stored at −80° C. prior to RNA isolation. RNA was isolated and treated with DNase using the Ribo-Pure-Bacteria kit (Applied Biosystems; Foster City, Calif.). RNA was quantified and 1 μg of RNA was converted to cDNA using Superscript II reverse transcriptase (Invitrogen; Carlsbad, Calif.). Quantitative real-time PCR analysis was performed with primers for qrr4 and hfq, where hfq served as an internal control (Tu and Bassler, 2007).

Screen for LuxN Antagonists

The *V. harveyi* strains, JMH624 and JMH610 were grown overnight in AB medium and diluted 1:100 prior to the exogenous addition of either 20 nM AI-1 or 20 nM AI-2, respectively. The diluted cultures were dispensed into 384 well micro-titer plates and the potential antagonist molecules were added to each well. Each micro-titer plate was duplicated to eliminate variance. The 35,000 molecule library was supplied by the Broad Institute and the Initiative for Chemical Genetics (Cambridge, Mass.). Antagonist activity was measured as a function of bioluminescence on a PerkinElmer Envision plate reader.

LuxN Suppressor Screen

The luxN mutant library was conjugated into *V. harveyi* strain HLS253 and selected on LM containing Cm. Colonies were inoculated into 96-well micro-titer plates containing LM broth and Cm and grown at 30° C. with aeration to stationary phase. Glycerol was added to a final concentration of 20%, and the library was stored at −80° C. Frozen stocks were partially thawed and used to inoculate duplicate 96-well micro-titer plates containing AB medium with Cm and IPTG. To one plate, 100 nM AI-1 and 800 nM antagonist C450-0730 was added, while the duplicate control plate had neither AI-1 nor C450-0730 added. The plates were incubated at 30° C. with aeration until the cultures reached stationary phase, at which time bioluminescence was measured and the two plates compared. Strains from wells that produced light in the AI-1/C450-0730 plates but did not produce light in the control plates (no AI-1/no C450-0730) were analyzed further. The luxN mutant plasmids were sequenced to determine the mutations responsible for the observed phenotypes and the mutations were reengineered using Quikchange site-directed mutagenesis (Stratagene; La Jolla, Calif.).

LuxN Free Energies, Competitive Binding, and Data Collapse

In equilibrium, the probability for a LuxN to be active as a kinase is determined by the free-energy difference, $f=f_{on}-f_{off}$, between its kinase (on) and phosphatase (off) states according to $$p_{on} = \frac{1}{1+e^f}. \quad (\text{Eq. \#1})$$

(We measure all energies in units of the thermal energy $k_B T$.) Assuming competitive binding of AI-1 and C450-0730, one obtains $$f = \Delta\varepsilon + \log\left(\frac{1 + \frac{[AI-1]}{K_{off}^{AI-1}}}{1 + \frac{[AI-1]}{K_{on}^{AI-1}}}\right) + \log\left(\frac{1 + \frac{[C450-0730]}{K_{off}^{C450-0730}}}{1 + \frac{[C450-0730]}{K_{on}^{C450-0730}}}\right), \quad (\text{Eq. \#2})$$

where $K_{on/off}^{AI-1/C450-0730}$ is the dissociation constant for the given state and ligand, and the "bias" $\Delta\varepsilon$ is the value of f at zero ligand concentration (Keymer, J. E., et al. (2006). Proc Natl Acad Sci USA 103, 1786-1791).

To test for competitive binding of C450-0730 to LuxN, we assume that bioluminescence is some (unknown) function of the fraction of LuxN proteins that are active as kinases, i.e. bioluminescence is a function of $f$. We therefore plot bioluminescence as a function of $f-\Delta\varepsilon_{WT}$, as given in Eq. #2, and search for the values of $K_{on/off}^{AI-1/C450-0730}$ that collapse all of our data onto a single curve. The results are shown in FIG. 4C.

To quantitatively test whether LuxN mutations that shift AI-1 $EC_{50}$ values can be attributed to changes in the bias $\Delta\varepsilon$ and/or the AI-1 binding affinities, we attempted to collapse the AI-1 dose-response curves for each mutant onto the wild-type curve (FIG. 15B) using $\Delta\varepsilon_{mutant}-\Delta\varepsilon_{WT}$ and in some cases $K_{off}^{AI-1}$ as fitting parameters. The collapse was satisfactory for many but not all cases, as discussed in the text.

TABLE 1

LuxN Mutant Phenotypes

| Allele | Lux Phenotpye | AI-1 $EC_{50}$ (M) | Fold change in $EC_{50}$[a] | Location |
|---|---|---|---|---|
| Wild type | WT | $2.3 \times 10^{-8}$ | | |
| H46Y | WT | NM | | TM2 |
| S54P | WT | NM | | TM2 |
| A77D | WT | NM | | PL1 |
| H155Q | WT | NM | | CL1 |
| N133A[b] | Dark | $8.2 \times 10^{-8}$ | 3.6 | TM4 |
| L138A | WT | $3.0 \times 10^{-8}$ | 1.3 | TM4 |
| T139A | WT | $1.4 \times 10^{-8}$ | 0.6 | TM4 |
| T139I | Dark | $7.4 \times 10^{-8}$ | 3.2 | TM4 |
| V140A | WT | NM | | PL2 |
| V143A | Dark | $9.9 \times 10^{-8}$ | 4.3 | PL2 |
| I145A | WT | NM | | PL2 |
| P148A | WT | NM | | PL2 |
| S149A | WT | $6.1 \times 10^{-8}$ | 2.7 | PL2 |
| F151A | Dark | $6.9 \times 10^{-5}$ | 3000 | PL2 |
| I153A | Dark | $1.2 \times 10^{-6}$ | 52.2 | PL2 |
| I153F | Dark | $1.3 \times 10^{-7}$ | 5.7 | PL2 |
| I153L | WT | $6.6 \times 10^{-8}$ | 2.9 | PL2 |
| E154Q | WT | $5.5 \times 10^{-8}$ | 2.4 | PL2 |
| E154A | WT | NM | | PL2 |
| F155A | Dark | $5.8 \times 10^{-7}$ | 25.2 | PL2 |
| F155I | Dark | $8.1 \times 10^{-4}$ | 35217 | PL2 |
| F155L | Dark | $4.1 \times 10^{-6}$ | 178.3 | PL2 |
| G156A | WT | NM | | PL2 |
| P157A | WT | NM | | PL2 |
| F162A | Dark | $9.3 \times 10^{-5}$ | 4043 | TM5 |
| F163A | Dark | $8.7 \times 10^{-6}$ | 378.3 | TM5 |
| L166A | Dark | NA | | TM5 |
| L166R | Dark | $2.3 \times 10^{-7}$ | 10.0 | TM5 |
| V170A | WT | NM | | TM5 |
| T173A | WT | NM | | TM5 |
| N176A | WT | NM | | TM5 |
| S184N | Sensitive | $1.1 \times 10^{-8}$ | 0.5 | CL2 |
| K186A | WT | NM | | CL2 |
| L187A | WT | NM | | CL2 |
| A190T | WT | NM | | CL2 |
| K191A | WT | NM | | CL2 |
| Y194A | WT | NM | | TM6 |
| G198A | WT | NM | | TM6 |
| I199A | WT | NM | | TM6 |
| F202A | Dark | NA | | TM6 |

TABLE 1-continued

LuxN Mutant Phenotypes

| Allele | Lux Phenotpye | AI-1 $EC_{50}$ (M) | Fold change in $EC_{50}$[a] | Location |
|---|---|---|---|---|
| F202Y | Dark | $7.1 \times 10^{-7}$ | 30.9 | TM6 |
| S205A | WT | $3.2 \times 10^{-8}$ | 1.4 | TM6 |
| S205P | Dark | NA | | TM6 |
| T206A | Dark | $3.1 \times 10^{-7}$ | 13.5 | TM6 |
| I209F | WT | $3.9 \times 10^{-8}$ | 1.7 | TM6 |
| G212A | WT | $3.6 \times 10^{-8}$ | 1.6 | TM6 |
| T214A | Dark | $4.5 \times 10^{-7}$ | 19.6 | TM6 |
| T214I | Dark | $7.0 \times 10^{-5}$ | 1043 | TM6 |
| D219A | Dark | $1.3 \times 10^{-7}$ | 5.7 | PL3 |
| F220A | Dark | $1.9 \times 10^{-4}$ | 8261 | PL3 |
| F220I | Dark | $7.1 \times 10^{-4}$ | 30870 | PL3 |
| S221A | Dark | $1.9 \times 10^{-7}$ | 8.3 | PL3 |
| W224A | Dark | $1.9 \times 10^{-7}$ | 8.3 | TM7 |
| L225A | WT | $5.5 \times 10^{-8}$ | 2.4 | TM7 |
| P226A | Dark | $2.3 \times 10^{-4}$ | 10000 | TM7 |
| P226T | Dark | NA | | TM7 |
| P227A | Dark | $4.0 \times 10^{-6}$ | 173.9 | TM7 |
| P227L | Dark | $3.9 \times 10^{-3}$ | 169565 | TM7 |
| L229A | WT | NM | | TM7 |
| S230A | WT | NM | | TM7 |
| S232A | Dark | $4.0 \times 10^{-7}$ | 17.4 | TM7 |
| S232N | WT | $4.1 \times 10^{-8}$ | 1.8 | TM7 |
| E233A | Dark | NA | | TM7 |
| M234I | WT | NM | | TM7 |
| M234A | WT | NM | | TM7 |
| G238A | WT | NM | | TM7 |
| Y239A | WT | NM | | TM7 |
| R245L | Sensitive | $4.8 \times 10^{-9}$ | 0.21 | CL4 |
| V249I | WT | NM | | CL4 |
| G271D | Sensitive | $3.7 \times 10^{-9}$ | 0.16 | TM8 |
| F163A/R245L | Dark | $3.7 \times 10^{-6}$ | 160.9 | |
| F163A/R245L/S184N | Dark | $1.4 \times 10^{-7}$ | 6 | |
| F163A/R245L/S184N/G271D | Sensitive | NA | | |

[a]Fold change in $EC_{50}$ value with respect to wild-type $EC_{50}$ value.
[b]Bold indicated 100% conserved amino acids. (See FIG. 2)
TM (Trans-Membrane Domain)
CL (Cytoplasmic Loop)
PL (Periplasmic Loop)
NM (Not Measured)
NA (Not Applicable)

TABLE 2

LuxN Mutants Identified in the Random Mutant Screen.

| Strain | Allele |
|---|---|
| LRS3 | P226T[a] |
| LRS5 | Basepair 634 deleted |
| LRS6 | F155L, A190T, F202Y |
| LRS11 | S205P |
| LRS12 | T214I |
| LRS13 | H46Y, F220I, V249I |
| LRS14 | G212A, T214I |
| LRS16 | S54P, H115Q, T139I |
| LRS19 | A77D, P227L, S232N, M234I |
| LRS20 | D219A |
| LRS112 | V21M, G165D, S184N |
| LRS311 | I209F |
| LRS129 | F93L, G271D, L292H |
| LRS147 | M2171, G271D |
| LRS1511 | R247L, Y301F |

[a]Bold indicates alleles that confer a defective LuxN phenotype when tested independently.

TABLE 3

Strains and Plasmids Used in this Study.

| Strain or Plasmid | Relevant Feature | Reference or Source |
|---|---|---|
| BB120 | Wild type | (Bassler et al., 1997) |
| JMH624 | ΔluxM luxQ::Tn5 | unpublished |
| JMH625 | ΔluxN luxQ::Tn5 | (Henke and Bassler, 2004b) |
| JMH610 | ΔluxS luxN::Tn5 | (Neiditch et al., 2006) |
| BB721 | luxO::Tn5 | (Bassler et al., 1994) |
| FED119 | ΔluxPQ ΔluxS luxN::Tn5 | (Neiditch et al., 2006) |
| HLS253 | ΔluxMN ΔluxPQ ΔluxS | This Study |
| pRK2013 | Broad host range, tra, Kan$^r$ | (Ditta et al., 1980) |
| pPHIJ1 | Broad host range, tra, mob, Gm$^r$ | (Beringer, 1978) |
| pCP20 | Ts FLP recombinase plasmid; Amp$^r$ | (Datsenko and Wanner, 2000) |
| pBB1754 | pLAFR with luxMN::TN5 | (Bassler et al., 1993) |
| pLS1121 | pBB1754 with ΔluxMN | This Study |
| pFED343 | pEVS143 Cm$^r$ | Unpublished |
| pLS1001 | pFED343 with luxN locus | This Study |

All publications and patents mentioned in this document are herein incorporated by reference. The present invention is not limited to the embodiments described and exemplified above, but is capable of variation and modification within the scope of the appended claims.

---

The invention claimed is:
1. A pharmaceutical composition comprising a pharmaceutically acceptable carrier, adjuvant or vehicle and a pharmaceutically-acceptable salt of a small molecule compound whose structure is selected from the group consisting of:
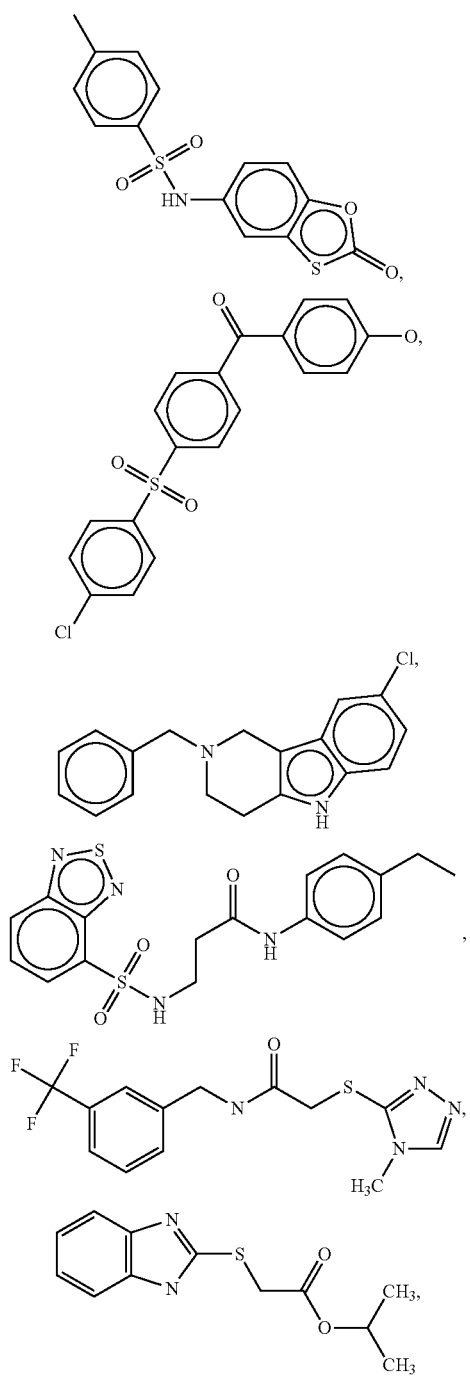
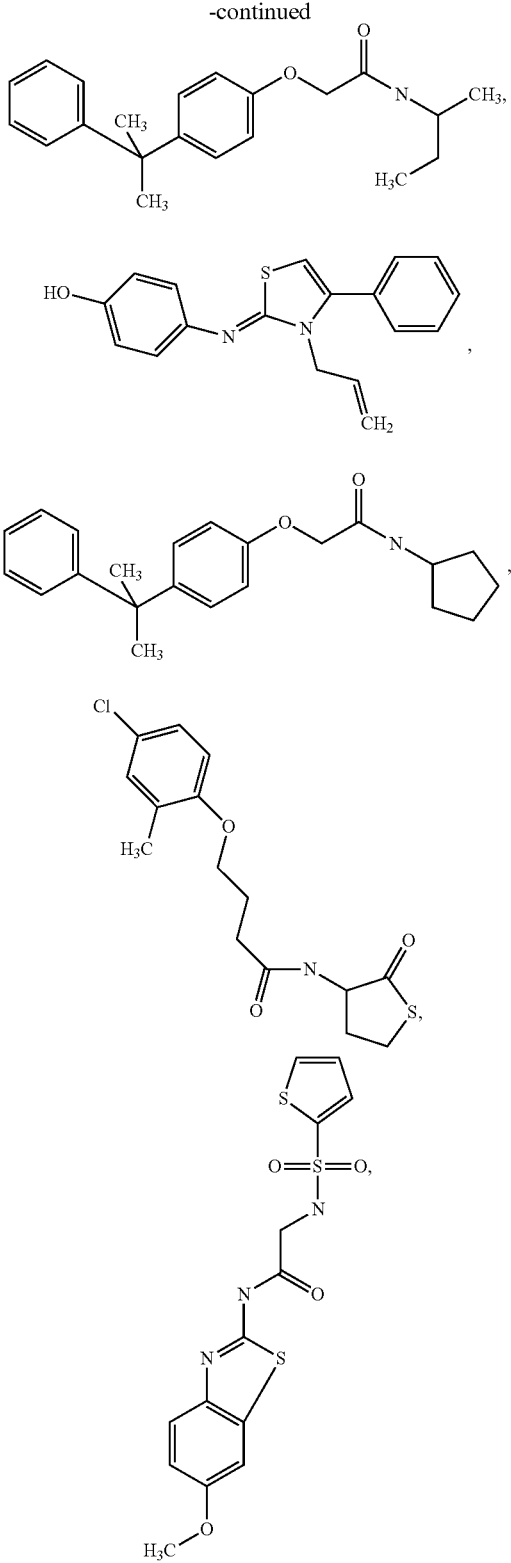

-continued

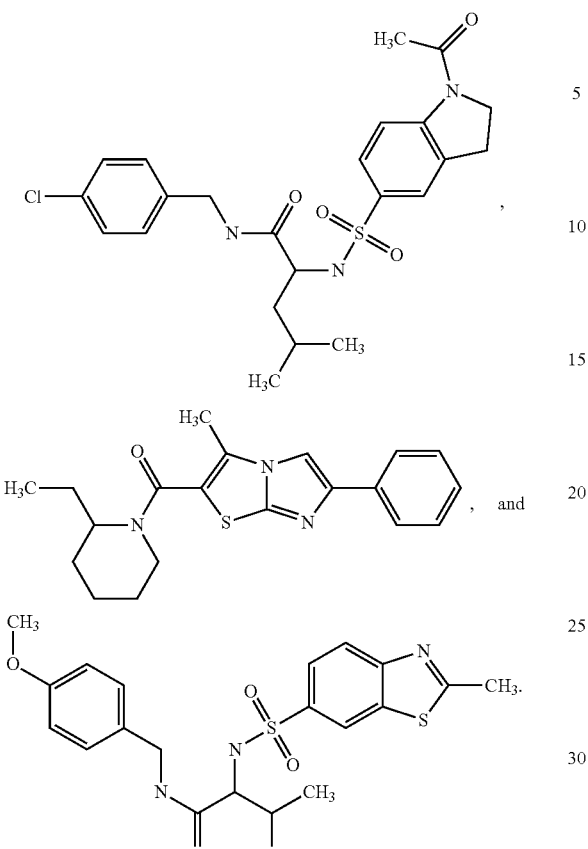

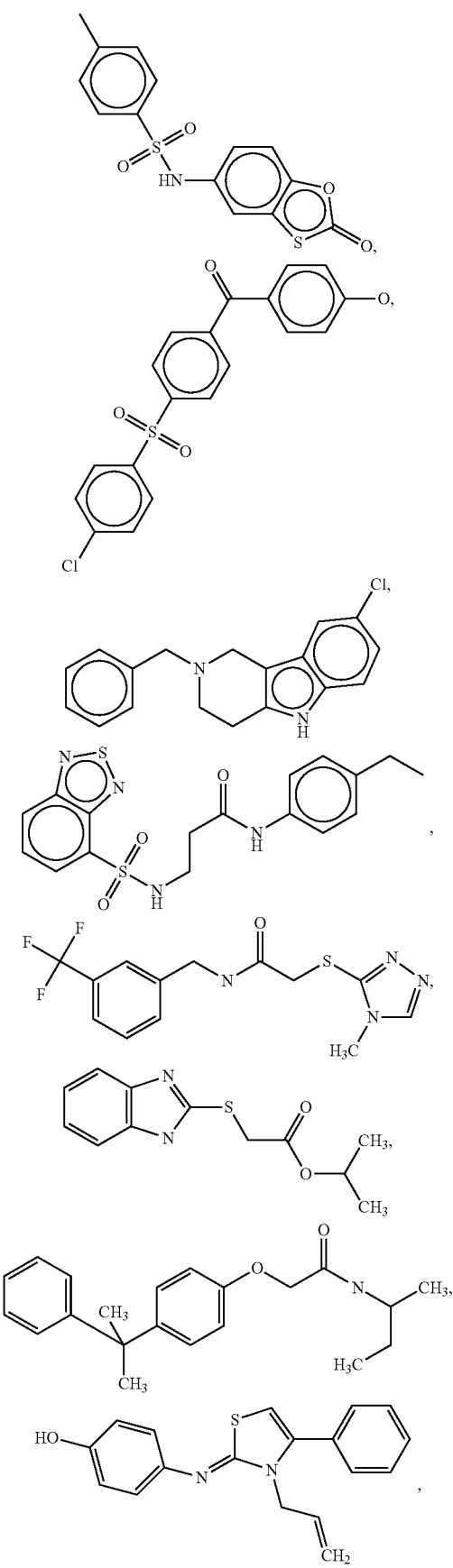

2. The pharmaceutical composition of claim 1 that is a solid dosage form.

3. The pharmaceutical composition of claim 2 that is in the form of capsules, tablets, pills, powders, tinctures or granules.

4. The pharmaceutical composition of claim 2 wherein the salt of the small molecule compound is admixed with at least one inert pharmaceutically acceptable carrier.

5. The pharmaceutical composition of claim 4 wherein the carrier is sucrose, lactose, or starch.

6. The pharmaceutical composition of claim 2 that comprises one or more lubricating agents.

7. The pharmaceutical composition of claim 3 that comprises a buffering agent.

8. The pharmaceutical composition of claim 3 that comprises an enteric coating.

9. A method of treatment for infection of a host by gram-negative quorum-sensing bacteria, which comprises administering to the host a therapeutically effective amount of the pharmaceutical composition of claim 1.

10. The method of claim 9 that is administered orally, nasally, topically or parenterally.

11. The method of claim 9 for treatment for *Vibrio* bacteria infection.

12. A method of inhibiting infection of *Vibrio* bacteria in shellfish comprising contacting the bacteria with a small molecule a small molecule compound whose structure is selected from the group consisting of:

-continued
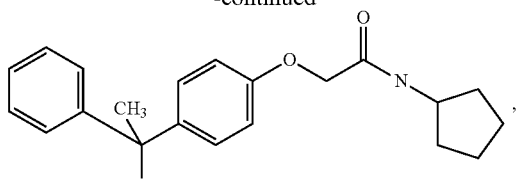
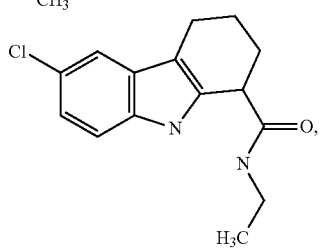
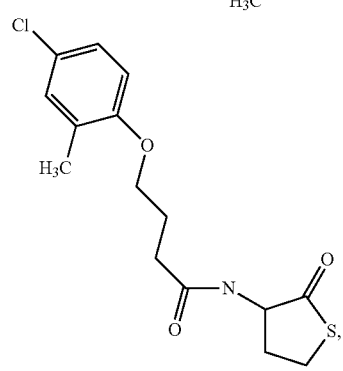
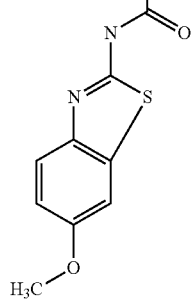
-continued
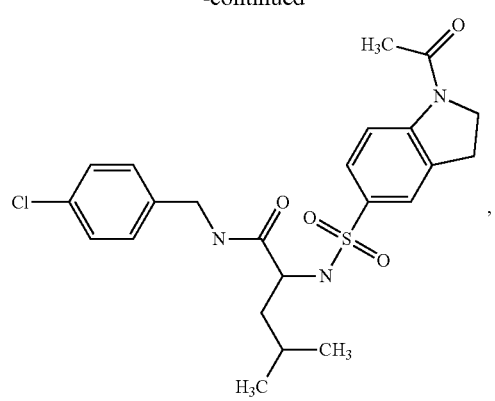
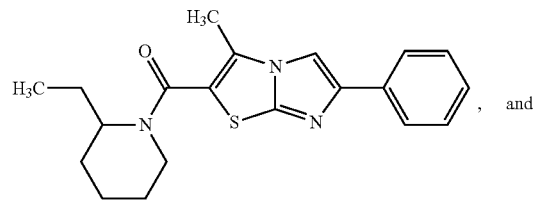
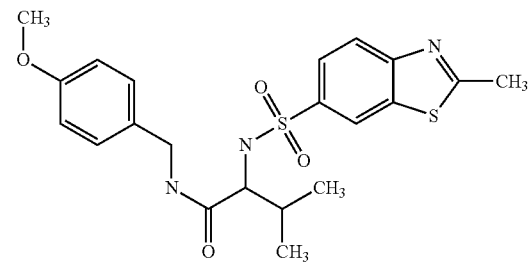
in a concentration sufficient to dis